(12) United States Patent
Prado

(10) Patent No.: US 9,028,522 B1
(45) Date of Patent: May 12, 2015

(54) TISSUE DILATOR AND RETRACTOR SYSTEM AND METHOD OF USE

(71) Applicant: SeaSpine, Inc., Vista, CA (US)

(72) Inventor: Gustavo R. Prado, San Diego, CA (US)

(73) Assignee: Seaspine, Inc., Vista, CA (US)

( * ) Notice: Subject to any disclaimer, the term of this patent is extended or adjusted under 35 U.S.C. 154(b) by 68 days.

(21) Appl. No.: 13/678,092

(22) Filed: Nov. 15, 2012

Related U.S. Application Data

(60) Provisional application No. 61/560,123, filed on Nov. 15, 2011.

(51) Int. Cl.
*A61M 29/00* (2006.01)
*A61B 17/02* (2006.01)

(52) U.S. Cl.
CPC .................... *A61B 17/025* (2013.01)

(58) Field of Classification Search
USPC .................................................. 606/90, 191
See application file for complete search history.

(56) References Cited

U.S. PATENT DOCUMENTS

| | | | |
|---|---|---|---|
| 4,545,374 A | 10/1985 | Jacobson | |
| 5,357,983 A | 10/1994 | Mathews | |
| 5,423,826 A | 6/1995 | Coates et al. | |
| 5,472,426 A | 12/1995 | Bonati et al. | |
| 5,496,322 A | 3/1996 | Mathews | |
| 5,569,248 A | 10/1996 | Mathews | |
| 5,667,513 A | 9/1997 | Torrie et al. | |
| 5,728,097 A | 3/1998 | Mathews | |
| 5,902,231 A | 5/1999 | Foley et al. | |
| 5,954,635 A | 9/1999 | Foley et al. | |
| 5,954,671 A | 9/1999 | O'Neill | |
| 6,007,487 A | 12/1999 | Foley et al. | |
| 6,152,871 A | 11/2000 | Foley et al. | |
| 6,176,823 B1 | 1/2001 | Foley et al. | |
| 6,206,822 B1 | 3/2001 | Foley et al. | |
| 6,217,509 B1 | 4/2001 | Foley et al. | |
| 6,425,859 B1 | 7/2002 | Foley et al. | |
| 6,520,907 B1 | 2/2003 | Foley et al. | |
| 6,793,656 B1 | 9/2004 | Mathews | |
| 6,827,722 B1 | 12/2004 | Schoenefeld | |
| 6,837,891 B2 | 1/2005 | Davison et al. | |
| 7,160,300 B2 | 1/2007 | Jackson | |
| 7,179,261 B2 | 2/2007 | Sicvol et al. | |
| 7,250,052 B2 | 7/2007 | Landry et al. | |
| 7,306,603 B2 | 12/2007 | Boehm, Jr. et al. | |
| 7,434,325 B2 | 10/2008 | Foley et al. | |
| 7,588,575 B2 | 9/2009 | Colleran et al. | |
| 7,699,852 B2 | 4/2010 | Frankel et al. | |
| 7,811,288 B2 | 10/2010 | Jones et al. | |
| 7,909,830 B2 | 3/2011 | Frigg et al. | |
| 8,062,217 B2 | 11/2011 | Boucher et al. | |
| 8,096,996 B2 | 1/2012 | Gutierrez et al. | |

(Continued)

*Primary Examiner* — Sameh Boles
(74) *Attorney, Agent, or Firm* — Middleton Reutlinger; Robert H. Eichenberger; Chad D. Bruggeman

(57) ABSTRACT

Disclosed is an apparatus and a method for surgical dilation and retraction of tissues during a medical procedure, for example a spinal surgery. The apparatus includes a dilator assembly that includes a plurality of slidingly engaging dilators, wherein at least one dilator includes an outer wall shape different from its inner wall shape. At least one of the dilators may include an eccentrically positioned circular channel, a generally oblong outer wall shape, and a longitudinal gap in a wall. The dilator system may be used in a method that provides off center differential dilation of tissues in one or more preferred directions. A retractor system that may be used with the dilator system is also disclosed.

17 Claims, 49 Drawing Sheets

(56) References Cited

U.S. PATENT DOCUMENTS

| | | |
|---|---|---|
| 8,100,915 B2 | 1/2012 | Jackson |
| 8,100,951 B2 | 1/2012 | Justis et al. |
| 2002/0116006 A1 | 8/2002 | Cohen |
| 2003/0083688 A1* | 5/2003 | Simonson ............ 606/191 |
| 2005/0085813 A1 | 4/2005 | Spitler et al. |
| 2005/0131408 A1 | 6/2005 | Sicvol et al. |
| 2005/0131421 A1 | 6/2005 | Anderson et al. |
| 2005/0154389 A1 | 7/2005 | Selover et al. |
| 2008/0140132 A1 | 6/2008 | Perez-Cruet |
| 2010/0114147 A1* | 5/2010 | Biyani ............ 606/191 |
| 2011/0144687 A1 | 6/2011 | Kleiner |
| 2012/0232658 A1* | 9/2012 | Morgenstern Lopez et al. ............ 623/17.16 |

\* cited by examiner

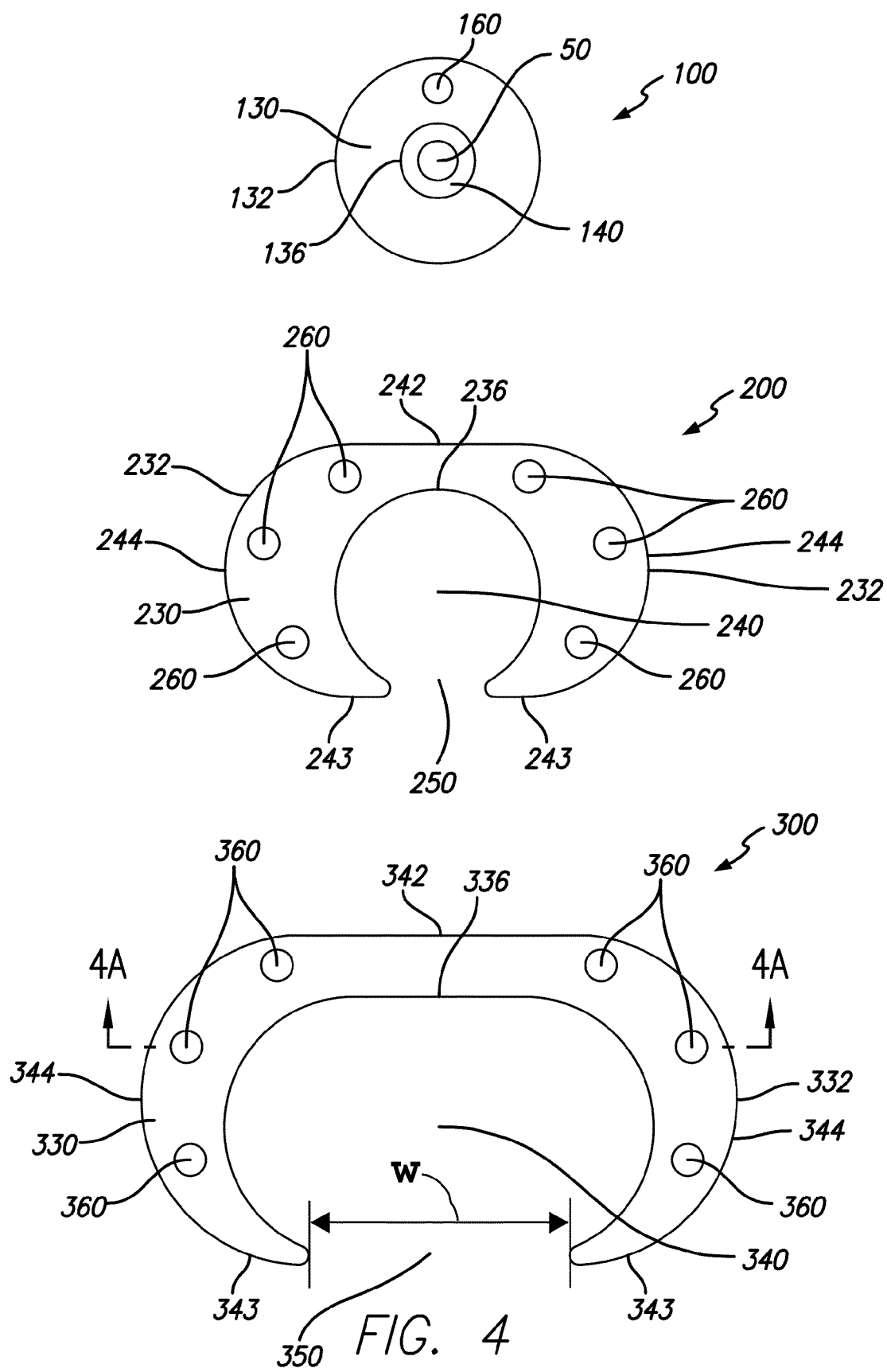

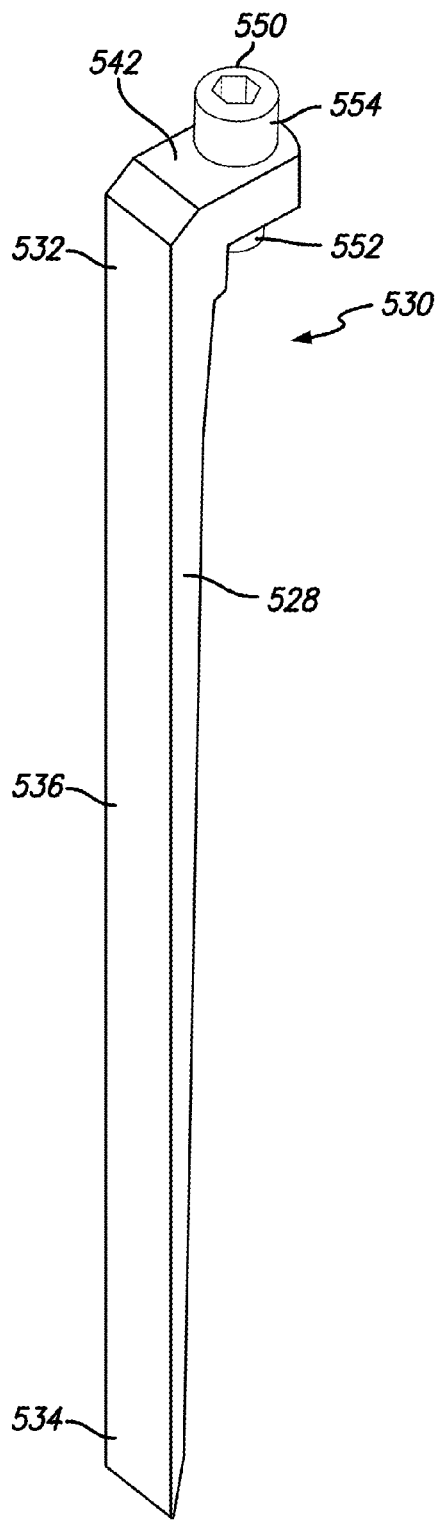
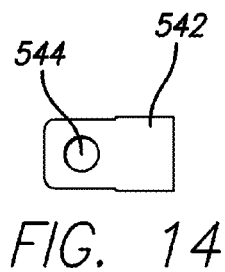
FIG. 14
FIG. 13
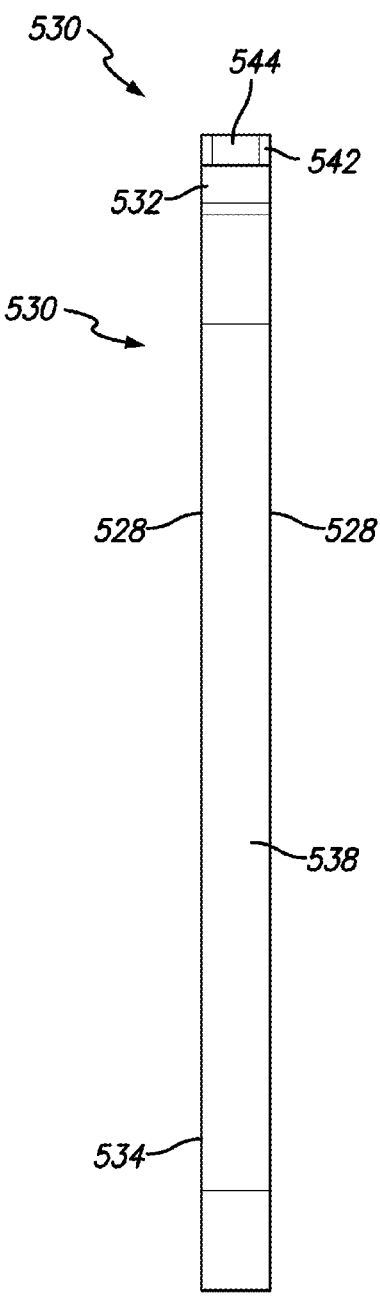
FIG. 15

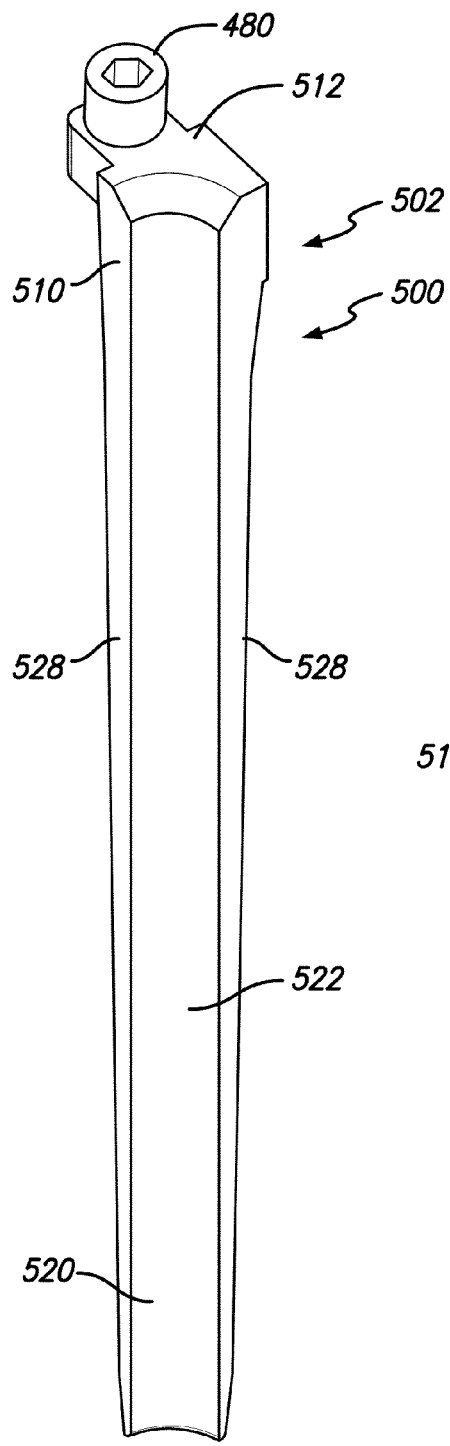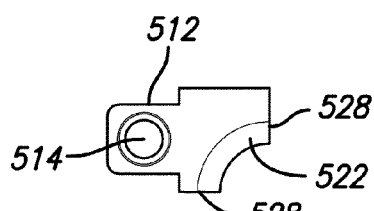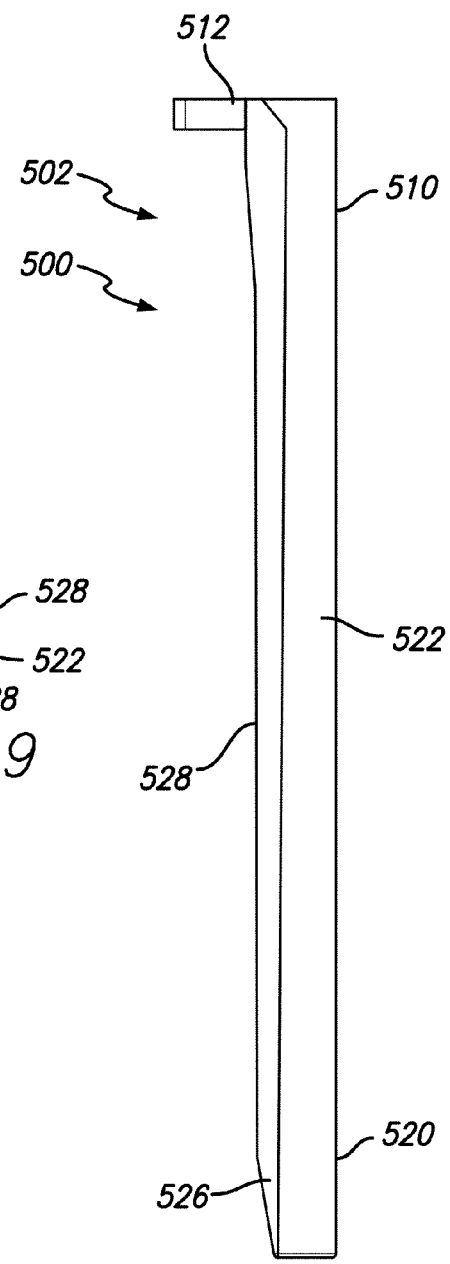
FIG. 18
FIG. 19
FIG. 20

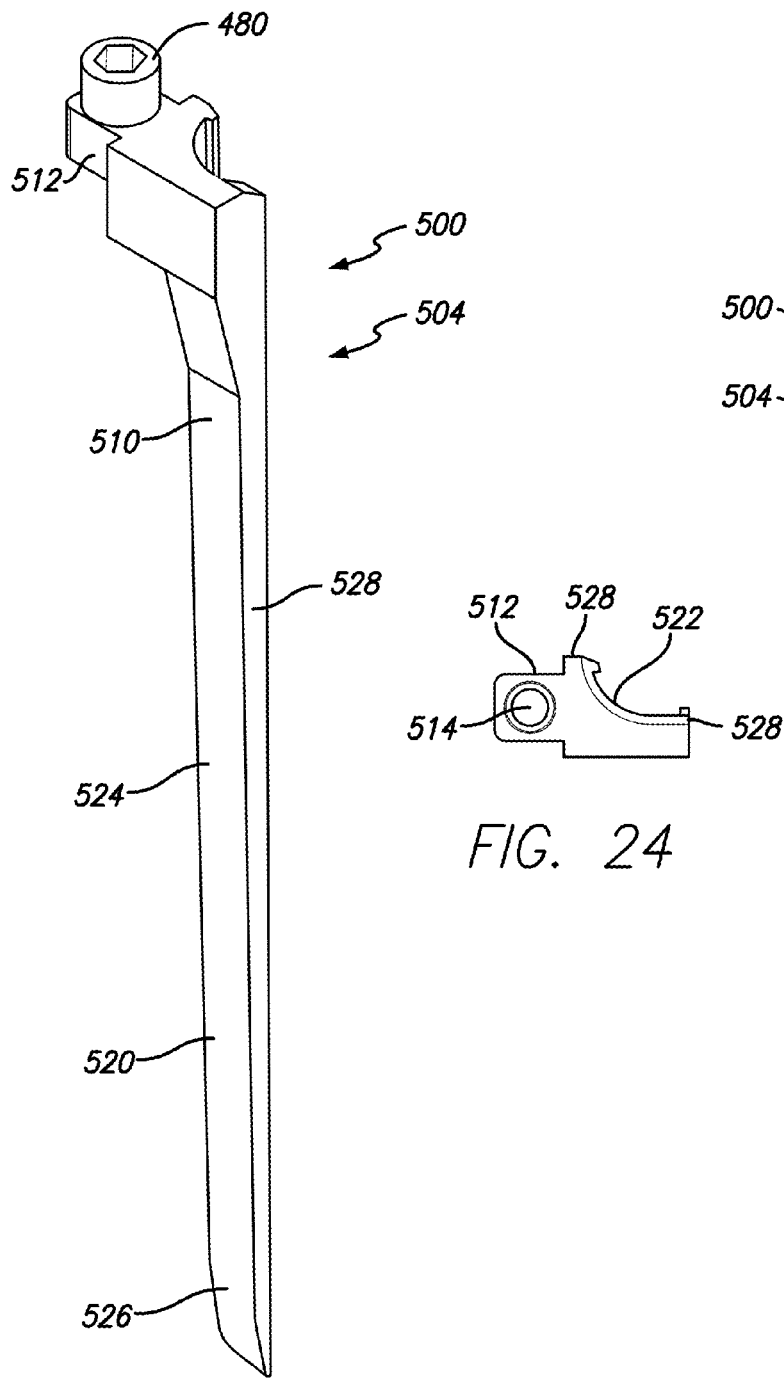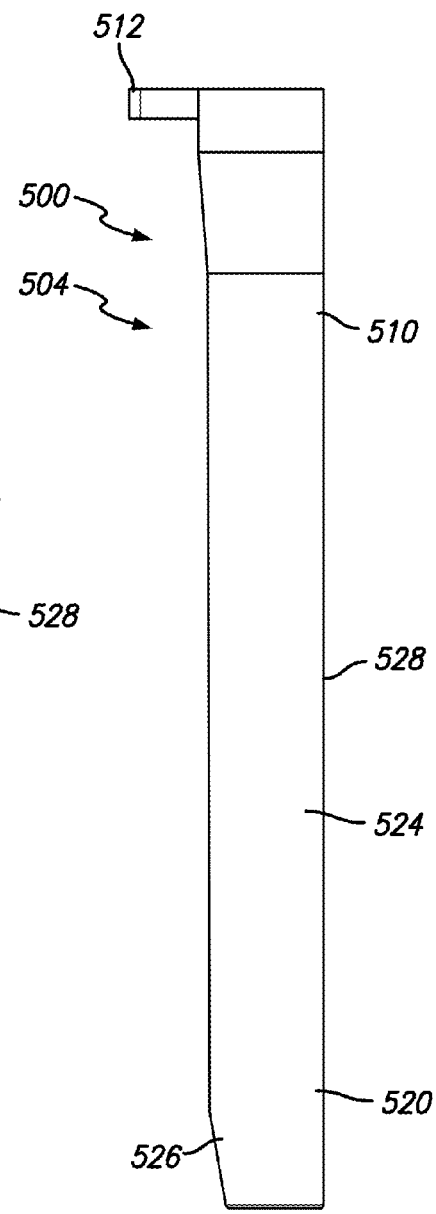
FIG. 23
FIG. 24
FIG. 25

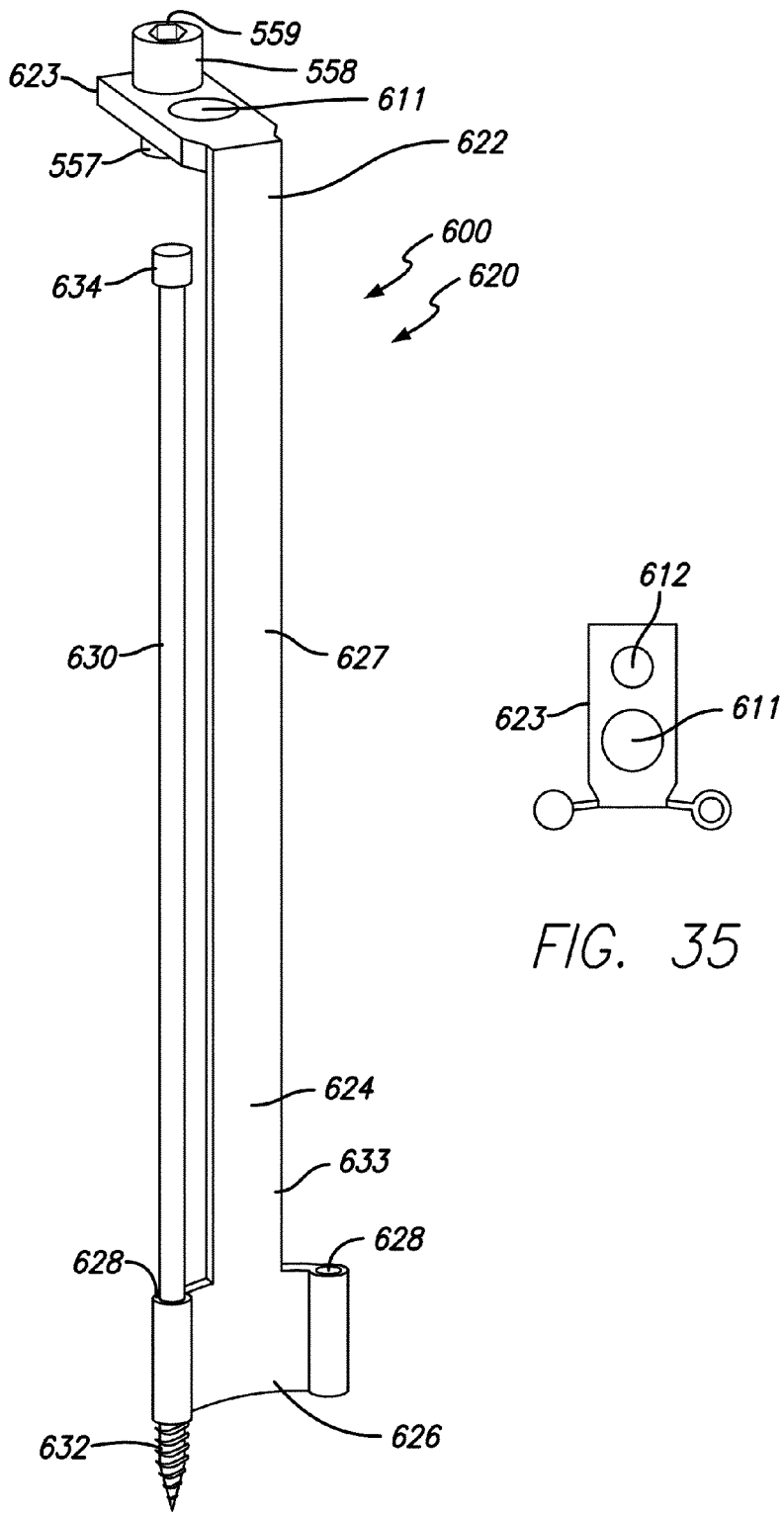
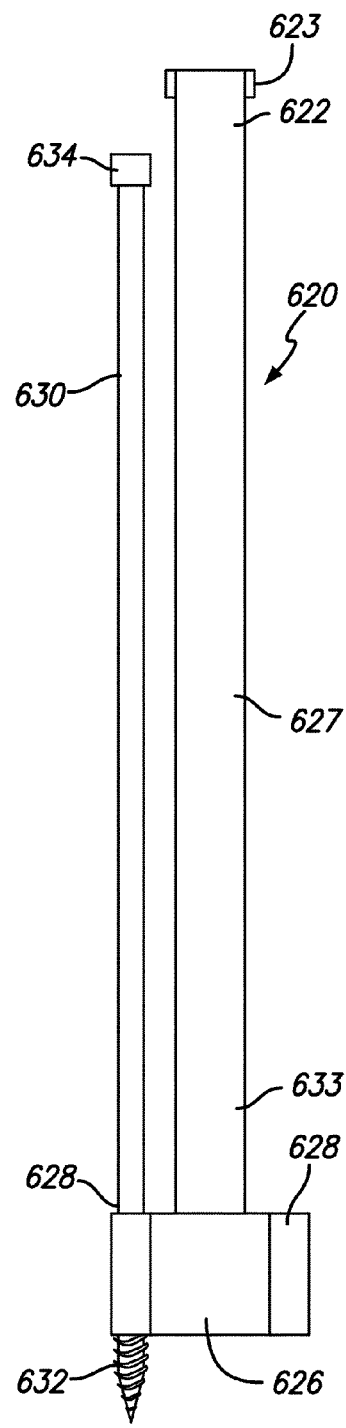
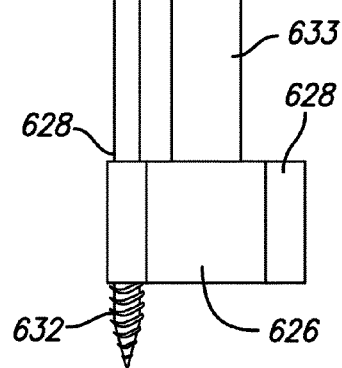
FIG. 34
FIG. 35
FIG. 36

TISSUE DILATOR AND RETRACTOR SYSTEM AND METHOD OF USE

CROSS-REFERENCE TO PRIOR APPLICATION

This application claims priority to and benefit under 35 U.S.C. §119(e) to U.S. Provisional Application Ser. No. 61/560,123, filed on Nov. 15, 2011, which is incorporated herein by reference.

FIELD OF THE INVENTION

The present invention relates generally to surgical tissue dilators and surgical retractors. More specifically, the present invention relates to a spinal surgery tissue dilator system and tissue retractor system.

BACKGROUND OF THE INVENTION

A trend in surgery has included minimally invasive dilation of biological tissues during surgical procedures. Minimally invasive dilation of tissues is advantageous in providing transcutaneous access to deeper anatomical structures while avoiding or minimizing the cutting or tearing of muscle and other tissues. Typically, tissue dilators include a series of tubular devices, each having round cross-sectional profiles of slowly increasing outer diameters. The first dilator in the series has a minimal cross-sectional profile and subsequent larger diameter dilators are concentrically longitudinally advanced over the previous smaller diameter dilator. Circular dilator systems have an advantage of minimal trauma to tissue as the circular dilator is advanced and turned within tissue. Subsequently advanced concentric dilators provide even dilation of tissues about a first small diameter dilator. However, at least one problem known in the art is that significant off center directional dilation of tissues is not generally provided by concentric generally cylindrical dilators. Preferential directional dilation in an asymmetrical manner is not achieved with such concentric symmetrically shaped dilator systems. Some directional dilation of tissues is provided by prior art dilator systems having round walls and off center lumens. However, such dilator systems are poorly balanced, problematic to rotate, and awkward to use and control. Some relative directional dilation of tissues may be provided by prior art dilators having oblong shapes. However, a problem known in the art is that such prior art dilator systems result in at least some disruption of tissues in all directions about the first initially placed dilator when subsequent dilators are advanced.

Another trend in some dilator systems is dilators including electrodes. Dilators including stimulating electrodes have been advocated as a useful adjunct to neuromonitoring during spinal surgery. One such surgery where neuromonitoring may be advantageous is lateral transpsoas approaches to the lumbar spine. In a transpsoas approach to the spine, nerves are in danger of being damaged during the procedure. Stimulation of one or more electrode of these prior art dilators has been used to trigger an electromyographic (EMG) response that may monitored. Triggered EMG monitoring may be beneficial in detecting proximity of a dilator electrode to neural structures during spinal surgeries, for example transpsoas approaches to the lumbar spine.

After initial approach to the spine using dilators, it is beneficial to further enlarge the wound using a retractor, forming an operative corridor to visualize and access the spine. The retractor may be used to visualize and access a disc space, for example to implant a spinal spacer into the intervertebral body space for arthrodesis.

Therefore, there has been recognized by those skilled in the art a need for minimally invasive dilation of biological tissues using a dilator system during surgical procedures which dilates predominantly in one or more directions while minimizing or completely avoiding dilation of soft tissue in at least one other direction about the longitudinal axis of a first dilator and/or guidewire.

There has also been recognized a need for preferential dilation in an anatomical anterior direction and avoidance of dilation in an anatomical posterior direction by an electrode configured dilator system during a lateral transpsoas approach to the spine. All present dilation systems have a disadvantage of requiring at least some posterior dilation relative to the first placed dilator.

Still another recognized need is for a strong, stable, and secure retractor system that may provide various configurations of operative corridors and that includes blades that may be moved independent of movement of other blades that are attached to a retractor frame.

The present invention fulfills these needs and others.

SUMMARY OF THE INVENTION

Briefly and in general terms, embodiments of the present invention provide a new and improved dilator system. The dilator system may include a generally cylindrical first dilator having a circular outer wall. The dilator system may further include a second oblong dilator having a generally circular inner channel configured to mate with the circular outer wall of the first dilator. The second dilator channel may be eccentrically positioned towards a posterior gap in the wall of the second dilator. The dilator system may still additionally include a third oblong dilator having an oblong inner channel configured to slidingly mate over an oblong outer wall of a second dilator. The channel of the third dilator may be eccentrically positioned towards a gap in the posterior wall of the third dilator.

One aspect of the present invention includes a dilator system capable of preferential directional dilation of tissues in anatomical rostral and caudal directions, while providing an intermediate amount of dilation of tissues in an anatomical anterior direction, and additionally minimizing or avoiding dilation of soft tissues in an anatomical posterior direction. The dilator system may minimize or avoid dilation of tissue in an anatomically posterior direction as sequential dilators are advanced over a first positioned dilator. The first dilator may be generally cylindrical and subsequent dilators generally oblong.

Furthermore, embodiments of the invention provide a method of preferential directional dilation of tissues in anatomical rostral and caudal directions, while providing lesser dilation of tissues in an anatomical anterior direction, and avoiding dilation of soft tissues located posterior to the first dilator.

In accordance with certain aspects of the present invention there is also provided a dilator system and method of use of the system for monitoring of proximity of the dilator to nerves. At least one dilator may include one or more stimulating or monitoring electrodes extending longitudinally in a wall of the dilator.

Still another aspect of the invention is a dilator system including a first dilator, a second dilator, and a third dilator. There is a first longitudinal gap and an open eccentric channel in the second dilator. There is a second longitudinal gap and open eccentric channel in the third dilator. The first gap in the second dilator is occluded when the second dilator is advanced over the first dilator. When the second dilator is advanced over the first dilator, the second dilator's posterior wall exterior does not extend beyond the first dilator's posterior exterior, wherein posterior dilation of tissue by the second dilator is minimized or avoided. Similarly, the second gap in the third dilator is occluded when the third dilator is advanced over the assembled first and second dilators, wherein posterior dilation of tissue by the third dilator is minimized or avoided.

In yet a further aspect of the invention, a dilator system is provided including a first dilator having an exterior periphery defined by an exterior wall. The dilator system further includes a second trough-like dilator including an open proximal end, an open distal end, and a channel configured to slidingly mate the first dilator therein, the channel having a longitudinally extending gap disposed between a left side portion and a right side portion of a posterior wall of the second dilator. The channel and gap in the second dilator is configured to prevent dislodgment of the first dilator through the gap. There is an exterior periphery shape about the second dilator that is defined in part by an exterior wall of the second dilator and in part by an imaginary line extending across the gap and generally following the contour of the exterior of the posterior wall. When the second dilator channel is slidingly mated over the first dilator exterior wall, a portion of the exterior wall of the first dilator extends at least to the exterior periphery of the second dilator. In a further aspect of the invention, the dilator system includes a third trough-like dilator including an open proximal end, an open distal end, and a channel configured to slidingly mate the second dilator therein. The third dilator's channel has a longitudinally extending gap disposed between a left side portion and a right side portion of a posterior wall of the third dilator. The third dilator's channel and longitudinal gap is configured to prevent dislodgment of the second dilator through the third dilator's gap. An exterior periphery shape about the third dilator is defined in part by an exterior wall of the third dilator and in part by an imaginary line extending across the gap of the third dilator, and generally following the contour of the exterior surface of the posterior wall of the third dilator. When the third dilator channel is slidingly mated over the second dilator exterior wall, a portion of the exterior wall of the first dilator extends at least to the exterior periphery of the third dilator.

In yet a further aspect of the invention, a dilator system may have a dilator having an interior cross-sectional shape and an exterior cross-sectional shape, the periphery of the interior cross-sectional shape comprises an interior straight-line segment and the exterior cross-sectional shape comprises an exterior straight-line segment, and the interior straight-line segment and the exterior straight-line segment are parallel to each other. The exterior straight-line segment may be longer than the interior straight-line segment.

In yet a further aspect of the invention, a dilator system may have a dilator having an exterior cross-sectional shape, in which the exterior cross-sectional shape comprises an exterior straight-line segment, and the exterior cross-sectional shape comprises a gap having a gap width, and the length of the exterior straight-line segment is greater than the gap width. The length of the exterior straight-line segment may also be greater than the length of a tangent line closing the gap.

In yet a further aspect of the invention, a dilator system may have first, second, and third dilators, and the dilators may be assembled in a cumulative configuration or in a non-cumulative configuration, and when the first, second, and third dilators are assembled in the non-cumulative configuration and an envelope of the third dilator is defined by extending a straight line across the gap of the third dilator such that the straight line is tangent to the external surface of the third dilator at each side of the gap, the second dilator is contained entirely within the envelope of the third dilator.

In further accordance with the present invention, there is provided a retractor system, which may be configured to be mate with and slidingly advanced distally over the dilator system. The retractor system may provide an oblong shaped working channel. In a closed configuration, approximated blades of the retractor system are sized and configured to mate with the outer wall of at least one dilator and slidingly advance over the at least one dilator. In yet further accordance with the present invention there is provided a system and method of enlarging an operative corridor using the retractor system by transitioning the retractor system from a closed configuration to an open configuration.

Still further in accordance with the invention there is provided a retractor system including a variety of retractor blades and a method of providing linear independent movement of the blades following attachment to a retractor frame.

One additional aspect of the invention is a method of using the dilator system and the retractor system to provide access to the spine during a surgical procedure. The method may include providing a first rigid dilator having a central longitudinal axis and a first exterior wall shape. The method may further include advancing the first rigid dilator through soft tissue to the spine and stabilizing the first rigid dilator to a fixed position. The method may additionally include slidingly engaging an eccentric channel positioned adjacent to a longitudinal gap in an exterior wall of a second rigid dilator over an exterior wall of the first dilator, wherein an exterior wall shape of the second rigid dilator is different from the exterior wall shape of the first rigid dilator. The method may include slidingly engaging an eccentric channel positioned adjacent to a longitudinal gap in an exterior wall of a third rigid dilator over an exterior wall of the second dilator, wherein an exterior wall shape of the third rigid dilator is different from the exterior wall shape of the first rigid dilator. The method may also include slidingly advancing a retractor system over at least one of the dilators and transitioning at least one retractor blade from a closed configuration position to an open configuration position.

Other features and advantages of the invention will become more apparent from the following detailed description of preferred embodiments of the invention, when taken in conjunction with the accompanying exemplary drawings.

BRIEF DESCRIPTION OF THE DRAWINGS

These and other features, aspects and advantages of the present invention are described with reference to drawings of a preferred embodiment, which are intended to illustrate, but not to limit, the present invention.

FIG. 4 is top plan view of the first dilator, the second dilator, and the third dilator of the dilator system of FIG. 2.

FIG. 13 is a perspective view of an embodiment of a center blade including a threaded blade attachment screw of one embodiment of a retractor system of the present invention.

FIG. 14 is a top plan view of the center blade of FIG. 13 without the threaded blade attachment screw.

FIG. 15 is a frontal anterior plan view of the center blade of FIG. 13 without the threaded blade attachment screw.

FIG. 18 is an inner surface perspective view of an embodiment of a primary blade of one embodiment of a retractor system of the present invention including a threaded blade attachment screw.

FIG. 19 is a top plan view of the primary blade of FIG. 18 without the threaded blade attachment screw.

FIG. 20 is a frontal plan view of the primary blade of FIG. 18 without the threaded blade attachment screw.

FIG. 23 is an outer surface perspective view of another embodiment of a primary blade of one embodiment of a retractor system of the present invention including a threaded blade attachment screw.

FIG. 24 is a top plan view of the primary blade of FIG. 23 without the threaded blade attachment screw.

FIG. 25 is a frontal plan view of the primary blade of FIG. 23 without the threaded blade attachment screw.

FIG. 34 is a perspective view of another embodiment of an auxiliary blade of an embodiment of the retractor system of the present invention including a threaded blade attachment screw and an elongated anchor pin.

FIG. 35 is a top plan view of the auxiliary blade of FIG. 34 without the threaded blade attachment screw.

FIG. 36 is a frontal plan view of the auxiliary blade of FIG. 34 without the threaded blade attachment screw.

FIG. 60 and FIG. 60A is a perspective view of one embodiment of a probe and one embodiment of a first dilator of the present invention.

DETAILED DESCRIPTION OF THE PREFERRED EMBODIMENTS

Figure 1:
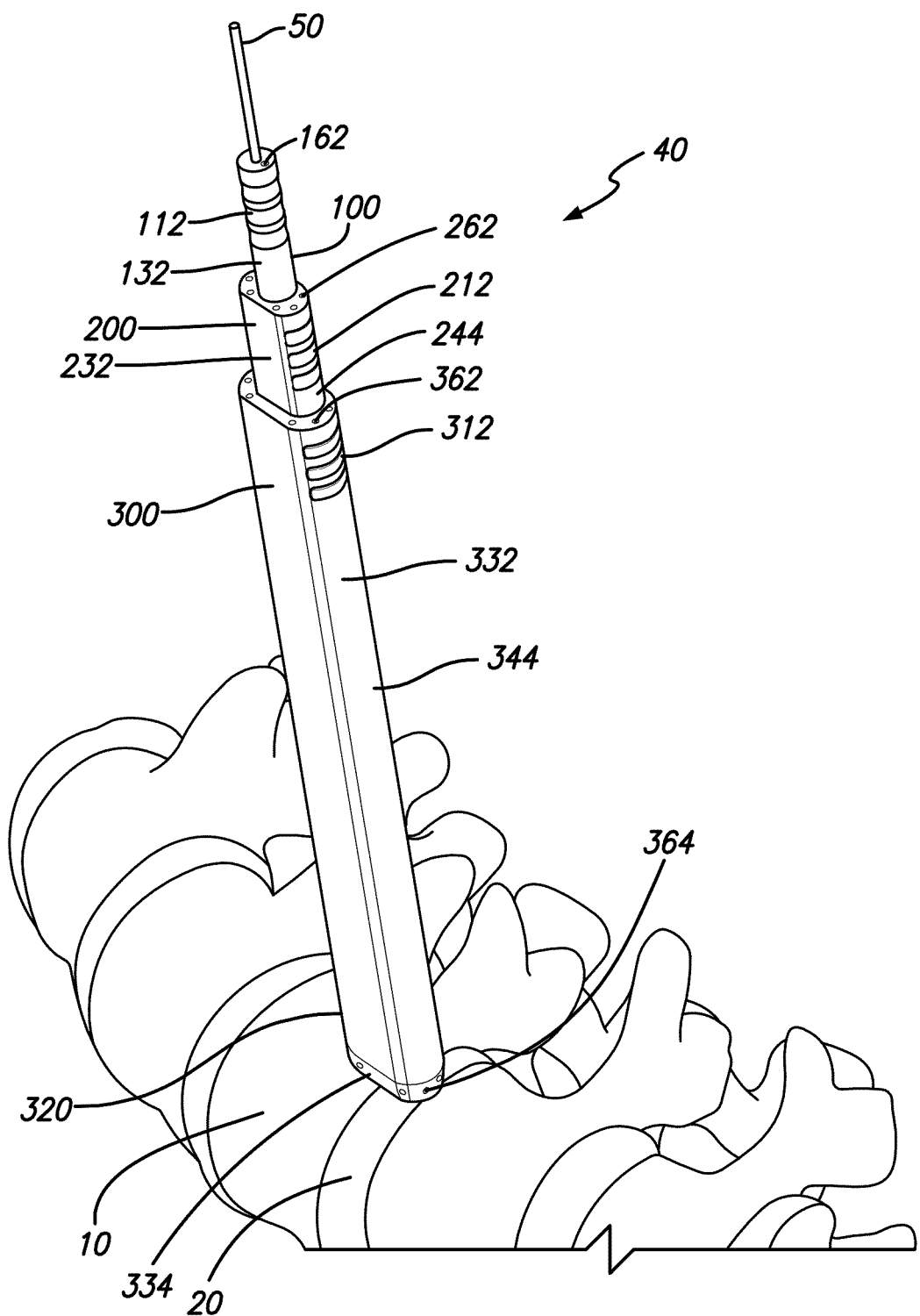
FIG. 1 is a perspective view of an assembled dilator system of one embodiment of the present invention.
Figure 2:
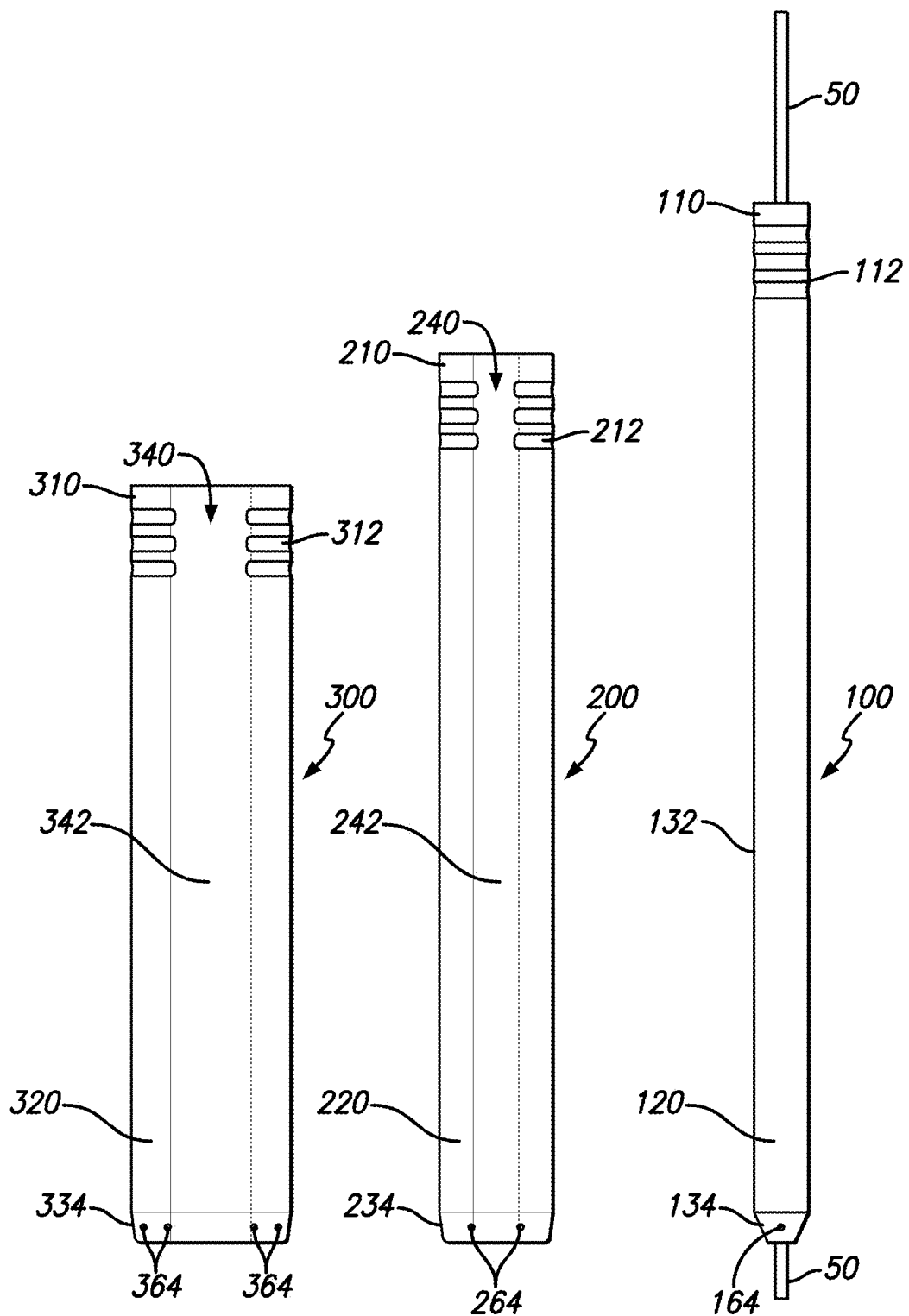
FIG. 2 is disassembled frontal anterior plan views of a first dilator, a second dilator, and a third dilator of the dilator system of FIG. 1.
Figure 3:
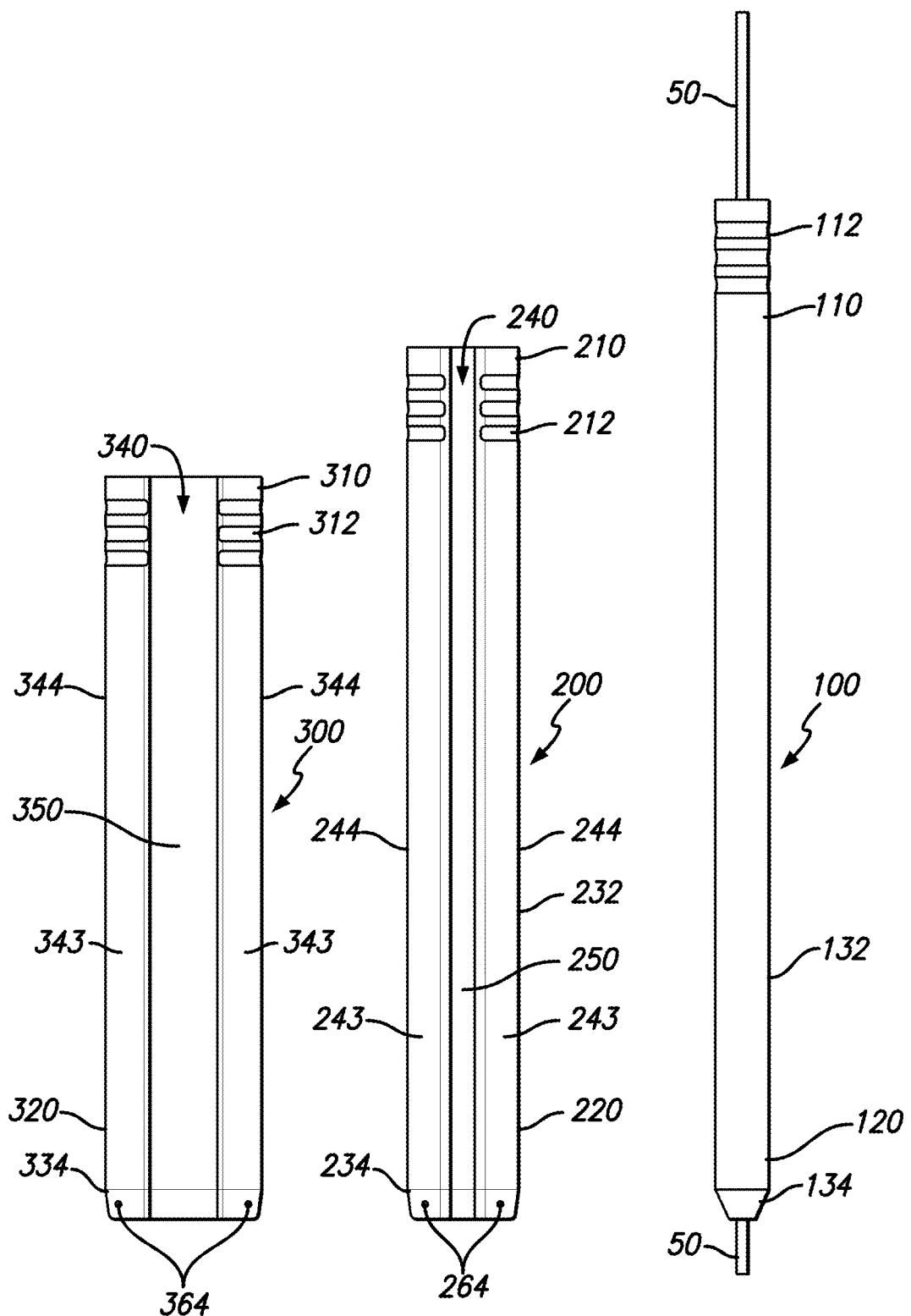
FIG. 3 is back posterior plan views of the first dilator, the second dilator, and the third dilator of the dilator system of FIG. 2.
Figure 68:
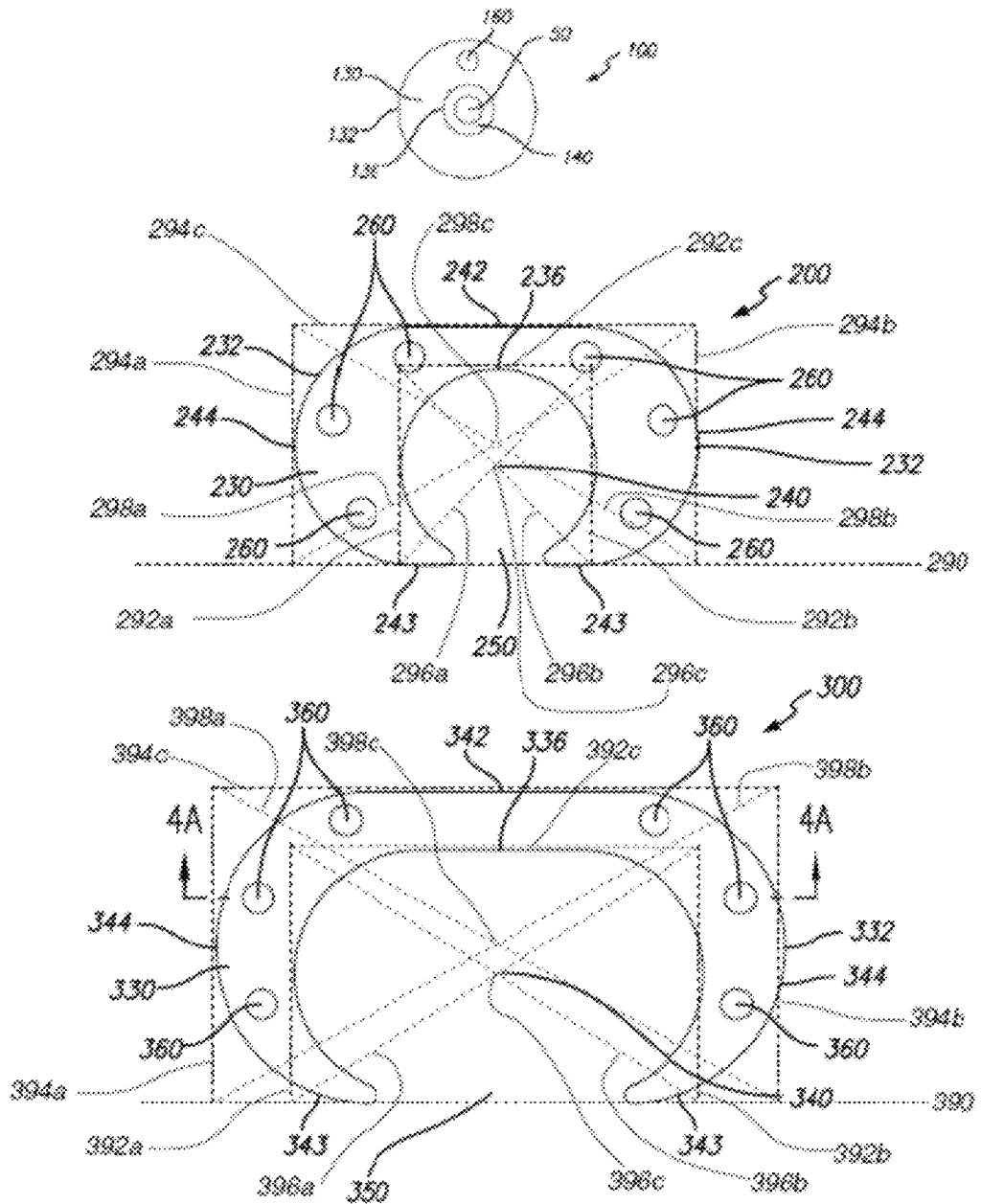
FIG. 68 is an illustration of one method of determining a center of a cross-sectional shape.

Referring to the drawings, which are provided for purposes of illustration and by way of example, at least one embodiment of the present invention of a tissue dilator system, a retractor system, and/or method of use is illustrated in FIGS. 1-68.

The present invention relates to a surgical dilator system and a surgical retractor system. In general terms, in the present invention there is provided a surgical dilator system including an assembly of dilators for minimally traumatic dilation of soft tissues, and a retractor system for surgical retraction of soft tissues. In at least one embodiment the device is useful for surgical access to the vertebral bodies of the spine. In yet another embodiment, the dilator system and retractor system are useful during intervertebral body arthrodesis surgery, arthroplasty, biopsy, and/or discectomy. The present invention, however, is not limited to spinal surgery. The terms anterior, posterior, rostral, caudal, left, or right are used herein to provide relative orientations of portions of the invention to each other and are not intended to limit the use of the invention to particular anatomical orientations. Anatomical relationships shall be designated herein only when the term "anatomical" precedes a word.

Referring to FIGS. 1-6c, in at least one embodiment, the invention includes a sequential tissue dilation system 40 including a guidewire 50 and an assembly of a series of tissue dilators 100, 200, 300. A first dilator 100 has a proximal end 110 and a distal end 120. A second dilator 200 has a proximal end 210 and a distal end 220. A third dilator 300 has a proximal end 310 and a distal end 320. It is to be understood that more or less than three dilators may be used. In at least one embodiment a guidewire 50 is provided that is longer than the first dilator 100. The first dilator may be longer than the second dilator 200. The second dilator may be longer than the third dilator 300. The guidewire 50 may be sized and configured to allow entry of a distal end of the guidewire 50 into an intervertebral body disc space from a transcutaneous entry position. In one embodiment the dilator system 40 may be configured to extend into the patient from a patient's skin incision to the spine. The dilator system may include a distal end that is configured to contact the vertebral bodies 10 and/or disc space 20 of the spine. In at least one embodiment, the dilator system may be used to dilate a patient's tissues along a surgical path from skin to spine while minimizing trauma to the surrounding tissues. The dilator system may also be used to protect the tissues during subsequent steps of a surgical procedure. In one embodiment, one or more of the dilators are substantially rigid. In another embodiment, one or more of the dilators may be substantially flexible.

Figure 4A:
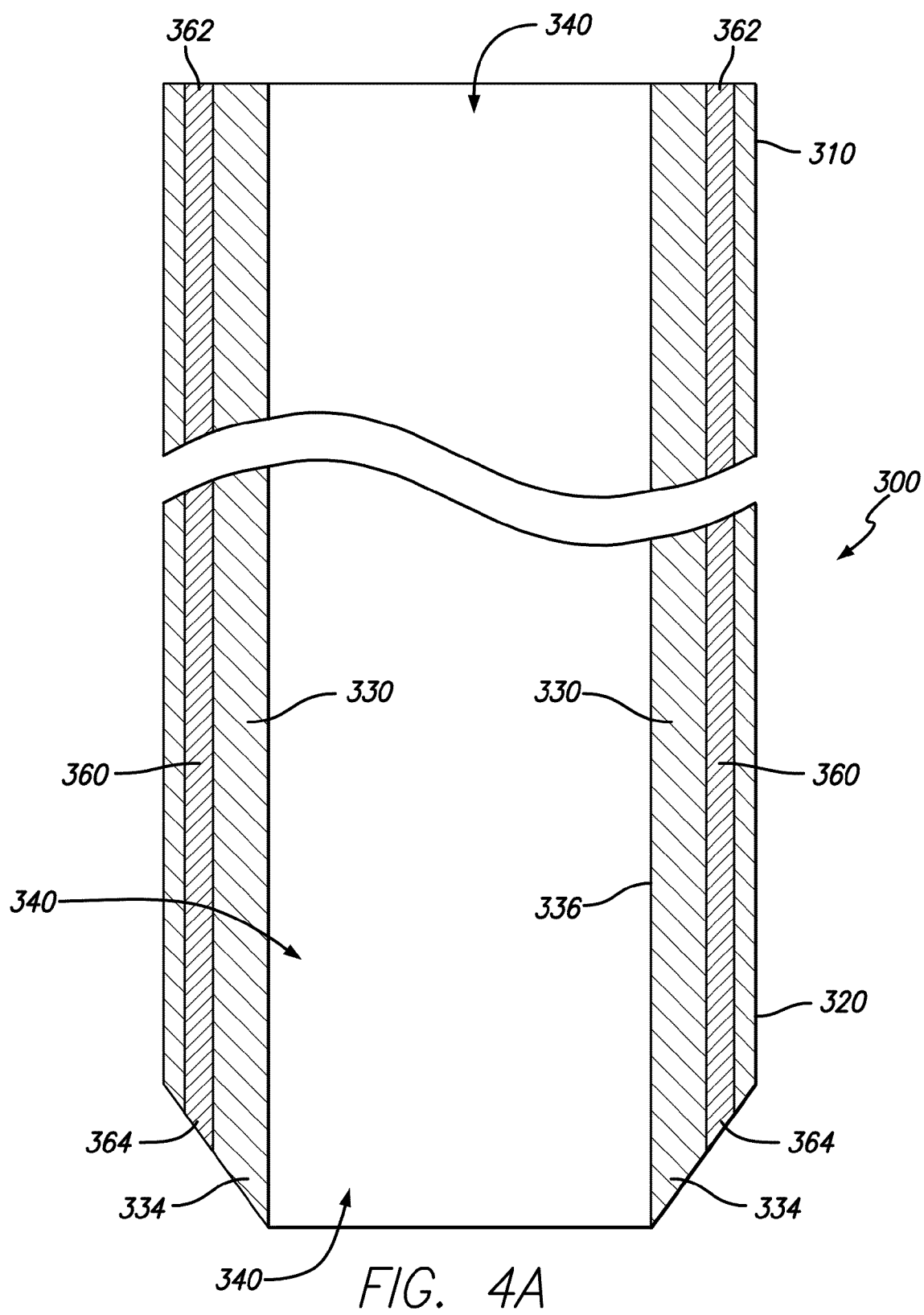
FIG. 4A is a longitudinal cross section view of the third dilator taken through line 4A in FIG. 4.
Figure 4B:
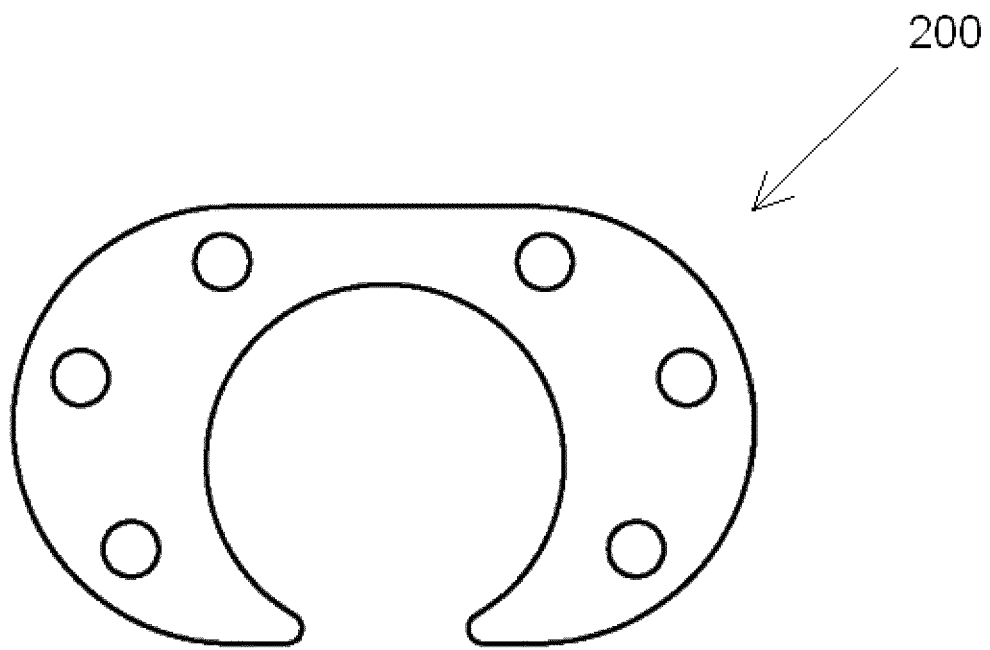
FIG. 4B is a top plan view of the second dilator illustrating orientations of an anterior and/or frontal aspect of the second dilator relative to a posterior and/or rear aspect of the second dilator.
Figure 4C:
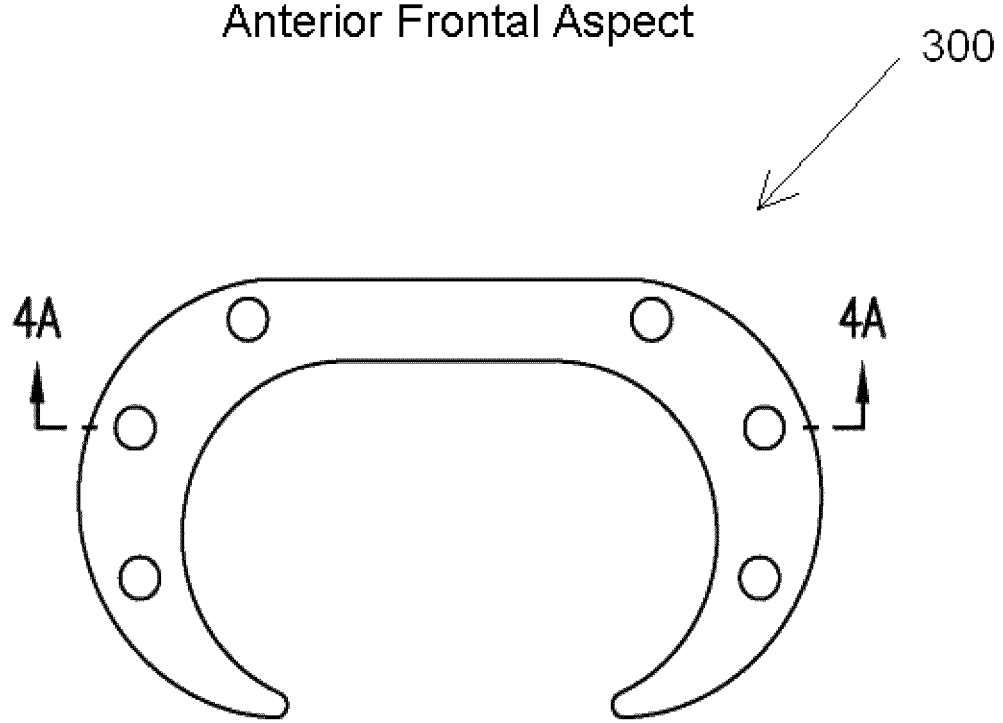
FIG. 4C is a top plan view of the third dilator illustrating orientations of an anterior and/or frontal aspect of the third dilator relative to a posterior and/or rear aspect of the third dilator.

Referring more specifically now to FIG. 4B the second dilator has an anterior and/or frontal aspect as compared to a posterior and/or rear aspect. Referring more specifically now to FIG. 4C the third dilator has an anterior and/or frontal aspect as compared to a relative posterior and/or rear aspect.

Referring again to FIGS. 1-6c, in one embodiment the first dilator 100 may be generally cylindrical. The first dilator may include a wall 130 having an exterior wall surface 132 that may be generally circular shaped in cross section and an inner wall surface 136 forming a lumen 140 that may also be generally circular shaped in cross section. A longitudinal axis may extend through the first dilator. The longitudinal axis may extend generally perpendicularly through the center of the exterior wall's 132 generally circular shape from the proximal end 110 of the dilator to the distal end 120 of the dilator 100. The lumen 140 extends longitudinally within the first dilator 100 from a proximal end 110 of the dilator to a distal end 120 of the dilator and may be configured to receive the guidewire 50 therein and therethrough. The lumen 140 may have a central longitudinal axis extending from the proximal end 110 to the distal end 120 of the generally cylindrical first dilator. In at least one embodiment, the first dilator's 100 circular lumen 140 and the exterior wall circular shape of the first dilator 100 may be generally concentric, wherein the lumen and the exterior wall 132 may have the same central longitudinal axis. In still another embodiment the lumen's central longitudinal axis and the exterior wall's 132 central longitudinal axis may be generally parallel but offset from each other, wherein the lumen is eccentrically positioned within the first dilator.

In one embodiment, the proximal end 110 of first dilator 100 may further include a grip surface 112, which may facilitate control of the first dilator 100 by a surgeon. In at least one embodiment the grip surface includes ring-like recesses formed in the exterior wall surface 132. Other types of recesses or surfaces that provide a texture to the grip surface may be used. The recesses may be formed, in the wall 130 for example, by cutting, etching, molding, milling, laser cutting, or other techniques know in the art. In a further embodiment described in greater detail below, at least one longitudinal electrical conducting member 160 is imbedded in the wall 130 of the first dilator 100. The electrical conducting member extends from an electrical conducting member proximal end 162 to an electrical conducting member distal end 164. In at least one embodiment, the distal end 120 of first dilator 100 may include a tapered distal exterior wall surface 134, for example, a frustoconical surface, which may be useful to minimize trauma to tissues during insertion the first dilator 100. In yet another embodiment, the distal end 120 may be configured with other shapes. In at least one embodiment, a first dilator with the circular shaped exterior wall surface 132 may be advantageous in minimizing trauma to soft tissues, for example, when rotating the first dilator 100 about its central longitudinal axis within tissues. The first dilator may be rotated about its central longitudinal axis as the dilator is being advanced through soft tissues, and/or following positioning of the distal end 120 of first dilator 100 at the intervertebral body disc space 20. In yet other embodiments, the exterior wall surface 132 of first dilator 100 may have various alternative non-circular and/or multisided configurations.

Referring again to FIGS. 1-6c, in at least one embodiment the second dilator 200 includes a wall 230. In at least one embodiment, an exterior wall 232 cross-sectional shape may be a generally oblong shape. The term oblong shape as used herein means a cross-sectional shape that is longer than it is wide. An oblong shape may include, for example, shapes that are generally oval, rectangular, racetrack, or ellipsoidal. The oblong shape in some embodiments may include portions that are generally straight lines and/or portions that are generally curved lines. However, in yet other embodiments the exterior wall surface shape may be round, circular, triangular, square, hexagonal, or any another multisided shape having straight segments and/or curved segments or combinations thereof. The shape may be continuous around its periphery or may include imaginary line segments bridging across any gap and following the general contour of the shape.

The exterior wall cross-sectional shape may have a perimeter that is interrupted by a gap 250. In one embodiment, the gap is a longitudinally extending gap 250, which may be positioned adjacent to the posterior and/or rear aspect of the second dilator 200. The longitudinally extending gap may extend along the entire length of the second dilator or along only a portion of the second dilator. The longitudinally extending gap may extend along a majority of the axial length of the second dilator. The second dilator 200 further includes an inner wall 236 surface shape. In one embodiment, the inner wall surface cross-sectional shape of the second dilator is substantially similar to the exterior wall shape of the first dilator 100. The inner wall surface shape of the second dilator may be circular. The inner wall cross-sectional surface shape may have a perimeter that is interrupted by the gap 250. In one further embodiment, the interior wall 236 of the second dilator and the exterior wall 232 of the second dilator may be continuous and uninterrupted by the gap 250.

A longitudinal axis may extend generally perpendicularly through the center of the exterior wall 232 cross-sectional shape from the proximal end 210 of the second dilator to the distal end 220 of the second dilator 200. Yet another longitudinal axis may extend generally perpendicularly through the center of the interior wall 236 cross-sectional shape of the second dilator from the proximal end 210 of the second dilator to the distal end 220 of the second dilator 200. For example, the longitudinal axis may extend perpendicularly through the center of a circular interior wall 236 shape from the proximal end 210 of the dilator to the distal end 220 of the dilator 200.

The center or centroid of a two dimensional cross-sectional shape represents the point at which it could be balanced if it were cut out of a material of uniform mass, for example, sheet metal. The centroid of a circle or sphere, for example, is its geometric centre. More generally, the center or centroid of a two dimensional cross-sectional shape represents the point designated by the mean of the coordinates of all the points in a set. If the boundary is irregular, finding the mean requires using calculus (the most general formula for the centroid involves an integral).

Referring briefly now to FIG. 68, at least one additional method of defining a longitudinal axis as being centrally located with respect to a particular shape, resort may be made to an enveloping rectangle. This may be illustrated first for dilator 200. With respect to the gap 250, there may be drawn an imaginary line 290, that is tangent to the exterior wall 232 cross-sectional shape and that crosses the gap 250. Then, for the inner wall 236 surface shape, there may further be constructed an imaginary rectangle that uses imaginary line 290 as one of its sides and further comprises three additional sides 292a, 292b, 292c that are tangent to or envelope inner wall 236 surface shape. The diagonals of this rectangle may then be constructed as imaginary lines 296a, 296b. The intersection point of diagonals 296a, 296b may be intersection point 296c, which may be considered to be the center of inner wall 236 surface shape. Similarly, for the outer wall surface shape, which includes surfaces 242, 243, 244, there may be constructed an imaginary rectangle that uses imaginary line 290 as one of its sides and further comprises three additional sides 294a, 294b, 294c that are tangent to or envelope the outer wall surface shape. The diagonals of this rectangle may then be constructed as imaginary lines 298a, 298b. The intersection point of diagonals 298a, 298b may be intersection point 298c, which may be considered to be the center of the outer wall surface shape. It can be seen that intersection point 296c does not coincide with intersection point 298c. This may similarly be illustrated for dilator 300. With respect to the gap 350, there may be drawn an imaginary line 390, that is tangent to the exterior wall 332 cross-sectional shape and that crosses the gap 350. Then, for the inner wall 336 surface shape, there may further be constructed an imaginary rectangle that uses imaginary line 390 as one of its sides and further comprises three additional sides 392a, 392b, 392c that are tangent to or envelope inner wall 336 surface shape. The diagonals of this rectangle may then be constructed as imaginary lines 396a, 396b. The intersection point of diagonals 396a, 396b may be intersection point 396c, which may be considered to be the center of inner wall 336 surface shape. Similarly, for the outer wall surface shape, which includes surfaces 342, 343, 344, there may be constructed an imaginary rectangle that uses imaginary line 390 as one of its sides and further comprises three additional sides 394a, 394b, 394c that are tangent to or envelope the outer wall surface shape. The diagonals of this rectangle may then be constructed as imaginary lines 398a, 398b. The intersection point of diagonals 398a, 398b may be intersection point 398c, which may be considered to be the center of the outer wall surface shape. It can be seen that intersection point 396c does not coincide with intersection point 398c.

In at least one embodiment, the second dilator 200 interior wall 236 cross-sectional shape and the second dilator exterior wall 232 cross-sectional shape are eccentric to each other, wherein the second dilator's 200 interior wall cross-sectional shape central longitudinal axis and the second dilator's exterior wall shape central longitudinal axis are offset but parallel to each other. In at least one embodiment the second dilator interior wall cross-sectional shape may be positioned more proximate to the posterior rear aspect of the second dilator than to the anterior frontal aspect of the second dilator.

In yet additional embodiments, the inner wall surface 236 cross-sectional shape of the second dilator 200 may be other shapes than a circular shape. However, in at least one embodiment the inner wall surface shape 236 of the second dilator generally corresponds to and substantially mates with the exterior wall surface shape 132 of the first dilator 100. In at least one embodiment, the inner wall surface cross-sectional shape 236 of the second dilator 200 is a circle having a discontinuous perimeter interrupted by the longitudinal gap 250 and the exterior wall surface shape 132 of the first dilator 100 is a circle. The exterior wall surface circular shape of the first dilator may have a slightly smaller radius than the interior wall surface circular shape of the second dilator, wherein the second dilator's interior wall 236 may be slidingly advanced over and mate with the exterior wall 132 of the first dilator 100. In at least one embodiment, a portion of the exterior wall of the first dilator may extend into the gap in the second dilator. In yet an additional embodiment, a portion of the exterior wall of the first dilator may extend into and beyond the gap in the second dilator.

Referring more specifically now to FIG. 4, in one embodiment the second dilator 200 includes an anterior wall 242, which is elongated in transverse cross section and positioned proximate the anterior frontal aspect of the second dilator, and an opposing transversely elongated posterior wall 243, which is positioned proximate the posterior rear aspect of the second dilator, and may be interrupted by the longitudinally extending gap 250. The wall 230 of the second dilator further includes two lateral walls 244 that in at least one embodiment may be at least partially rounded or curvilinear in transverse cross section.

The second dilator 200 further includes a channel 240. In one embodiment, the inner wall 236 and the longitudinally extending gap 250 form the channel 240 within the second dilator 200. In one embodiment, the channel may include an opening formed by the longitudinally extending gap 250 in the elongated posterior wall 243. The channel 240 may be positioned more proximate to the posterior rear aspect of the second dilator 200 and less proximate to the anterior frontal aspect of the second dilator 200. The channel 240 of the second dilator 200 is sized and shaped to mate with and slidingly advance over the first dilator 100 exterior wall 132. The channel 240 of the second dilator 200 is configured to slidingly receive and engage at least a portion of a longitudinal length of the first dilator 100 therethrough. In yet another embodiment, the exterior wall 132 of the first dilator 100 may at least partially occlude a portion of the gap 250 in the wall 230 of the second dilator 200 when the first dilator is slidingly received within the channel 240 of the second dilator.

In yet another embodiment, the proximal end 210 of second dilator 200 may further include a grip surface 212, which may be advantageous in facilitating control of the second dilator 200 by a surgeon. In at least one embodiment the grip surface includes ring-like recesses formed in the exterior wall 232. The ring-like recesses may be engaged and held by a tool 800. In yet a further embodiment described in greater detail below, longitudinal electrical conducting members 260 are imbedded in the wall 230 of second dilator 200 and extend from an electrical conducting member proximal end 262 to an electrical conducting member distal end 264. In at least one embodiment, the distal end 220 of the second dilator 200 may include a tapered and/or a contoured distal exterior wall surface 234.

Referring again to FIGS. 1-6c, in one embodiment, the third dilator 300 includes a wall 330. In at least one embodiment an exterior wall 332 cross-sectional shape may be a generally oblong shape. In yet other embodiments the exterior wall shape 332 may be another shape, for example, a round, triangular, square, or multisided shape.

The exterior wall cross-sectional shape may have a perimeter that is interrupted by a gap 350. In one embodiment the gap is a longitudinally extending gap 350, which may be positioned adjacent to the posterior and/or rear aspect of the third dilator 300. The longitudinally extending gap may extend along the entire length of the third dilator or along only a portion of the third dilator. The longitudinally extending gap may extend along a majority of the axial length of the third dilator. The third dilator 300 further includes an inner wall 336 surface shape. In one embodiment, the inner wall surface cross-sectional shape of the third dilator 300 is substantially similar to the exterior wall shape of the second dilator 200. The inner wall surface shape of the third dilator may be oblong. The inner wall cross-sectional surface shape of the third dilator 300 may have a perimeter that is interrupted by the gap 350. In one further embodiment, the interior wall 336 of the third dilator and the exterior wall 332 of the third dilator may be continuous and uninterrupted by the gap 350.

A longitudinal axis may extend generally perpendicularly through the center of the exterior wall 332 cross section shape from the proximal end 310 of the third dilator 300 to the distal end 320 of the third dilator 300. Yet another longitudinal axis may extend generally perpendicularly through the center of the interior wall 336 cross-sectional shape of the third dilator 300 from the proximal end 310 of the third dilator 300 to the distal end 320 of the third dilator 300.

In at least one embodiment, the third dilator 300 interior wall 336 cross-sectional shape and the third dilator exterior wall 332 cross-sectional shape may be eccentric to each other, wherein the third dilator's 300 interior wall cross-sectional shape central longitudinal axis and the third dilator's exterior wall central longitudinal axis may be offset and parallel to each other. In at least one embodiment the third dilator interior wall cross-sectional shape may be positioned more proximate to the posterior rear aspect of the third dilator than to the anterior frontal aspect of the third dilator.

In yet additional embodiments, the inner wall surface 336 cross-sectional shape of the third dilator 300 may be other shapes than an oblong shape. However, in at least one embodiment the inner wall surface shape 336 of the third dilator is configured to generally correspond to and substantially mate with the exterior wall surface shape 232 of the second dilator 200. In at least one embodiment, the inner wall surface cross-sectional shape 336 of the third dilator 300 is an oblong shape having a discontinuous perimeter interrupted by the longitudinal gap 350 and the exterior wall surface shape 232 of the second dilator 100 is an oblong shape having a discontinuous perimeter interrupted by the longitudinal gap 350. The exterior wall surface cross-sectional shape of the second dilator may have a slightly smaller size than the interior wall surface cross-sectional shape of the third dilator, wherein the third dilator's 300 interior wall 336 may be slidingly advanced over the exterior wall 232 of the second dilator 200. In at least one embodiment, a portion of the exterior wall of the first dilator and/or second dilator may extend into the gap in the third dilator. In yet an additional embodiment, a portion of the exterior wall of the first dilator and/or second dilator may extend into and beyond the gap in the third dilator.

In one further embodiment, the inner surface shapes of at least one of the dilators and the exterior surface shapes of at least another of the dilators may be substantially identical. In one embodiment at least one longitudinal axis may extend generally perpendicular to at least one interior wall shape or at least one exterior wall shape may align with at least one other longitudinal axis extending generally perpendicular to at least one other interior wall shape or at least one exterior wall shape. For example, the dilators may have interior wall shapes that are round or partially round, exterior wall shapes that are round or partially round, and may slidingly assemble over each other concentrically or eccentrically.

Referring more specifically now to FIG. 4, in one embodiment the third dilator 300 includes an anterior wall 342, which is elongated in transverse cross section and positioned proximate the anterior frontal aspect of the third dilator, and an opposing transversely elongated posterior wall 343, which is positioned proximate the posterior rear aspect of the third dilator and may be interrupted by the longitudinally extending gap 350. The wall 330 of the third dilator further includes two lateral walls 344 that in at least one embodiment may be at least partially rounded or curvilinear in cross section.

With reference to FIGS. 4 and 4C, it is illustrated that dilator 300 may include on its external perimeter a straight-line segment 342. Dilator 300 may include on its internal perimeter a straight-line segment 336. External straight-line segment 342 may be parallel to internal straight-line segment 336, as illustrated. External straight-line segment 342 may have a length that is greater than the length of internal straight-line segment 336, as illustrated. It is possible that straight-line segment 342 may transition to lateral wall 344 by being tangent to lateral wall 344 in the manner of a racetrack shape. It is further illustrated that the gap 350 in dilator 300 may have a gap width W, which may be defined as a dimension of a largest object that can pass from an exterior region of the second dilator to an interior region of the second dilator, and the length of the external straight-line segment 342 may be longer than the gap width W.

The third dilator 300 further includes a channel 340. In one embodiment, the inner wall 336 and the longitudinally extending gap 350 form the channel 340 inside the third dilator 300. In one embodiment the channel may include an opening formed by the longitudinally extending gap 350 in elongated posterior wall 343. The channel 340 may be positioned more proximate to the posterior rear aspect of the third dilator 300 and less proximate to the anterior frontal aspect of the third dilator 300. The channel 340 of the third dilator 300 is sized and shaped to mate with and slidingly advance over the second dilator 200 exterior wall 232. The channel 340 of the third dilator 300 is configured to slidingly receive and engage at least a portion of a longitudinal length of the second dilator 200 therethrough. The walls of the first dilator 100 and/or the second dilator 200 may at least partially occlude a portion of the gap 350 in the wall 330 of the third dilator 300 when the first dilator 100 and second dilator 200 are slidingly received in the channel 340 of the third dilator 300. In yet another embodiment, uninterrupted anterior wall 242 of the second dilator 200 may be turned posteriorly to at least partially occlude the gap 350 in the posterior wall 343 of the third dilator 300. When the second dilator 200 is slidingly received in the channel 340 of the third dilator 300 with the gap 250 in the second dilator and the gap 350 in the third dilator facing in opposite directions, the gap 350 in the third dilator 300 may be at least partially occluded.

In yet another embodiment, the proximal end 310 of third dilator 300 may further include a grip surface 312, which may be advantageous in facilitating control of the third dilator 300 by a surgeon. In at least one embodiment the grip surface includes ring-like recesses formed in the exterior wall 332. The ring-like recesses may be engaged and held by a tool 800. In a further embodiment described in greater detail below, longitudinal electrical conducting members 360 are imbedded in the wall 330 of third dilator 300 and extend from an electrical conducting member proximal end 362 to an electrical conducting member distal end 364. In at least one embodiment, the distal end 320 of the third dilator 300 may include a tapered and/or contoured distal exterior wall surface 334.

Figure 53:
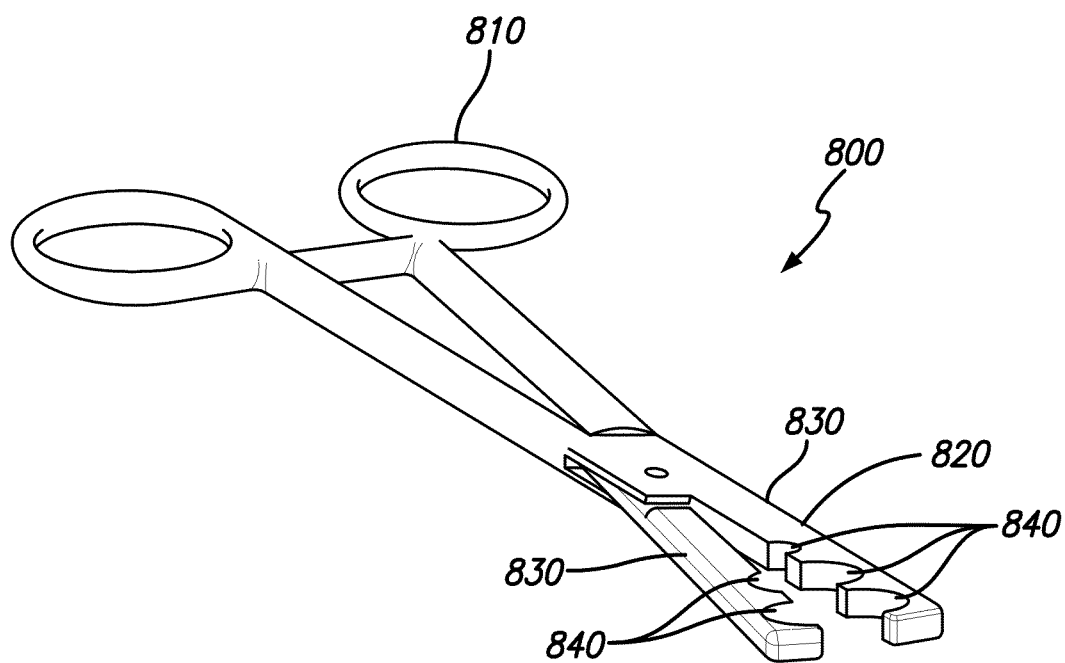
FIG. 53 is a perspective view of one embodiment of a dilator clamping tool.
Figure 54:
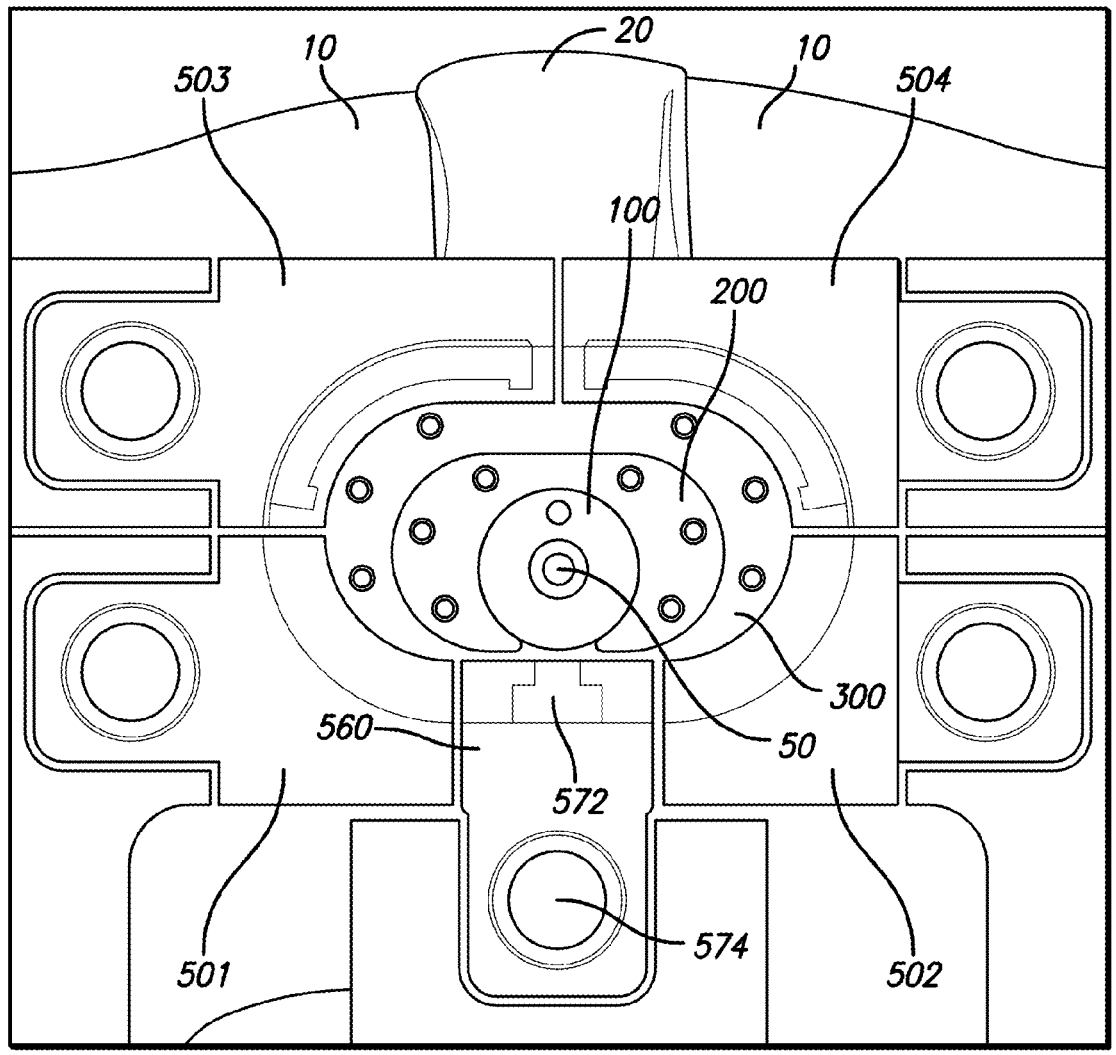
FIG. 54 is a top plan view of one embodiment of an assembly of an embodiment of the dilator system of the present invention and an embodiment of the retractor system of the present invention in a closed configuration positioned over a human spine.

Referring briefly now to FIG. 53, one embodiment of the invention includes a dilator clamping tool 800 configured to grip and manipulate the dilators 100, 200, 300. The clamping tool includes a proximal handle portion 810 and a distal clamping portion 820. The distal clamping portion 820 includes pivotably connected clamping arms 830. The clamping arms may include at least one recess 840 that is sized and shaped to mate with at least a portion of the exterior wall surface of at least one of the dilators 100, 200, 300. At least one embodiment of the clamping tool 800 includes recesses 840 having varying sizes and/or shapes, which are configured to mate with the sizes and shapes of the various exterior walls of the dilators. The clamping tool 800 may be used to grip and/or manipulate at least one of the first dilator 100, the second dilator 200, and/or the third dilator 300. At least one embodiment of the clamping tool 800 includes clamping arms 830 made from a radiolucent material to aid in visualization under fluoroscopy.

Figure 5:
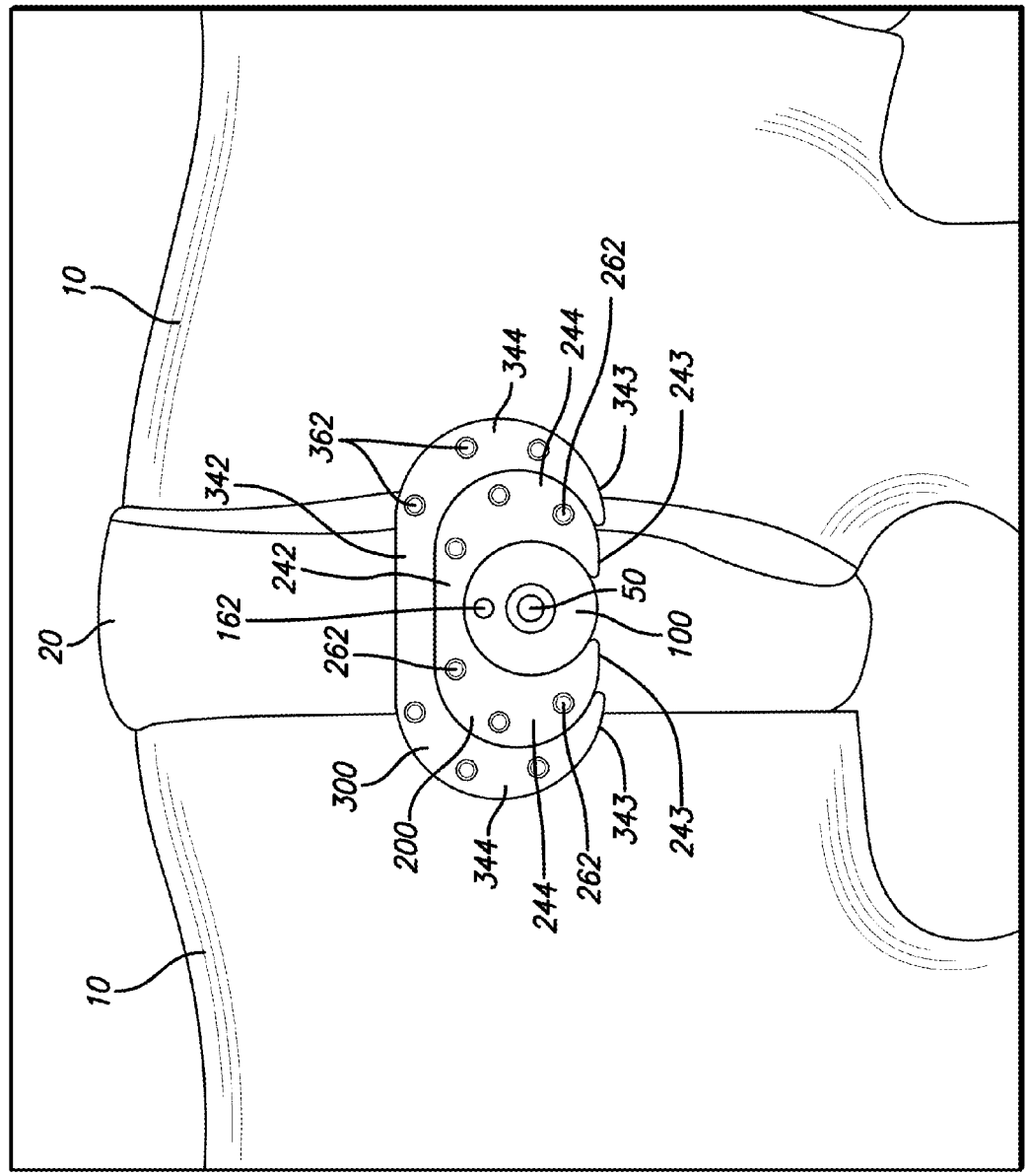
FIG. 5 is top plan views of the first dilator, the second dilator, and the third dilator of the dilator system of FIG. 1 assembled over a disc space and two adjacent vertebral bodies.

Referring more specifically now to FIGS. 4 and 5, at least one advantage of the dilator system 40 of the present invention is the differential dilation of tissues in at least one direction that is transverse to the longitudinal axis of the first dilator 100 or guidewire 50. Following placement of first dilator 100, the second dilator 200 is slidingly positioned over the first dilator and advanced towards the spine. In at least one embodiment, the channel 240 in the second dilator 200 is disposed proximate to the posterior rear aspect of the second dilator and towards the longitudinally extending gap 250 in the elongated posterior wall 243. In one embodiment, when the first dilator and the second dilator are slidingly engaged together, a central longitudinal axis perpendicular to the exterior wall shape of the first dilator may be posteriorly displaced, towards the gap 250, relative to a central longitudinal axis perpendicular to the exterior wall shape of the second dilator. In at least one embodiment, when the second dilator's channel 240 is mated about the first dilator, the first dilator will be positioned more proximate to the posterior rear aspect of the second dilator, thereby resulting in a differentially greater anterior directed dilation of soft tissues by the second dilator.

The off-center positioning of the channel 240 towards the posterior wall 243 of the second dilator 200 provides dilation of tissues predominantly in a direction towards the anterior frontal aspect anterior wall 242 of second dilator 200. Furthermore, the gap 250 in the posterior wall 243 of the second dilator minimizes or eliminates the dilation of tissues in a direction towards the posterior rear aspect of second dilator 200. An oblong exterior wall 232 shape of the second dilator 200 may additionally provide a greater dilation of soft tissues in a lateral wall direction compared to a dilation of soft tissues in an anterior and/or posterior direction. In still an additional embodiment, the second dilator 200 includes lateral walls 244 that are thicker than the anterior wall 242, wherein transverse tissue dilation in an anatomically rostral and/or anatomically caudal direction may be maximized compared to anatomically posterior dilation of tissues.

The longitudinal extending gap 250 in the posterior wall 243 interrupting the perimeter of the shape of the exterior wall of the second dilator 200 is beneficial in minimizing directional dilation of soft tissues towards the gap. In at least one embodiment, when the first dilator 100 is slidingly engaged within the channel of the second dilator 200, the longitudinally extending gap is at least partially occluded by the exterior wall of the first dilator 100. In at least one embodiment, the posterior wall of the second dilator does not extend beyond the exterior wall of the first dilator. Therefore, when the second dilator is slidingly advanced over the first dilator, the configuration of the second dilator minimizes or eliminates dilation of soft tissue towards the posterior rear aspect of the second dilator relative to the first dilator's 100 exterior wall 132.

Still referring to FIGS. 4 and 5, in at least one embodiment a third dilator 300 is provided that may be slidingly engaged over and/or about the second dilator 200 exterior wall 232 and advanced towards the spine. The exterior wall surface 232 of the second dilator 200 is sized and shaped to slidingly mate with an inner wall surface 336 and channel 340 of a third dilator 300, as the third dilator 300 is slidingly advanced over the second dilator 200. In one embodiment, the channel 340 of the third dilator 300 is positioned more proximate to the posterior rear aspect of the third dilator and towards the longitudinally extending gap 350 in the elongated posterior wall 343. The channel 340 is positioned more proximate to the posterior rear aspect of the third dilator than to the anterior frontal aspect of the third dilator. In one embodiment, when the second dilator and the third dilator are slidingly engaged together, the central longitudinal axis may extend perpendicularly to the exterior wall shape of the second dilator is posteriorly displaced relative to a central longitudinal axis extending perpendicularly to the exterior wall shape of the third dilator. In one embodiment, when the third dilator channel is slidingly mated about the second dilator, the second dilator is positioned more proximate to the posterior rear aspect of the third dilator than to the anterior frontal aspect of the third dilator. Dilation of tissues may thereby be minimized in a direction towards the posterior wall 343 of third dilator 300. Dilation of tissues may be minimized towards the posterior rear aspect of the third dilator. Dilation may be provided relatively greater anteriorly than posteriorly. An oblong shape of third dilator 300 may additionally provide greatest dilation of soft tissues adjacent to the lateral walls 344 of the third dilator 300. In yet an additional embodiment, the third dilator 300 lateral walls 344 are thicker than anterior wall 342, wherein transverse tissue dilation is maximized in an anatomically rostral and/or anatomically caudal direction relative to the intervertebral body disc space 20.

In one embodiment there may be a longitudinal extending gap 350 in the posterior wall 343. The gap may be disposed in the posterior rear aspect of the third dilator, wherein it interrupts the perimeter of the shape of the exterior wall of the third dilator 300. The longitudinal gap 350 in the posterior rear aspect of the third dilator is beneficial in minimizing directional dilation of soft tissues in a posterior rear aspect direction. When the first dilator 100 and second dilator 200 are slidingly engaged within the channel 340 of the third dilator 200, the longitudinally extending gap in the third dilator may be at least partially filled in by the exterior walls of the first dilator 100 and the second dilator 200. In at least one embodiment, the posterior wall of the third dilator does not extend beyond the most posteriorly positioned portion of the exterior wall 132 of the first dilator 100 and/or the second dilator 200. In at least one embodiment posterior directional dilation of soft tissue is thereby minimized or eliminated.

At least one additional embodiment, FIG. 5, of the dilator system 40 may provide greater dilation in a lateral wall 244, 344 direction relative to dilation provided in an anterior wall 242, 342 direction. Still another embodiment, FIGS. 56-59, may have a thicker anterior wall and may provide lesser dilation in a lateral wall 244, 344 direction relative to dilation provided in an anterior wall 242, 342 direction. Some embodiments, FIGS. 1-5 and 56-59, of the dilator system may provide greater dilation in a lateral wall 244, 344 direction relative to dilation provided in a posterior wall 243, 343 direction. At least one embodiment of the dilator system may provide greater dilation in an anterior wall 242, 343 direction relative to the dilation provided in a posterior wall 243, 343 direction because of the eccentric positioning of a channel 240, 340 in the dilators 200, 300. The longitudinal gap 250, 350 in the posterior wall 243 343 further positions the channels 240, 340 posteriorly in the dilators 200, 300 and thereby minimizes the dilation of soft tissues in the posterior wall 243, 343 direction. However, in yet another embodiment, instead of a gap 250, 350, a posterior wall 243, 343 that is significantly thinner than an anterior wall 242, 343 may be provided to reduce dilation in a posterior direction relative to dilation in an anterior direction.

In some embodiments, at least one of the exterior wall of the second dilator 200 and/or the exterior wall of third dilator 300 may not be oblong. For example, in one embodiment the exterior wall 132 shape of the first dilator 100, the exterior wall 232 shape of the second dilator 200, and the interior wall 236 shape of the second dilator 200 may all have a substantially circular cross-sectional shape. The second dilator 200 and the third dilator 300 may have a longitudinal gap 250, 350 interrupting the periphery of the interior wall 236, 336 circular cross-sectional shape and the exterior wall 232, 332 cross-sectional shape. The central longitudinal axis of the generally circular shaped inner wall channel 240 of the second dilator may be displaced posteriorly towards the gap 250 in the second dilator. The periphery of the generally circular cross-sectional shape of the interior wall 236 of the second dilator 200 may touch or cross the periphery of the generally circular cross-sectional shape of the exterior wall 232 of the second dilator 200. The central longitudinal axis extending perpendicularly to the generally circular shaped inner wall channel 340 of the third dilator 300 may be displaced towards the gap 350 in the third dilator 300. The periphery of the circular cross-sectional shape of the interior wall 336 of the third dilator 300 may touch or cross the periphery of the circular cross-sectional shape of the exterior 332 wall of the third dilator 300. In at least one embodiment the posteriorly eccentric positioned circular channels 240, 340 in a second dilator and/or in a third dilator are advantageous in that a plurality of different directional dilations about the central longitudinal axis of the first dilator 100 may be achieved by a surgeon by rotating the second dilator 200 about a first cylindrical dilator 100 and/or by rotating the third dilator 300 about a second cylindrical dilator. In yet additional embodiments, more than three dilators may be provided. In at least one additional embodiment, the first dilator and the second dilator may have a generally cylindrical outer wall and the third dilator may have a generally oblong shaped exterior wall.

One embodiment of the present dilator system 40 includes a first dilator 100, and a second dilator 200. The first dilator 100 may be generally cylindrical. The second dilator 200 may be generally oblong. The first dilator 100 may have a lumen 140 configured to receive a guidewire 50 therethrough. In at least one embodiment, the first dilator may have a generally circular exterior periphery defined by the first dilator's exterior wall 132. The second dilator 200 may be troughlike in configuration may include an open proximal end 210 and/or an open distal end 220. In at least one embodiment, the channel 240 and opening 250 forming the trough may be positioned proximate the posterior rear aspect of the second dilator 200. The second dilator may include an inner channel 240 having an opening or longitudinal gap 250 between a left side portion and a right side portion of a posterior wall 243. The left and right sides of the posterior walls 243 of the second dilator may be close enough to each other to entrap the first dilator within the troughlike channel 240 and thereby prevent the first dilator 100 from dislodging out of the channel 240 through the gap 250.

Alternative configurations known in the art may be provided for aligning, mating, guiding, and/or locking at least one dilator within at least one other dilator's troughlike channel 240, 340. For example, variously shaped projections in one dilator wall may insert into a corresponding recess in at least one other dilator wall to provide aligning, mating, guiding, and/or locking of two or more dilators. Such projections and recesses provided for mating, guiding, and/or locking one dilator to another may include but are not limited to tongue and groove or dovetail joint configurations. The aligning, mating, guiding, and/or locking may therefore be accomplished without the need for an enveloping posterior wall 243, 343.

An exterior periphery of the second dilator is defined in part by an exterior wall 232 of the second dilator. Additionally, the exterior periphery of the second dilator 200 extends as an imaginary line across the gap 250 and generally follows the contour of the posterior wall's 243 exterior wall 232. The inner channel 240 of the second dilator 200 is sized and configured to slidingly mate over the exterior wall 132 of the first dilator. In at least one embodiment, when the second dilator channel 240 is slidingly mated over the first dilator 100, a portion of the exterior wall 132 of the first dilator 100 may extend posteriorly at least to the most posterior rear aspect exterior periphery of the second dilator 200. In yet another embodiment, when the second dilator channel 240 is slidingly mated over the first dilator 100, a portion of the exterior wall 132 of the first dilator 100 may extend posteriorly beyond the most posterior exterior periphery of the second dilator 200. Therefore, when the second dilator 200 channel 240 is slidingly advanced over the first dilator 100, the second dilator 200 does not provide any substantial posterior dilation at its posterior wall 243 relative to the most posteriorly positioned portion of the exterior wall 132 of the first dilator.

In yet another embodiment, the present dilator system 40 further includes at least one additional dilator. The at least one additional dilator 300 may be troughlike in configuration and may include an open proximal end 310 and/or an open distal end 320. The at least one additional dilator may include an inner channel 340 having an opening or longitudinal gap 350 between a left side and a right side portions of a posterior wall 343. In at least one embodiment, the trough, including a channel 340 and an opening 350, is disposed more adjacent to or proximate the posterior rear aspect of the third dilator 300 than the anterior frontal aspect of the third dilator 300. The left and right sides of the posterior walls 343 of the at least one additional dilator may be close enough to each other and prevent the second dilator in the channel 340 and prevent the second dilator 200 from dislodging out of the channel 340 through the gap 350. Alternative configurations known in the art may be used to lock the second dilator within the additional dilator's troughlike channel. An exterior periphery of the at least one additional dilator 300 is defined in part by an exterior wall 332 of the at least one additional dilator 300. Additionally, the exterior periphery of the at least one additional dilator extends as an imaginary line across the gap 350 of the at least one additional dilator 300 and generally follows the contour of the posterior wall's 343 exterior wall 332. The inner channel 340 of the at least one additional dilator 300 is sized and configured to slidingly mate over the exterior wall 232 of the second dilator 200. In at least one embodiment, when the at least one additional dilator channel 340 is slidingly mated over the second dilator 200 with the first dilator 100 within the second dilator channel 240, a portion of the exterior wall 132 of the first dilator 100 extends posteriorly at least to the most posterior exterior periphery of the at least one additional dilator 300. In yet another embodiment, when the at least one additional dilator channel 340 is slidingly mated over the second dilator 200 with the first dilator 100 within the second dilator channel 240, a portion of the exterior wall 132 of the first dilator 100 extends posteriorly beyond the most posterior exterior periphery of the at least one additional dilator 300. Therefore, when the at least one additional dilator 300 channel 340 is slidingly advanced over the first dilator 100 and the second dilator 200, the at least one additional dilator 300 does not provide any substantial posterior dilation at its posterior wall 343 relative to the most posteriorly positioned portion of the exterior wall 132 of the first dilator 100 and/or the most posteriorly positioned portion of the exterior wall 232 of the second dilator 200. It should be understood that the dilator system is not limited to only three dilators and that yet additional dilators may be provided.

Figure 6:
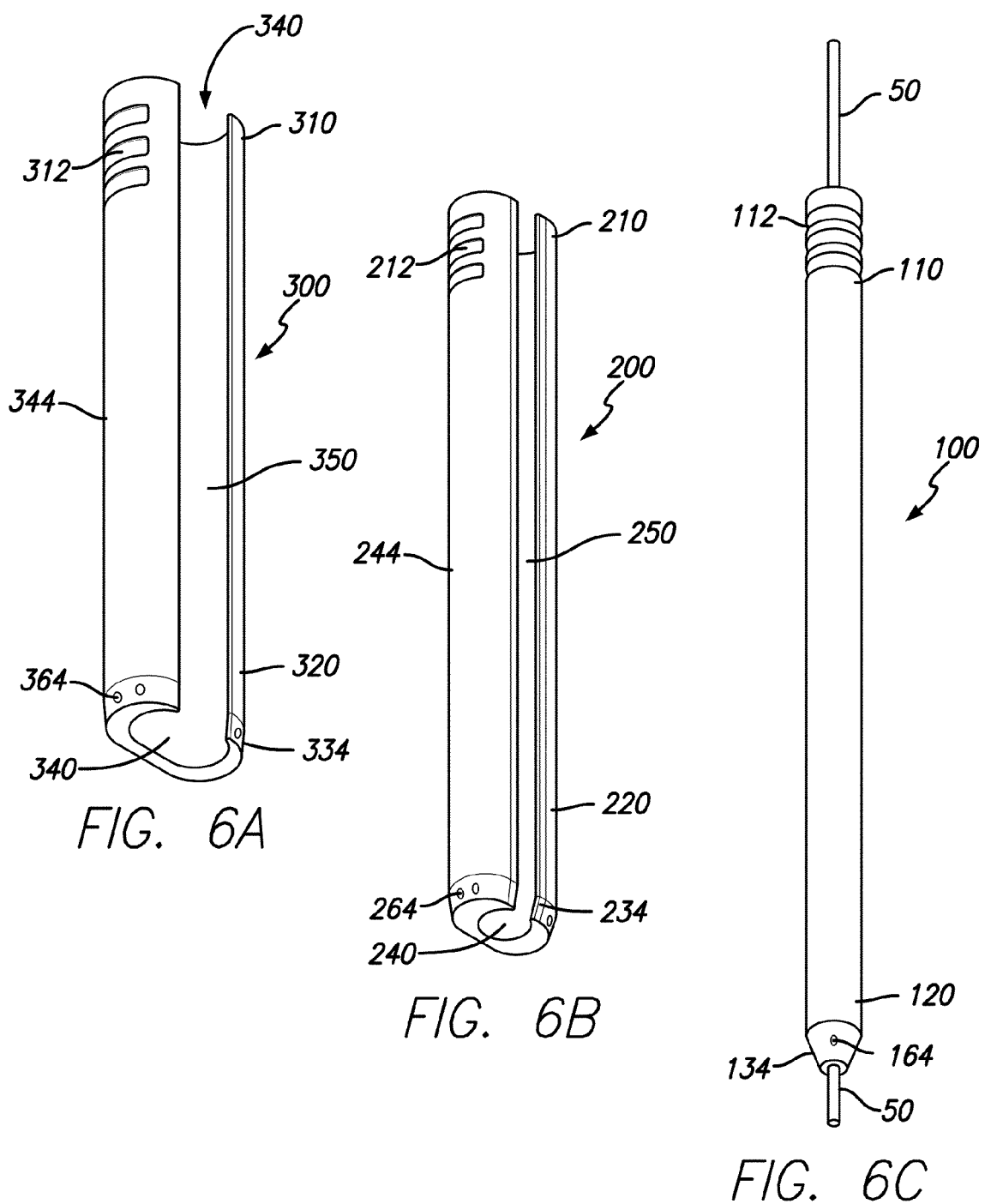
FIGS. 6A-6C are perspective views of the third dilator, the second dilator, and the first dilator, respectively, of the dilator system of FIG. 2.

Referring more specifically now to FIG. 4A as well as to FIGS. 1-6c, in at least one embodiment the dilator system 40 includes at least one longitudinal electrical conducting member 160, 260, 360 imbedded in a wall 130, 230, 330 of each one of the dilators 100, 200, 300. In one embodiment the electrical conducting members 160, 260, 360 extend generally the full length of the dilators, from the proximal ends 110, 210, 310 of the dilators to the distal ends 120, 220, 320 of the dilators. In yet other embodiments, the electrical conducting members 160, 260, 360 may extend less than the full length of the dilators. In at least one embodiment the electrical conducting members 160, 260, 360 are exposed at the proximal ends 110, 210, 310 of the dilators. Referring more specifically now to FIGS. 6A-6C, in one embodiment at least one of the distal ends of the electrical conducting member 164, 264, 364 is exposed on the tapered and/or contoured distal end 120, 220, 320 of the dilator 100, 200, 300. Although first dilator 100 is illustrated in FIGS. 1-6c with only one longitudinal electrical conducting member 160, it is to be understood that in yet other embodiments first dilator 100 may have a plurality of electrical conducting members. Although second dilator 200 and third dilator 300 are illustrated in FIGS. 1-6c with a plurality of longitudinal electrical conducting members 260, 360 it is to be understood that in yet other embodiments the second dilator 200 and third dilator 300 may have a fewer or greater number of electrical conducting members. In yet additional embodiments, at least one of the dilators may not have electrical conducting members 160, 260, 360.

In at least one embodiment, the electrical conducting members 160, 260, 360 may be used as nerve stimulation electrodes. The electrical conducting members 160, 260, 360 may be formed from stainless steel and/or other metals and/or other electrical conducting material. One or more of the electrical conducting member proximal ends 162, 262, 362 may be configured to be electrically stimulated by the surgeon.

The electrical stimulation may be conducted distally along the length of the stimulated electrical conducting member to the stimulated electrical conducting member distal end 164, 264, 364, wherein the electrical stimulation may enter into the tissues of a patient from the distal electrode 164, 264, 364. If a stimulated distal end 120, 220, 320 of at least one dilator is near one or more nerves innervating muscle, a monitored triggered EMG response may be evoked and interpreted by medical providers, for example the surgeon, indicating proximity of at least one dilator 100, 200, 300 to a patient's nerve tissue. In yet other embodiments, the electrical conducting members 160, 260, 360 may be used as sensing electrodes rather than stimulating electrodes. Electrical activity within a patient's nerve tissue at a distal electrode 164, 264, 364 of one or more of the dilators may be sensed at an electrical conducting member's proximal end 162, 262, 362. In at least one other embodiment, the electrical conducting members 160, 260, 360 may be used for unipolar or bipolar electrocoagulation of tissues. In further embodiments, radiopaque longitudinal members 160, 260, 360 may be used as radiological markers. Electrical conducting longitudinal members 160, 260, 360 may also be used as radiological markers without using them for electrical stimulation or neuromuscular monitoring. If the longitudinal members 160, 260, 360 are used solely as radiological markers without using them for electrical stimulation or for neuromuscular monitoring, the longitudinal members 160, 260, 360 may be formed of radiopaque material that is not an electrical conductor. One or more of the longitudinal members may extend less than the full length of one or more of the dilators.

Figure 60:
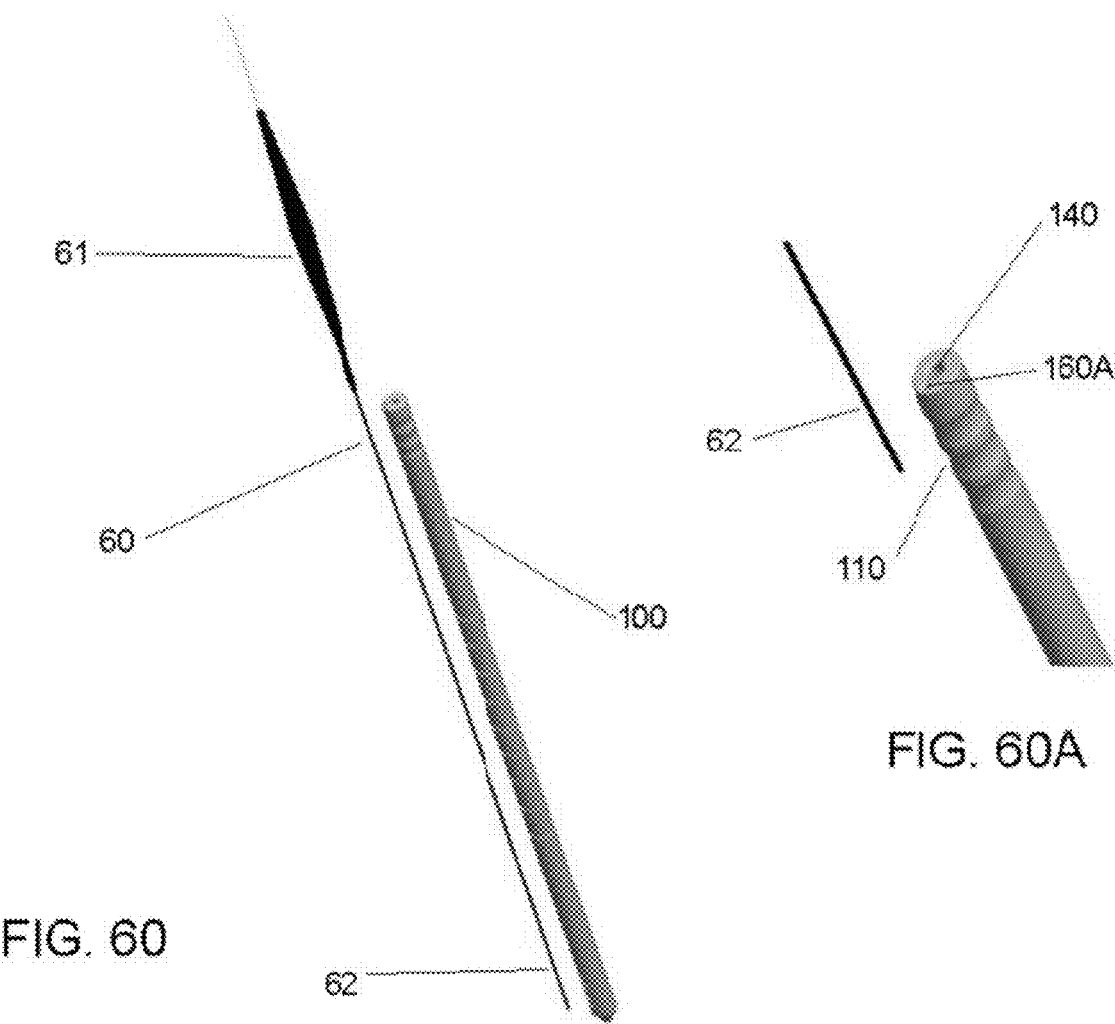
Figure 61:
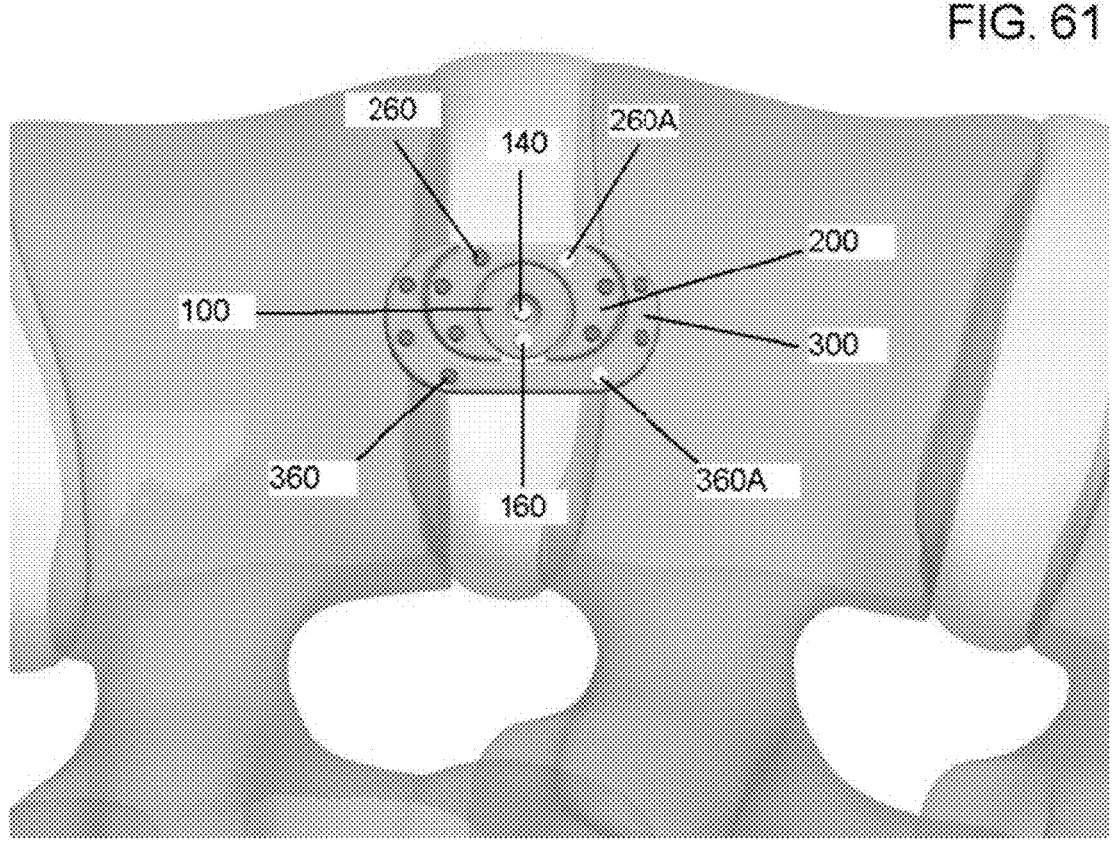
FIG. 61 is a top plan view of one embodiment of an assembly of the dilator system of the present invention positioned over a human spine.
Figure 62:
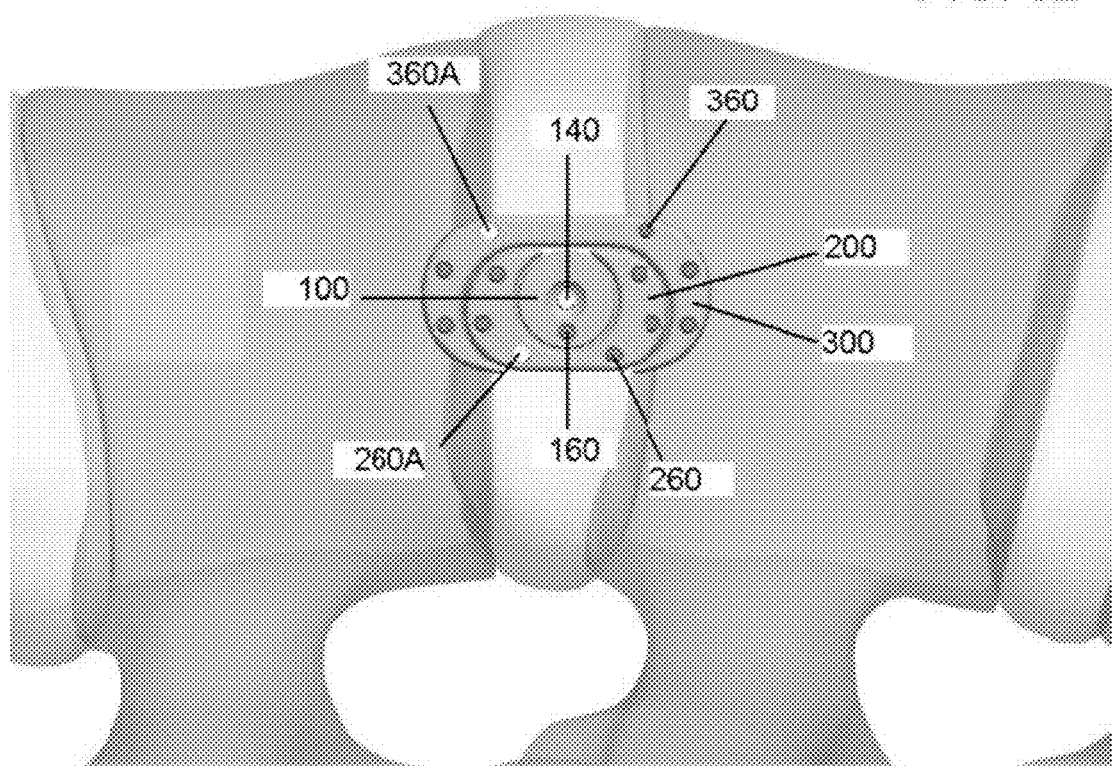
FIG. 62 is a top plan view of one embodiment of an alternative assembly of the dilator system of FIG. 61.

Referring briefly now also to FIGS. 60-62, in yet another embodiment, all or some of the electrical conducting members 160, 260, 360 may be replaced by one or more eccentric lumens, 160A, 260A, 360A extending longitudinally through the walls 130, 230, 330. At least one eccentric lumen may extend from a proximal end 110, 210, 310 of at least one of the first dilator 100, the second dilator 200, and/or the third dilator 300. At least one eccentric lumen may extend all of the distance or a portion of the distance from the proximal end 110, 210, 310 to approximately a distal end 134, 234, 334 of at least one of the first dilator, the second dilator, and/or the third dilator. In one embodiment, the eccentric lumen 160A is positioned within the wall 130, 230, 330 and may be configured to permit instrumentation, for example neuromonitoring instrumentation and/or other electrical instruments, to be introduced longitudinally into the eccentric lumen at the proximal end of at least one dilator and through the eccentric lumen to the distal ends of the at least one dilator. In at least one embodiment, instruments may be passed through the eccentric lumen 160A from the proximal end of at least one dilator to or beyond the distal end of the dilator. In yet another embodiment, at least one instrument may be passed through at least one eccentric lumen 160A from the distal end of at least one dilator to or beyond the proximal end of the dilator. In at least one embodiment, an exemplary neuromonitoring probe 60 may include a proximal end 61 and a distal end 62. The distal end 62 of the probe 60 may be configured to be slidingly inserted through at least one eccentric lumen 160A, 260A, 360A and used for nerve stimulation or nerve sensing at the distal end 134, 234, 334 of at least one dilator 100, 200, 300. Referring more specifically now to FIGS. 60 and 60A, in at least one embodiment, first dilator 100 includes a central lumen 140 and an eccentric center lumen 160A. The eccentric lumen may accommodate the passage of a distal end 62 of neuromonitoring probe 60 therethrough. In yet another embodiment, the probe 60 may be inserted through central lumen 140.

For any particular dilator, the off-centeredness of a dilator may be defined as the distance between the center of the inner wall and the center of the outer wall, as discussed in connection with FIG. 68. In FIGS. 1, 5, 54, 56, it is illustrated that dilators 100, 200 and 300 may be assembled in a configuration that may be referred to as a cumulative configuration, such that an off-centeredness of the second dilator and an off-centeredness of the third dilator cumulatively add to each other in a defined direction relative to the first dilator. In FIGS. 61 and 62, it is illustrated that dilators 100, 200 and 300 may be assembled in a configuration that may be referred to as a non-cumulative configuration, such that the off-centeredness of the second dilator and the off-centeredness of said third dilator do not cumulatively add to each other in a defined direction relative to the first dilator. The numerical magnitude of the off-centeredness of dilator 200 can be either greater than, less than or equal to the numerical magnitude of the off-centeredness of dilator 300. It can be observed that, as illustrated, when the first, second and third dilators are assembled in the non-cumulative configuration and an envelope of the third dilator is defined by extending a straight line across the gap of the third dilator such that the straight line is tangent to the external surface of the third dilator at each side of the gap, the second dilator may be contained entirely within the envelope of the third dilator. Similarly, the first dilator may be contained entirely within the envelope of the second dilator.

Figure 49:
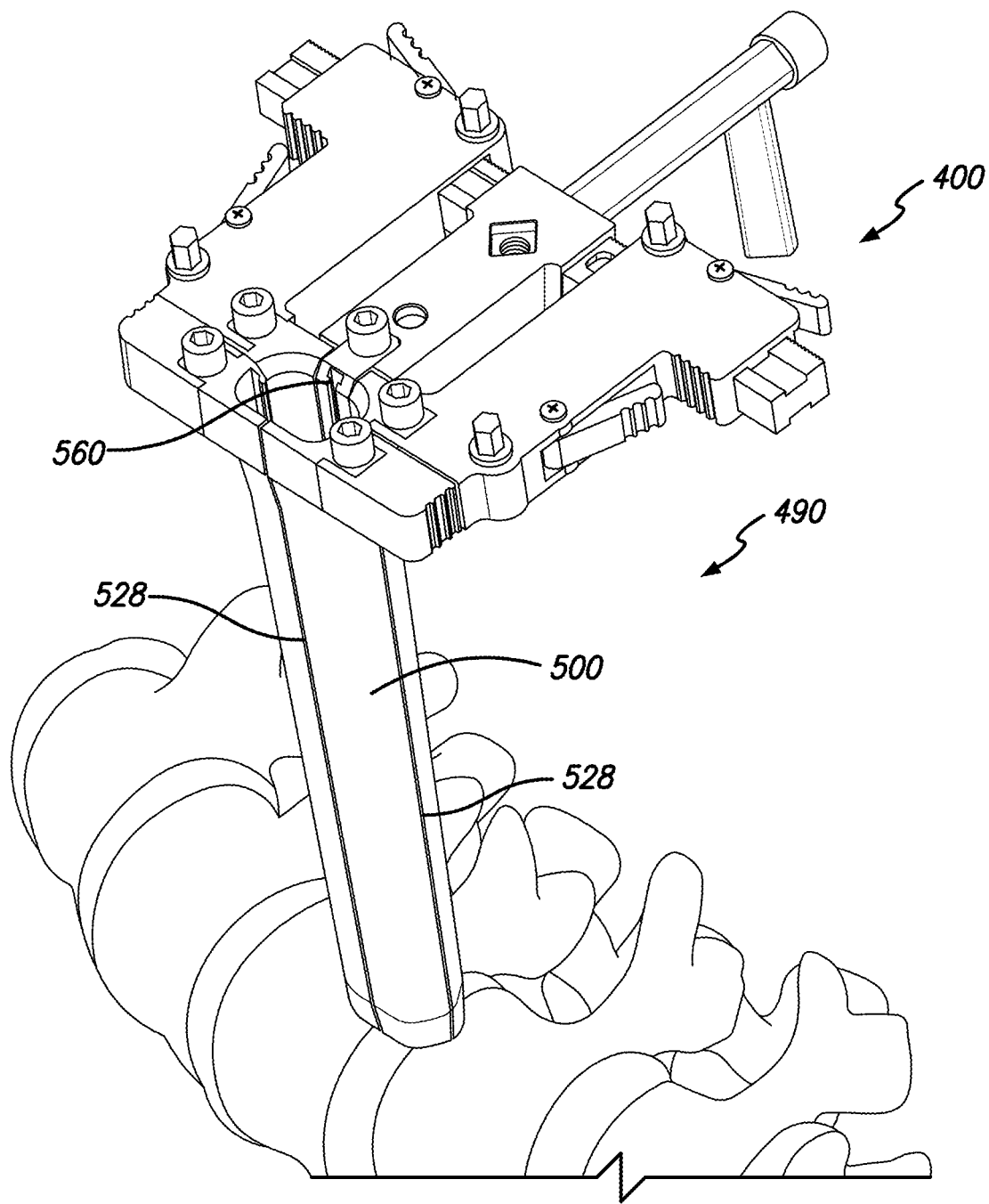
FIG. 49 is a perspective view of one embodiment of the retractor system of the present invention in a closed configuration.
Figure 50:
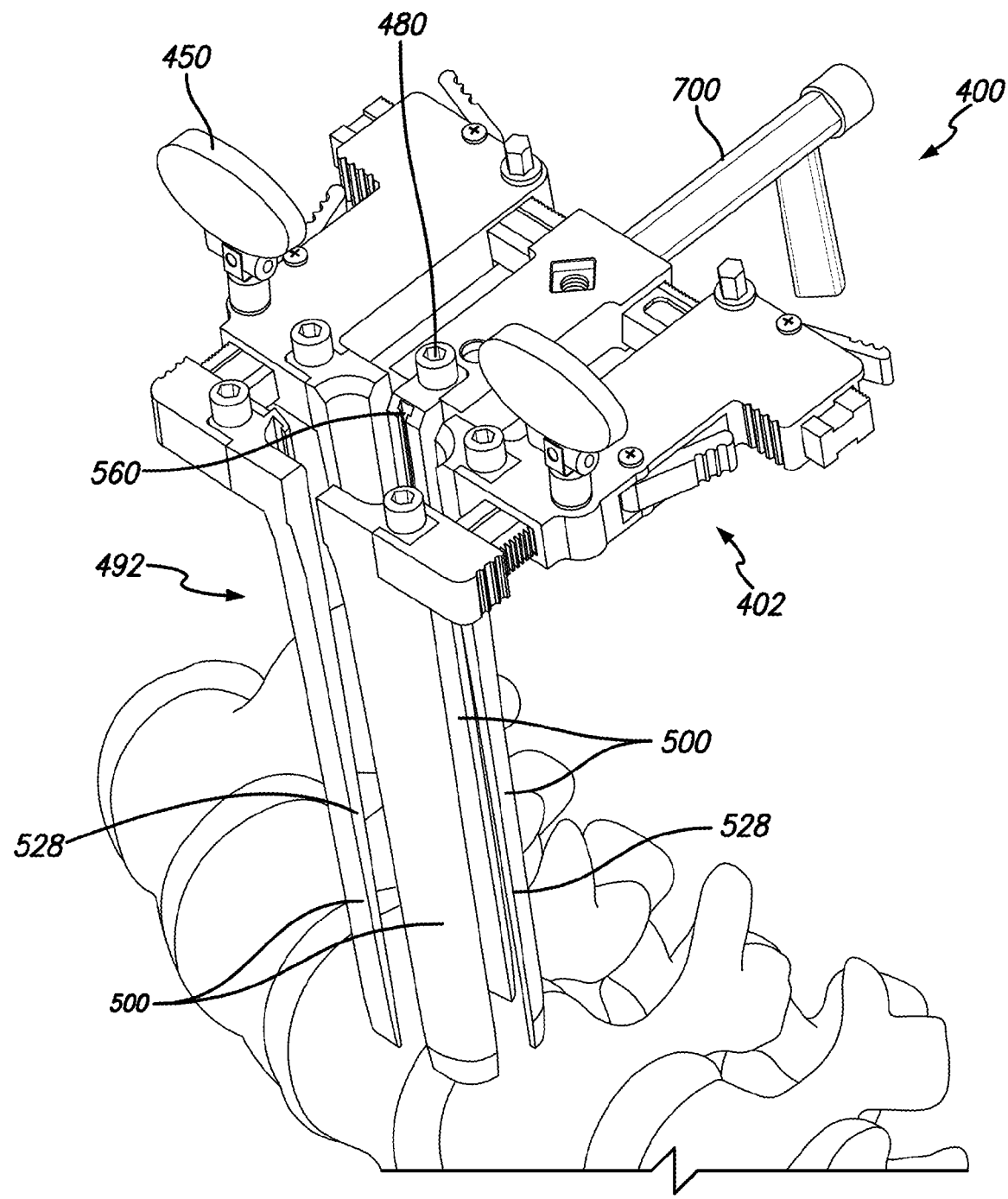
FIG. 50 is a perspective view of the retractor system of FIG. 49 in an open configuration.
Figure 51:
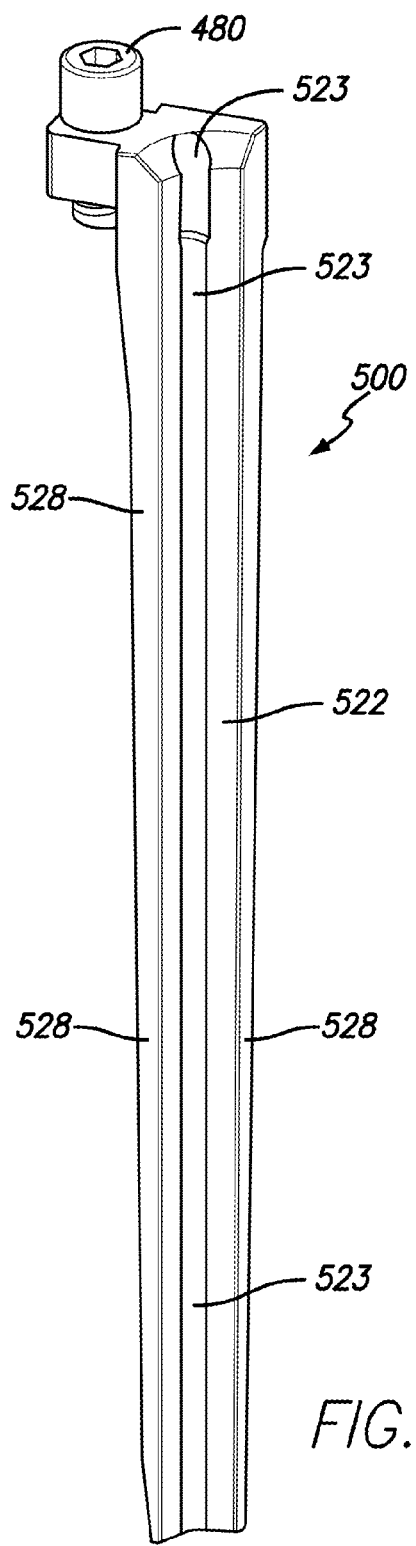
FIG. 51 is an inner perspective view of another embodiment of a primary blade having an anchor pin channel.
Figure 55:
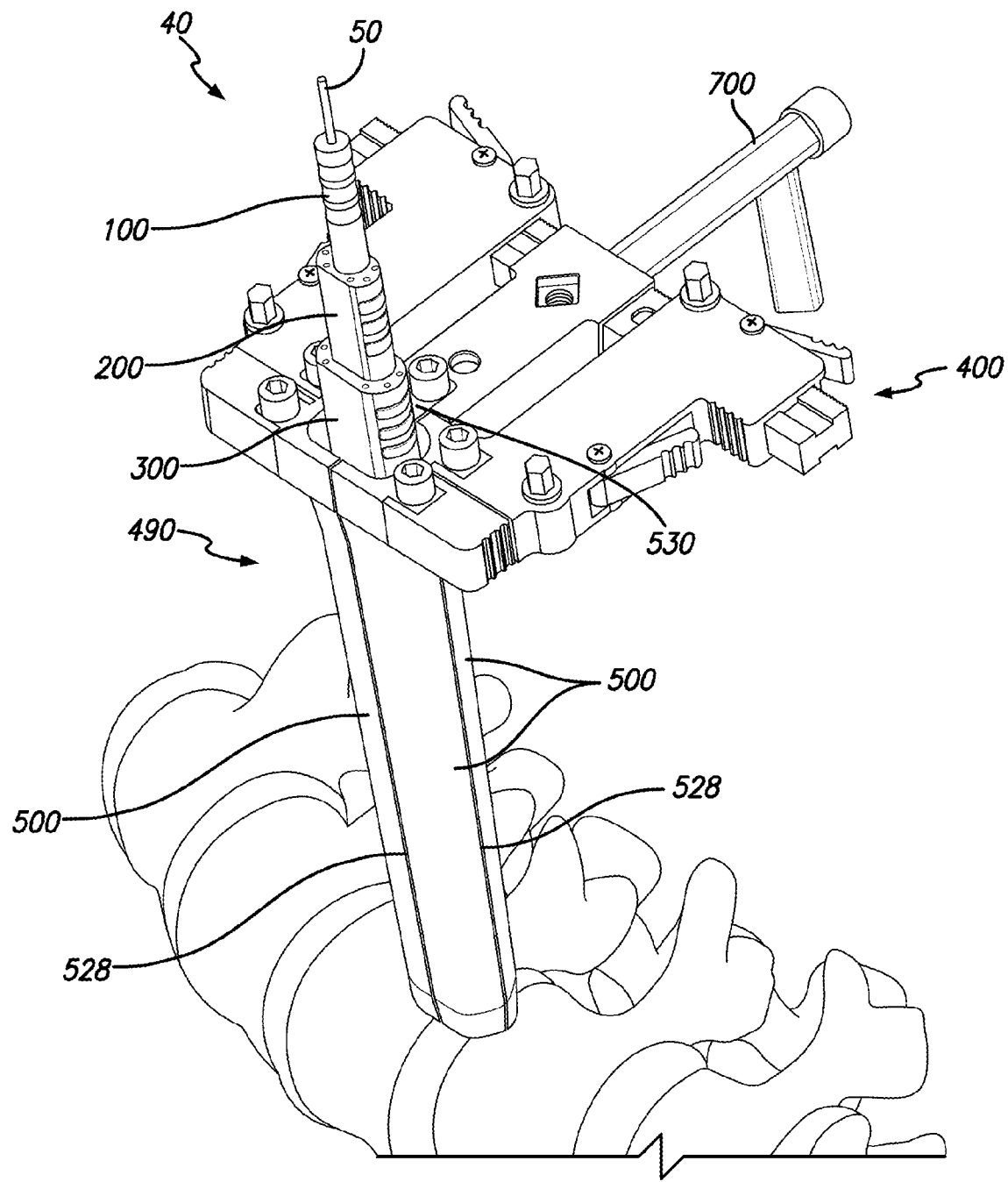
FIG. 55 is an anterior right sided perspective view of one embodiment of an assembly of an embodiment of the dilator system of the present invention and an embodiment of the retractor system of the present invention in a closed configuration positioned over a human spine.
Figure 56:
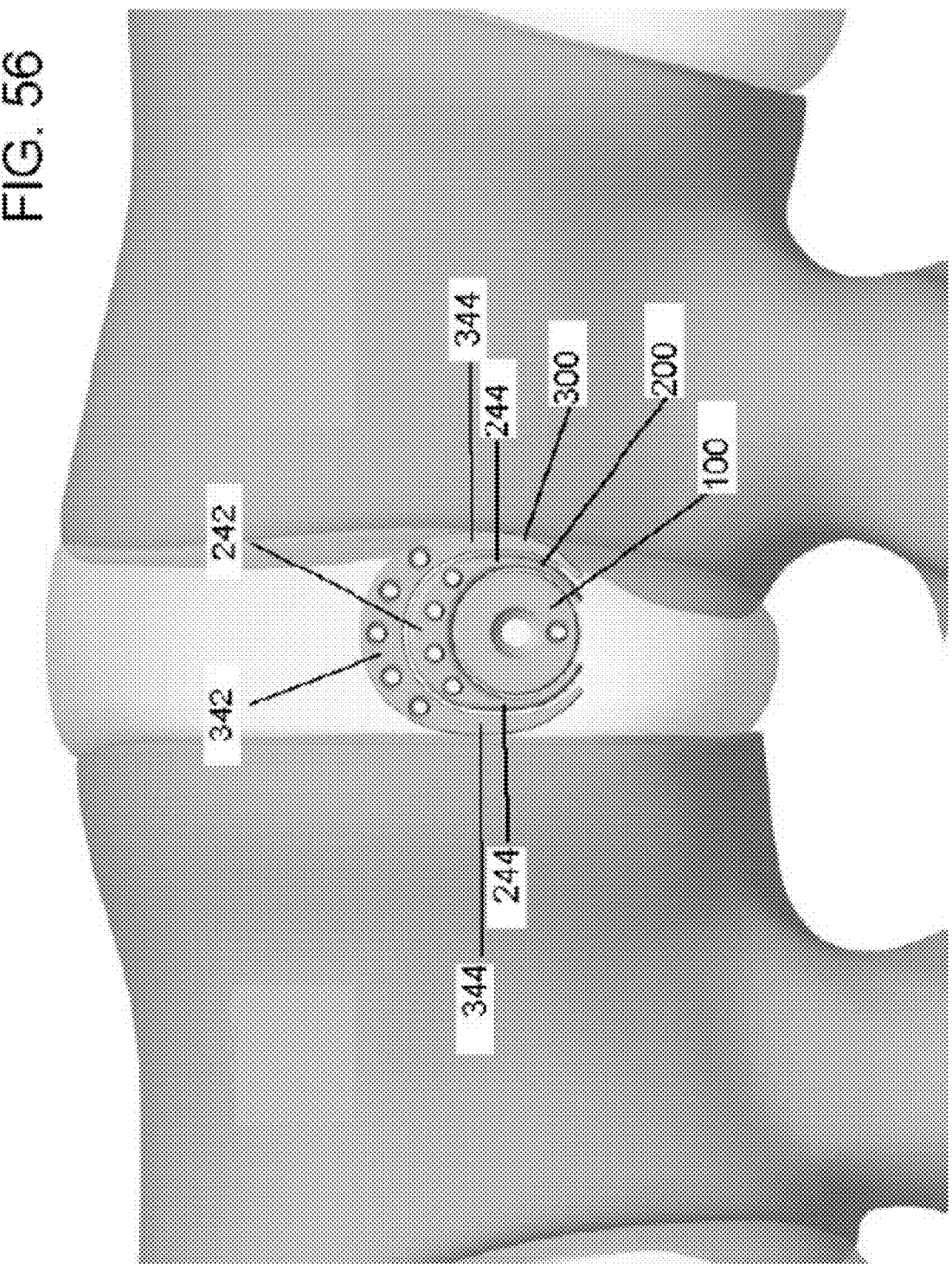
FIG. 56 is top plan view of one embodiment of an assembly of the dilator system of the present invention positioned over a human spine.
Figure 57:
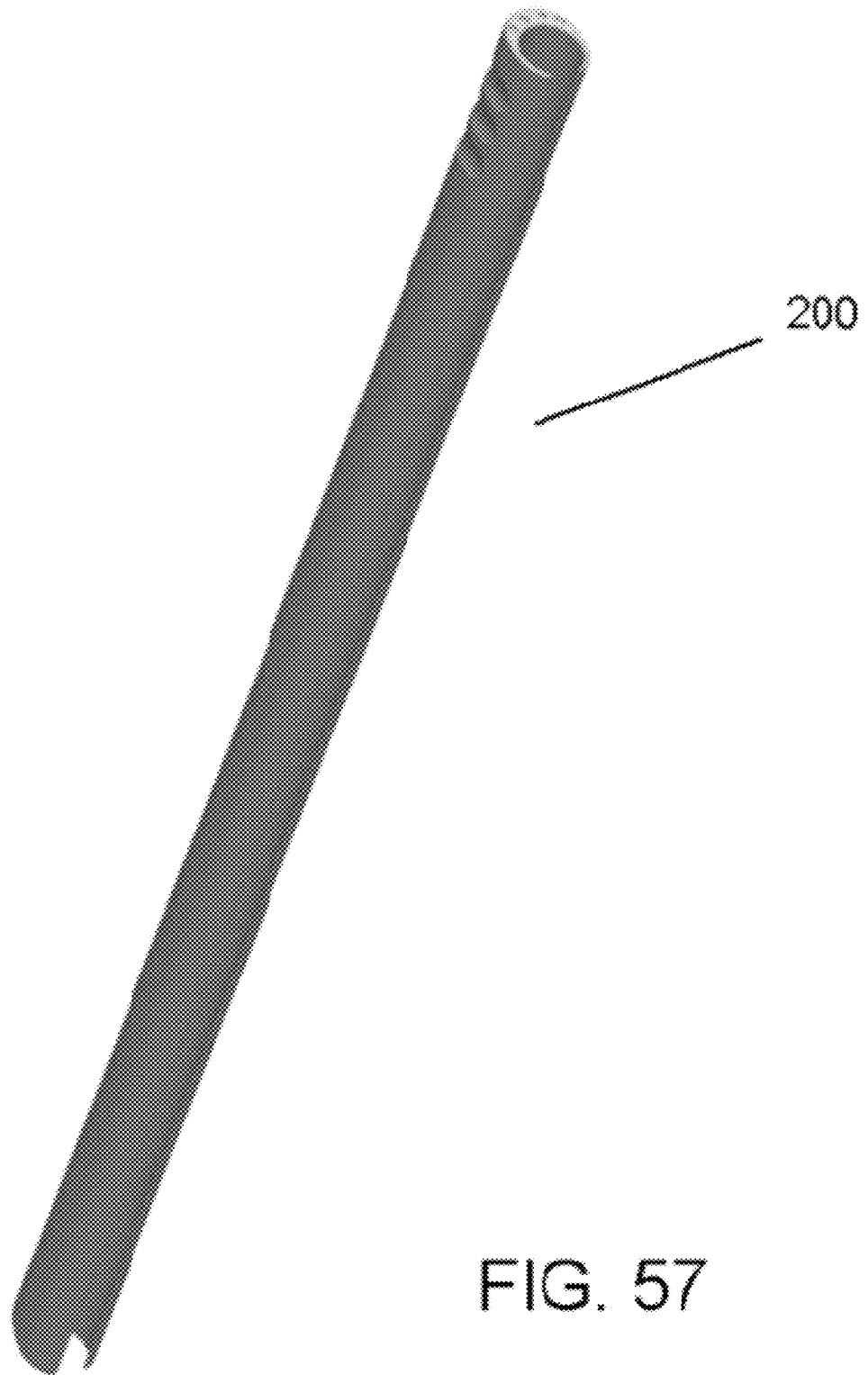
FIG. 57 is a perspective view of a second dilator of the assembly of the dilator system of FIG. 56.
Figure 58:
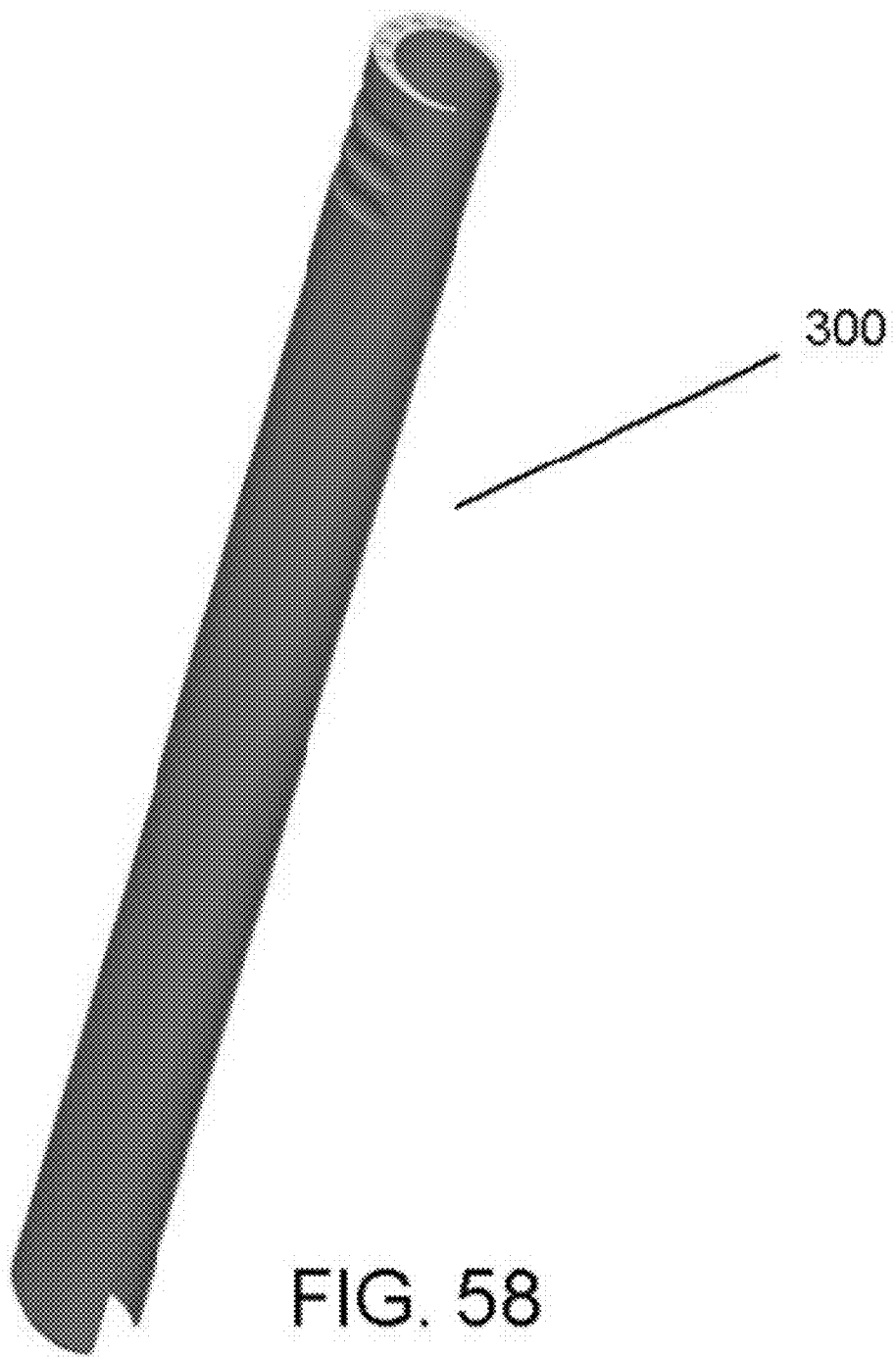
FIG. 58 is a perspective view of a third dilator of the assembly of the dilator system of FIG. 56.
Figure 59:
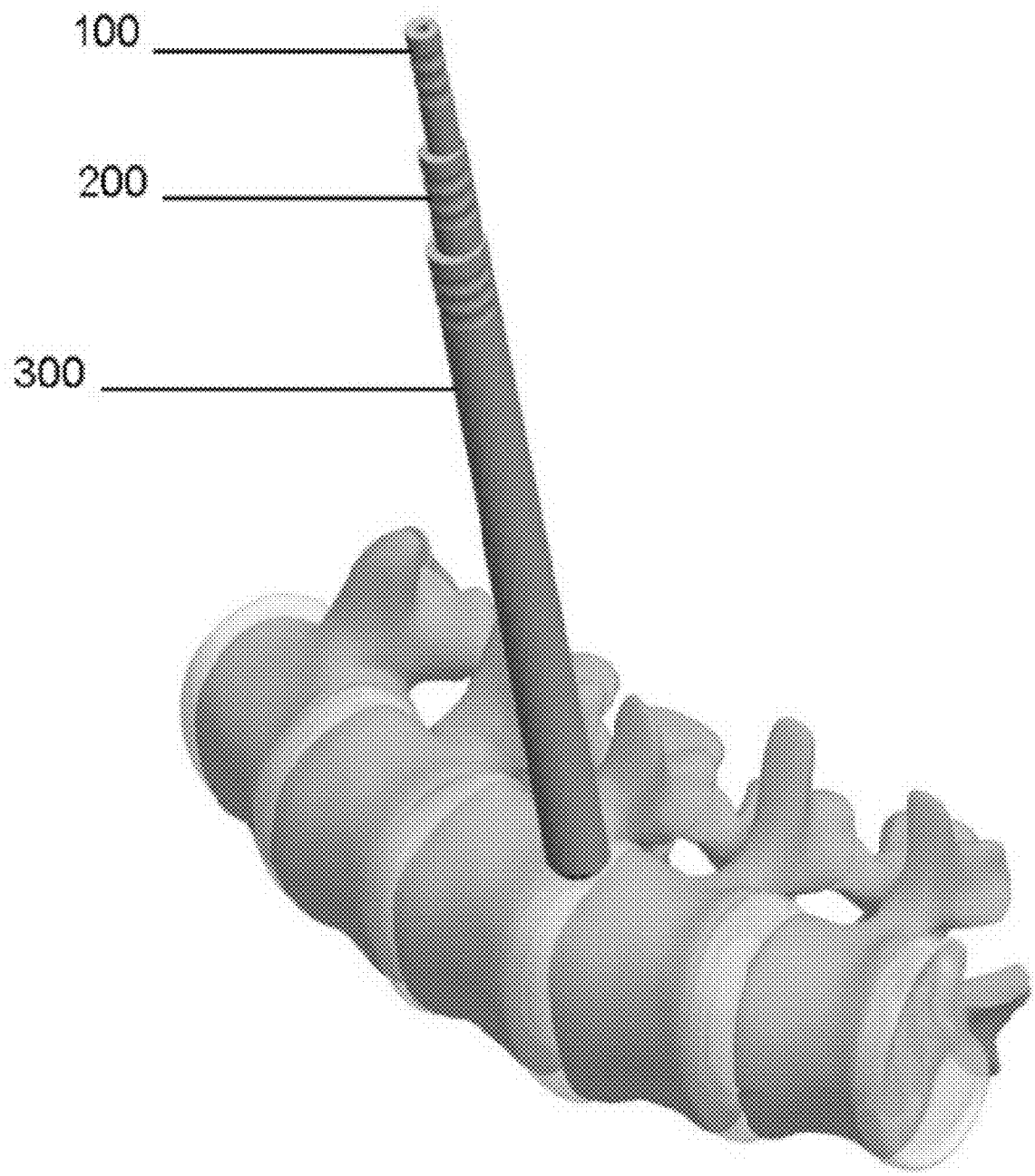
FIG. 59 is a perspective view of the assembly of the dilator system of FIG. 56.
Figure 63:
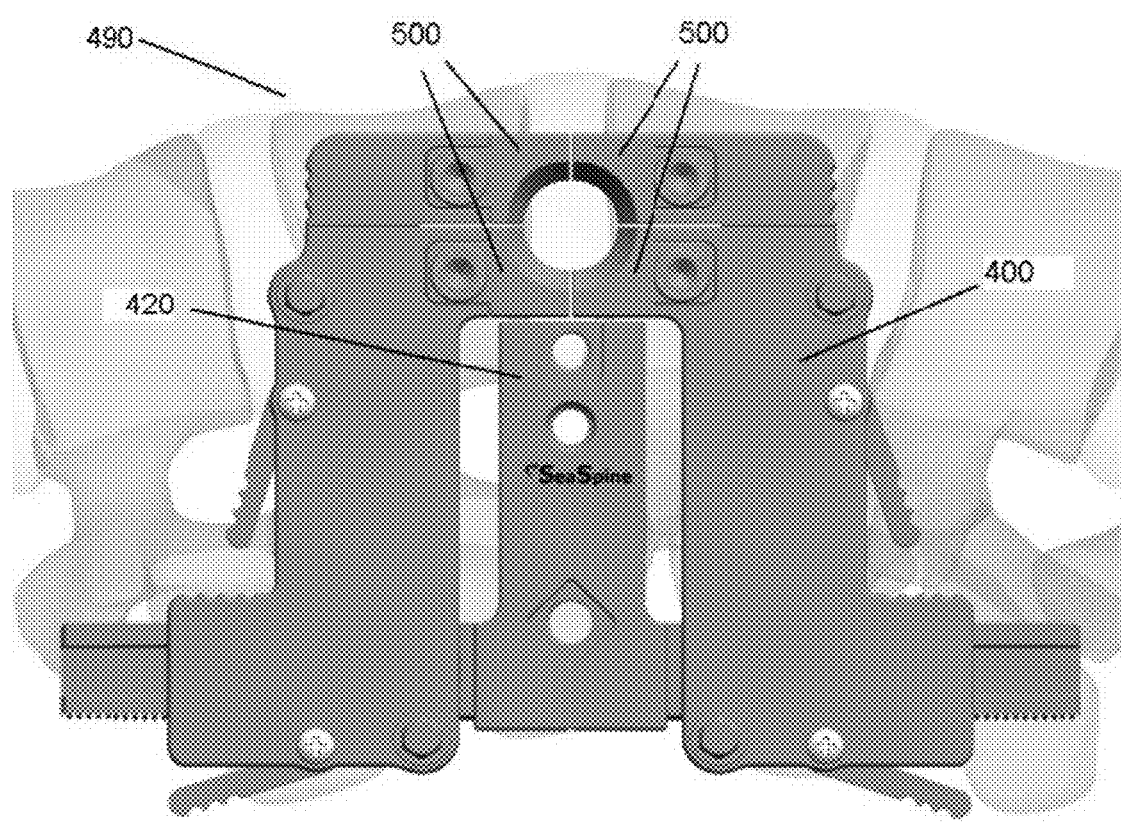
FIG. 63 is a top plan view of one embodiment of an assembly of a retractor system of the present invention positioned over a human spine.

Referring now to FIGS. 49, 50, and 55, yet another embodiment of the invention includes a retractor system 400. In one embodiment, the retractor system includes a retractor frame 402, a plurality of primary retractor blades 500, and a posterior center blade 530, 560. The retractor system may have a closed first position 490 (FIGS. 49 and 55), which may be configured for the blades 500, 530, 560 to be slidingly advanced over dilator system 40. Referring to FIG. 55, in one embodiment the blades 500, 530, 560 are sized and shaped to be advanced over third dilator 300 when the primary and posterior center blade edges 528 are approximated abutting against each other with the retractor system 400 in the closed position 490. In another embodiment, the blades 500, 530, 560 may be sized and shaped to be advanced over the second dilator 200 when the primary and posterior center blade edges 528 are approximated against each other with the retractor system 400 in the closed position 490. In still another embodiment, the retractor system 400 may be used without the dilator system 40. Referring to FIG. 63, in still another embodiment, the posterior center blade 530, 560 is not mounted to the center arm 420 of the retractor system 400, wherein only the primary blades 500 are used for advancement of the retractor system 400 over the dilator system 40. For example, only the primary blades 500 are used for advancement of the retractor system 400 over the dilator system 40 when the retractor system is in closed configuration 490. All four of the primary blades 500, 502 mounted to the retractor may include quarter round concave inner faces 522 (FIGS. 18-20), wherein the inner passageway formed in the closed retractor position 490 is generally circular rather than oblong.

Figure 64:
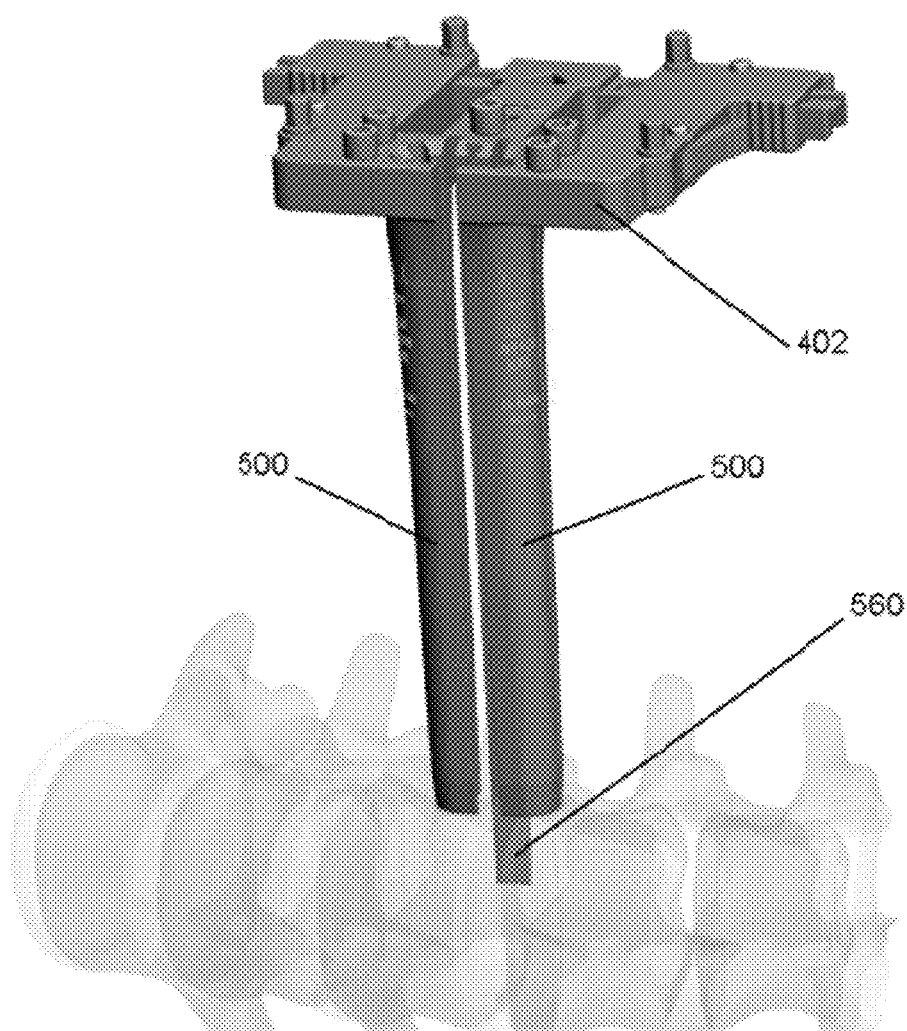
FIG. 64 is a perspective view of one embodiment of an assembly of a retractor system of the present invention positioned over a human spine.
Figure 65:
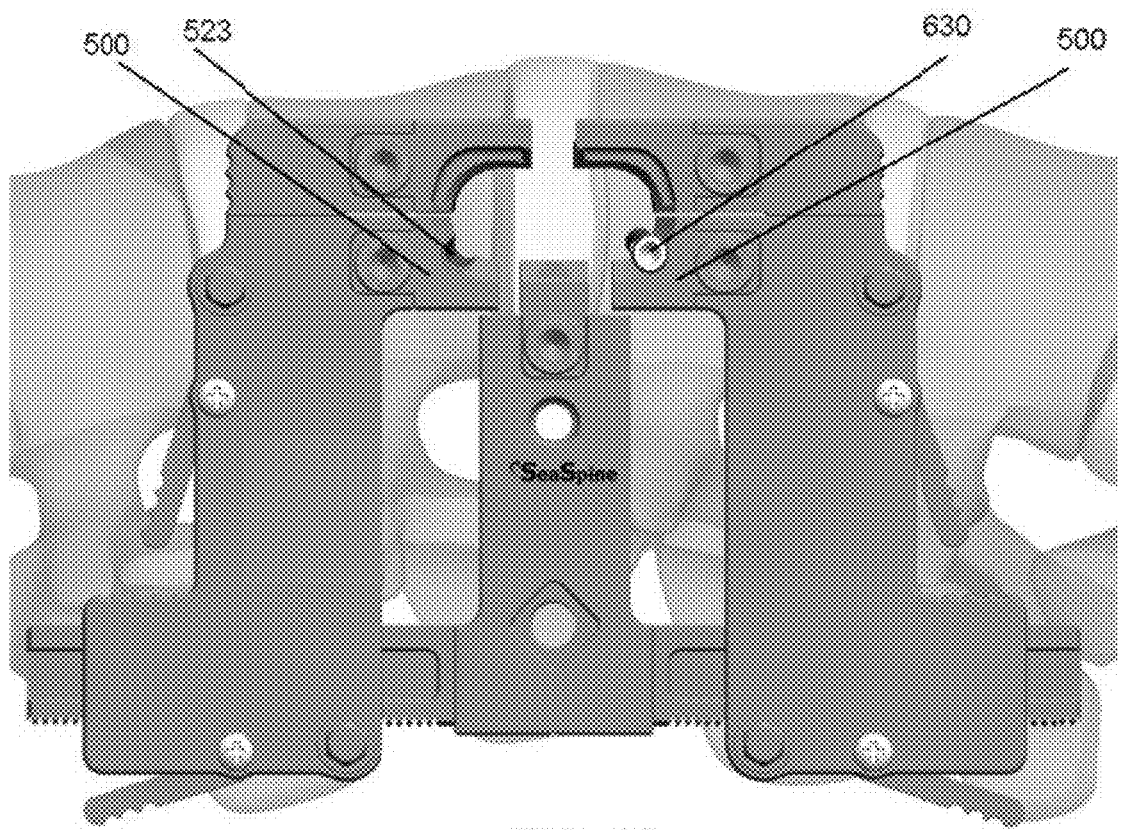
FIG. 65 is a top plan view of one embodiment of an assembly of a retractor system of the present invention including an anchor pin in one anchor pin channel positioned over a human spine.
Figure 66:
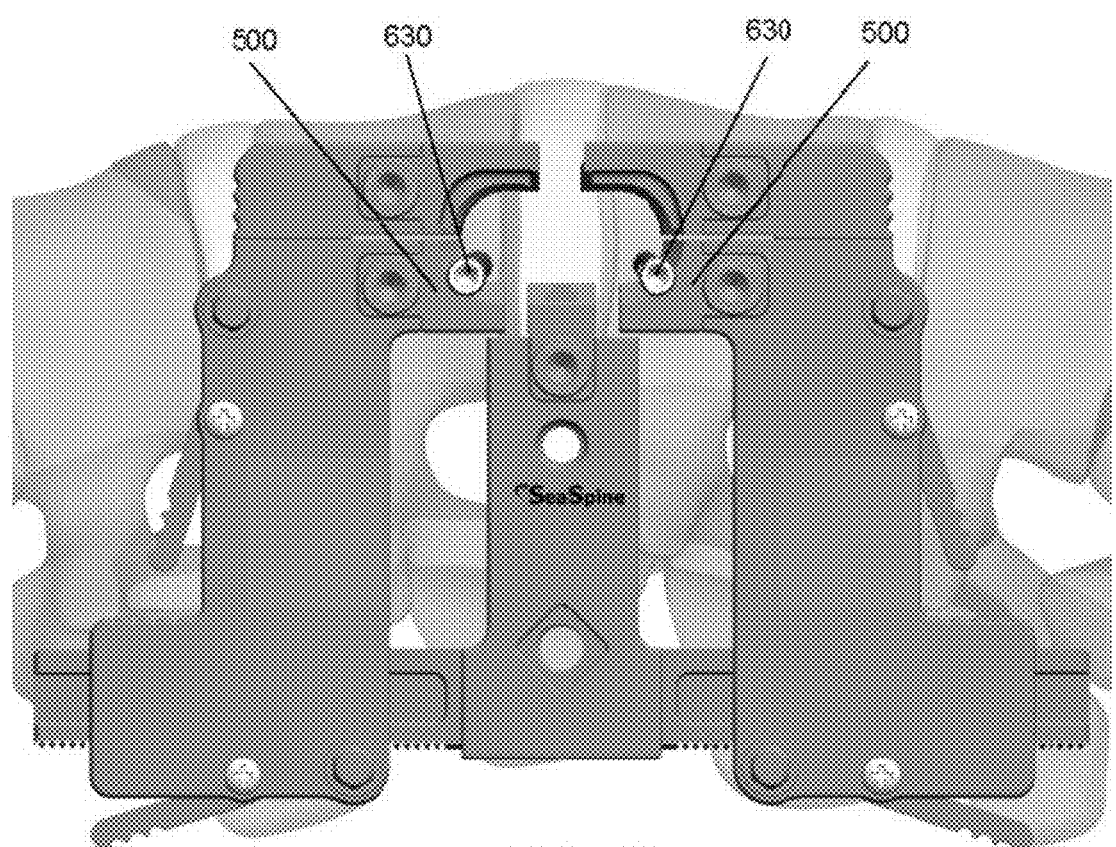
FIG. 66 is a top plan view of one embodiment of an assembly of a retractor system of the present invention including two anchor pins in each of two anchor pin channels positioned over a human spine.

In still another embodiment, the retractor system 400 is configured to retract soft tissues by transitioning the retractor system from a closed position 490 (FIG. 49) to an open position 492 (FIG. 50). In one embodiment, in the open position 492 a blade edge 528 of at least one blade 500, 530, 560 is separated from a blade edge 528 of at least one adjacent blade 500, 530, 560. In one embodiment, in the open position 492 (FIG. 50) each of the blades 500, 530, 560 may not be in contact any adjacent blade 500, 530, 560. At least one advantage of the retractor system 400 is that in at least one embodiment one or more of the blades 500, 530, 560 of the retractor system 400 may be moved independently of movement of another blade 500, 530, 560 of the retractor system 400. In one embodiment, the retractor blades 500, 530, 560 may be translationally and/or linearly moved towards or away from each other without any pivoting motion of the blades 500, 530, 560. In still another embodiment, the posterior center blade 530, 560 may be introduced to the retractor frame 402 after the retractor has reached the open position 492. Referring briefly to FIG. 64, in still another embodiment, the posterior center blade 530, 560 have a longer length than the length of the primary blades 500, wherein the excess length of the posterior center blade may be used to anchor at least a portion of the retractor system 400 within the disc space 20.

Figure 7:
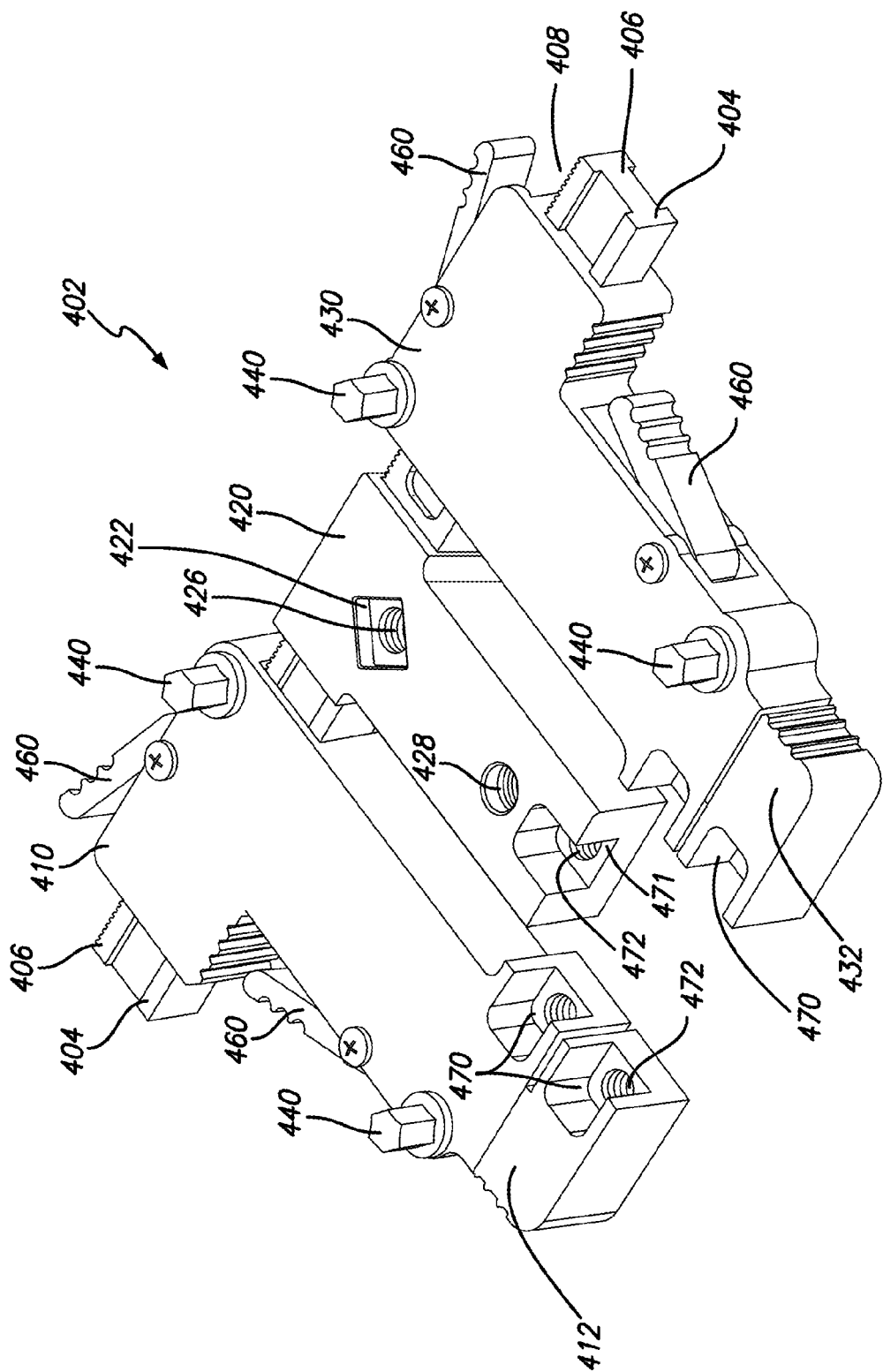
FIG. 7 is a perspective view of one embodiment of a retractor frame of one embodiment of a retractor system of the present invention.
Figure 8:
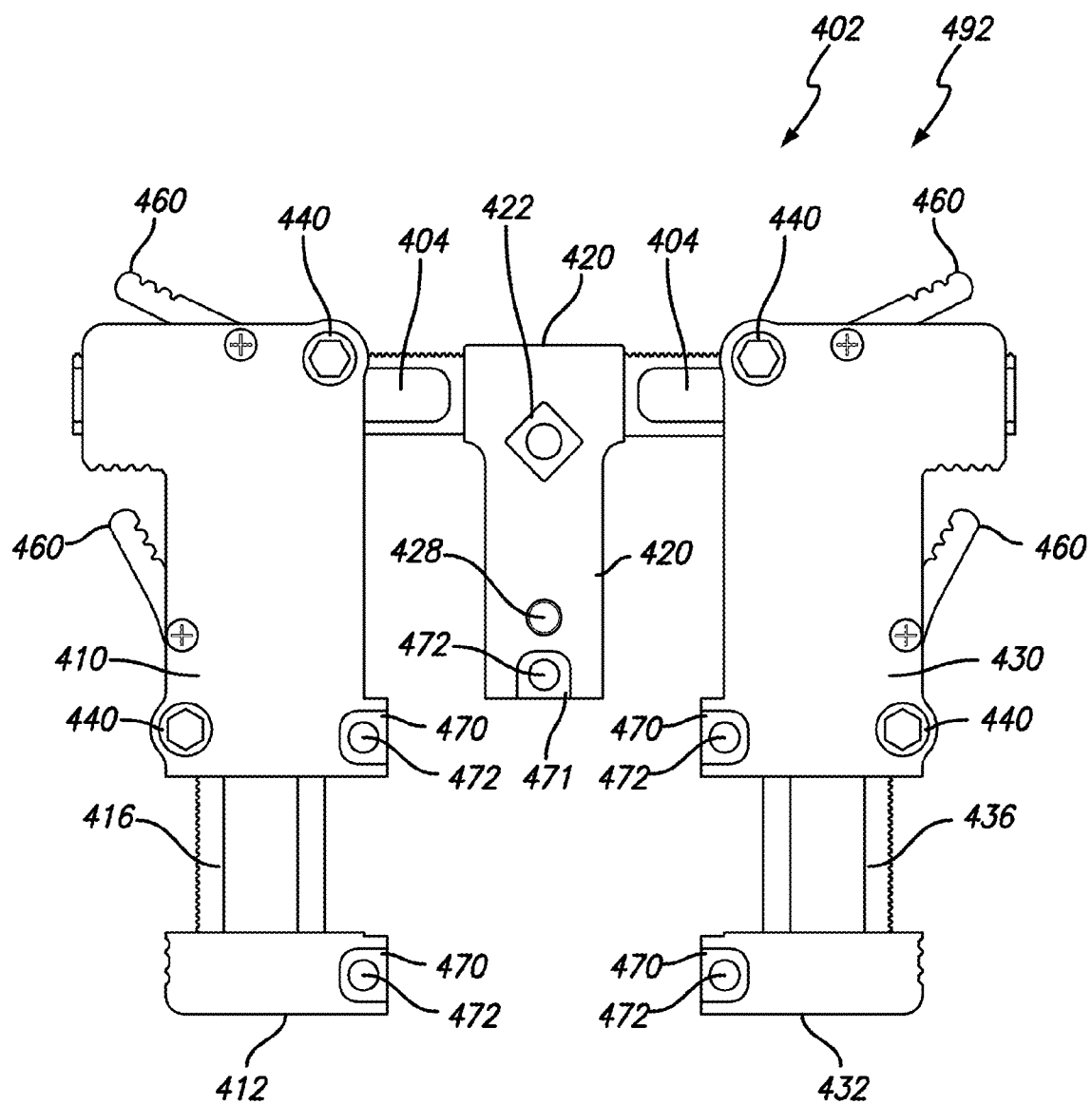
FIG. 8 is a top plan view of the retractor frame of FIG. 7 in an open configuration.
Figure 9:
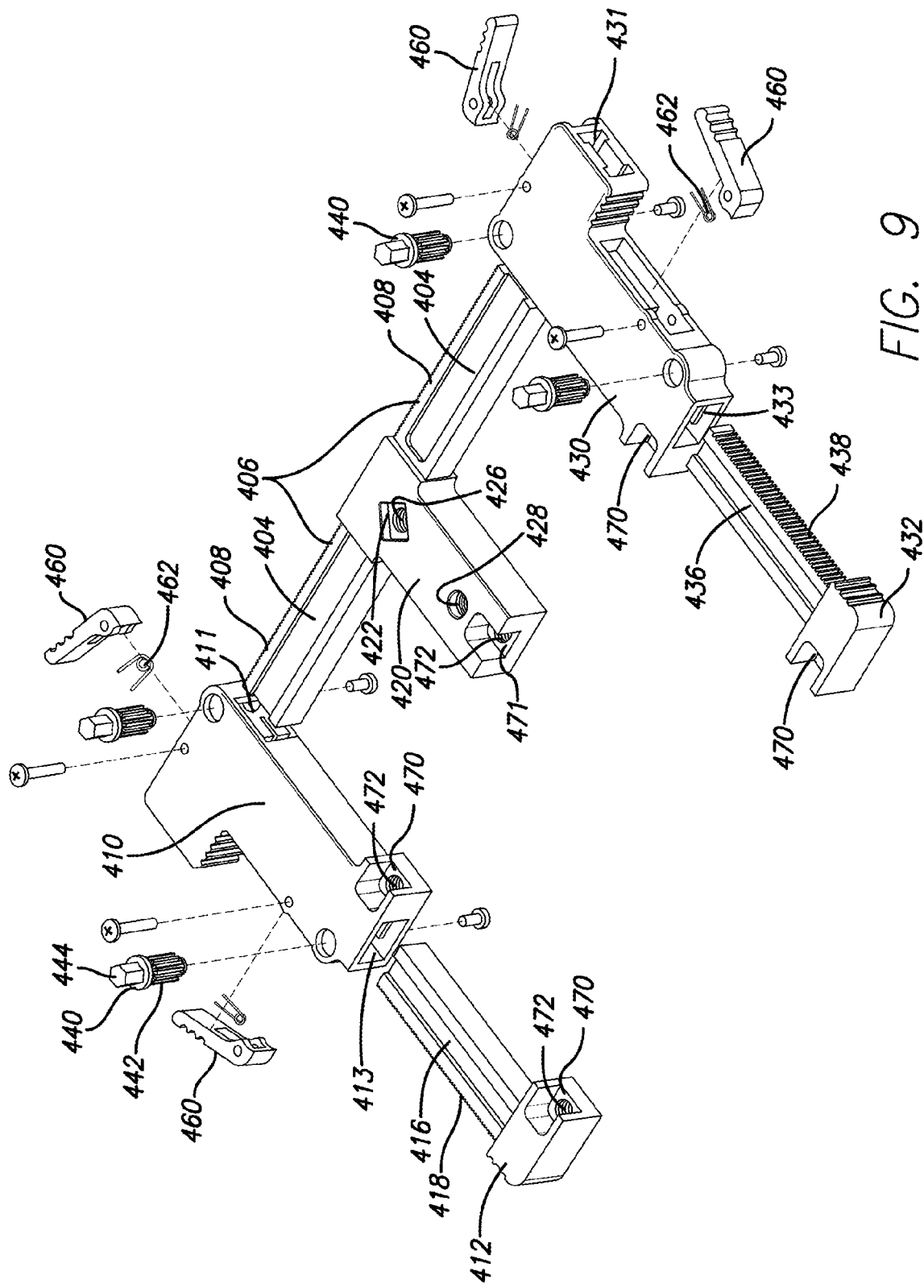
FIG. 9 is an exploded view of the retractor frame of FIG. 7.

Referring now to FIGS. 7-9, one embodiment of a retractor frame 402 includes a center arm 420. A main rail 404 having a gear rack 406 with teeth 408 extends bilaterally and perpendicular to a longitudinal axis of the center arm 420. Referring also to FIG. 12, an additional embodiment of the retractor frame 402 includes a center arm 420 having a first table mounting recess 422 and a second table mounting recess 424. One embodiment of a table mounting recess 424 is square or diamond shaped and includes a threaded opening 426. The table mounting recess 422, 424 may be mated with a table attachment arm 700 (FIGS. 11 and 50) as described in more detail below. Other embodiments may include alternative or additional configurations and/or methods known in the art and appropriate for attaching a retractor frame to an operating table. The retractor frame 402 may also be used without mounting it to the operating table. In at least one embodiment a square recess allows mounting of the table attachment arm in 4 different orientations that are 90 degrees to each other.

Referring also now to FIGS. 13-17 and 39-42, the center arm 420 includes a blade receiving recess 471 configured to mate with an attachment portion 542, 570 of at least one embodiment of a center posterior blade 530, 560. In at least one embodiment, blade receiving recess 471 includes a threaded hole 472 configured to receive blade attachment screw 550, which releasably connects attachment portion 542, 570 of at least one embodiment of a center posterior blade 530, 560 to blade receiving recess 471. In still one further embodiment, center arm 420 of retractor frame 402 may include an auxiliary blade securing threaded hole 428, which may be used with a threaded auxiliary blade attachment screw 558 to releasably secure at least one embodiment of an auxiliary blade 600 (FIGS. 29-38 and 43-48) to the center arm 420. In one embodiment, a center blade 530, 560 attachment screw 550 may include a threaded end 552 and a knurled grip end 554. A threaded auxiliary blade attachment screw 558 may also include a threaded end 557 and a knurled grip end 559.

Still referring to FIGS. 7-9, the retractor frame 402 may further include left arm 410 and right arm 430. The left arm and the right arm each include a transverse passageway 411, 431 for receiving main retractor rail 404. In one embodiment, the main rail 404 may have a generally I-beam cross-sectional shape and at least portions of the transverse passageways 411, 431 include a generally I-shaped cross-sectional opening. The retractor left arm 410 and right arm 430 are independently slidingly movable along main rail 404 relative to each other and center arm 420. The longitudinal axis of the left arm 410, the right arm 430, and the center arm 420 remain generally parallel to each other during transitioning of the retractor 402 between closed position 490 (FIG. 55) and open positions 492 (FIGS. 8 and 50).

The main retractor rail 404 includes a gear rack 406 with teeth 408. Movements of the left arm 410 on the main gear rack 406 and movements of the right arm 430 on the main gear rack 406 are controlled by rotation of pinions 440. Movements of the left arm 410 and right arm 430 on the main gear rack 406 may be limited by releasable pawls 460 and springs 462. In at least one embodiment, each pinion 440 may include a gear portion 442 and a hexagonal extension 444, which is controlled by one or more hex keys 450 (FIGS. 10 and 50).

Additionally, the retractor left arm 410 includes a longitudinal passageway 413 for slidingly receiving a rail/gear rack 416 of a left supplemental arm 412 therein. The left supplemental arm 412 is independently movable along a longitudinal axis of left arm 410. Furthermore the retractor right arm 430 includes a longitudinal passageway 433 for slidingly receiving a rail/gear rack 436 of right supplemental arm 432 therein. The right supplemental arm 432 is independently movable along a longitudinal axis of the right arm 420. In one embodiment, the rails/gear racks 416, 436 of the left supplemental arm 412 and the right supplement arm 432 have generally I-beam cross-sectional shapes and at least a portion of the longitudinal passageways 413, 433 include a generally I-shaped cross-sectional opening.

The left supplemental arm gear rack 416 includes teeth 418 and the right supplemental arm gear rack 436 includes teeth 438. Movements of the left supplemental gear rack 416 relative to the left arm 410 and movements of the right supplemental gear rack 436 relative to the right arm 430 are controlled by rotation of pinions 440. Movements of the left supplemental gear rack 416 relative to the left arm 410 and movements of the right supplemental gear rack 436 relative to the right arm 430 may be limited by releasable pawls 460 and springs 462. In at least one embodiment, each pinion 440 may include a gear portion 442 and a hexagonal extension 444, which is rotationally controlled by one or more hex keys 450 (FIGS. 10 and 50).

Figure 10:
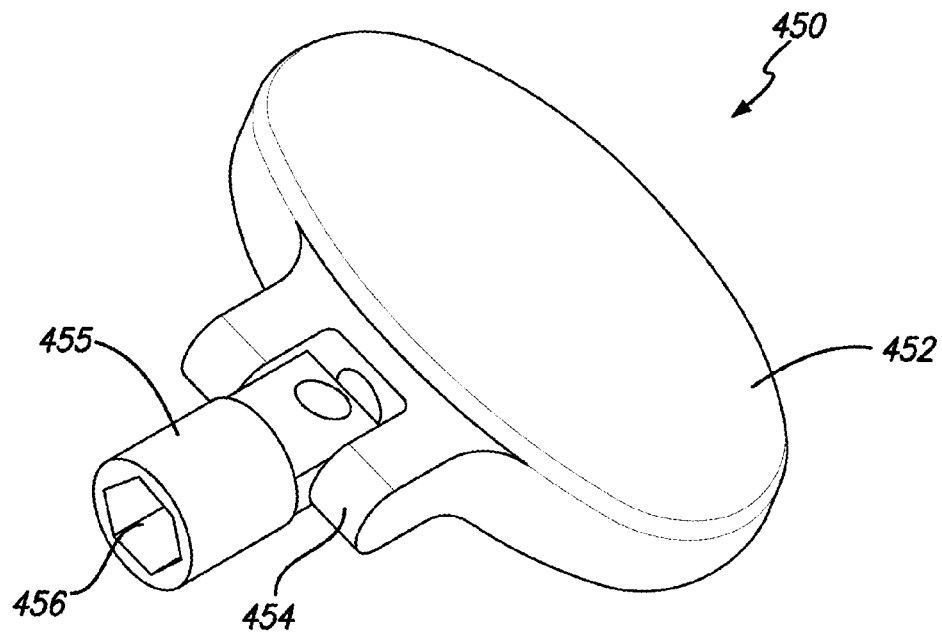
FIG. 10 is a perspective view of one embodiment of a hex key tool of one embodiment of a retractor system of the present invention.

Referring more specifically now to FIGS. 10 and 50, in a further embodiment, the hex key 450 includes a handle portion 452, a tool member 455 having a hexagonal opening 456 on its end, and a pivoting connecting of handle portion 452 to the tool member 455. The hexagonal opening 456 at an end of the tool member 455 is configured to mate with at least one hexagonal extension 444 of pinion 440. The pivoting connection 454 of the handle portion to the tool member permits the hex key handle portion 452 to be folded down out of the way of the surgeon while the hex key tool member 455 remains attached to the hexagonal connection of at least one pinion 440.

Referring again now to FIGS. 7-9, in at least one embodiment, one or more of the left arm 410, right arm 430, left supplemental arm 412, and right supplemental arm 432 include a blade receiving recess 470 having a threaded hole 472. In one embodiment, blade attachment screws 480 may be provided to releasably threadingly connect at least one primary blade 500 to at least one blade receiving recess 470. In a further embodiment, the blade attachment screws 480 may include a knurled grip end 482 and a threaded end 484, which is configured to threadingly mate with the threaded hole 472 in the blade receiving recess 470. In one embodiment the knurled grip end may include a recess, for example a hexagonal recess, for mating with a blade attachment screw tightening tool, for example a hexagonal ended screw driver. In yet other embodiments, the blades may be attached to the arms by other means known in the art, for example by rivets or snap fittings.

Figure 11:
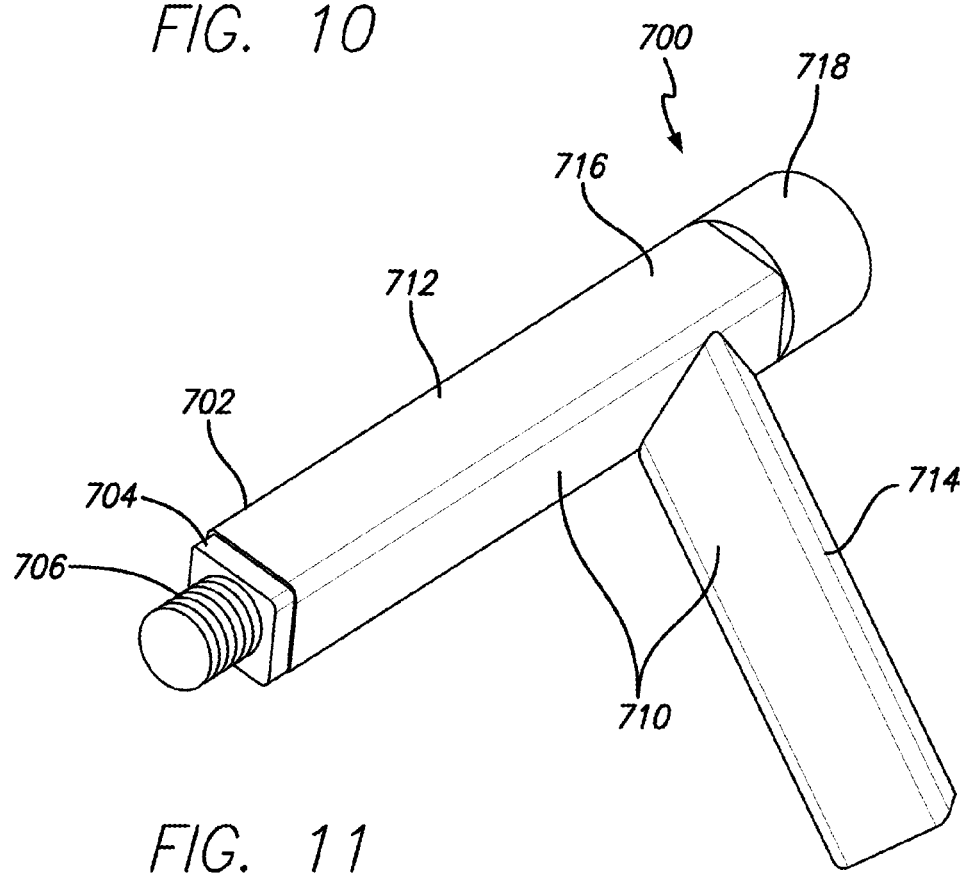
FIG. 11 is a perspective view of one embodiment of a table attachment arm of one embodiment of a retractor system of the present invention.
Figure 12:
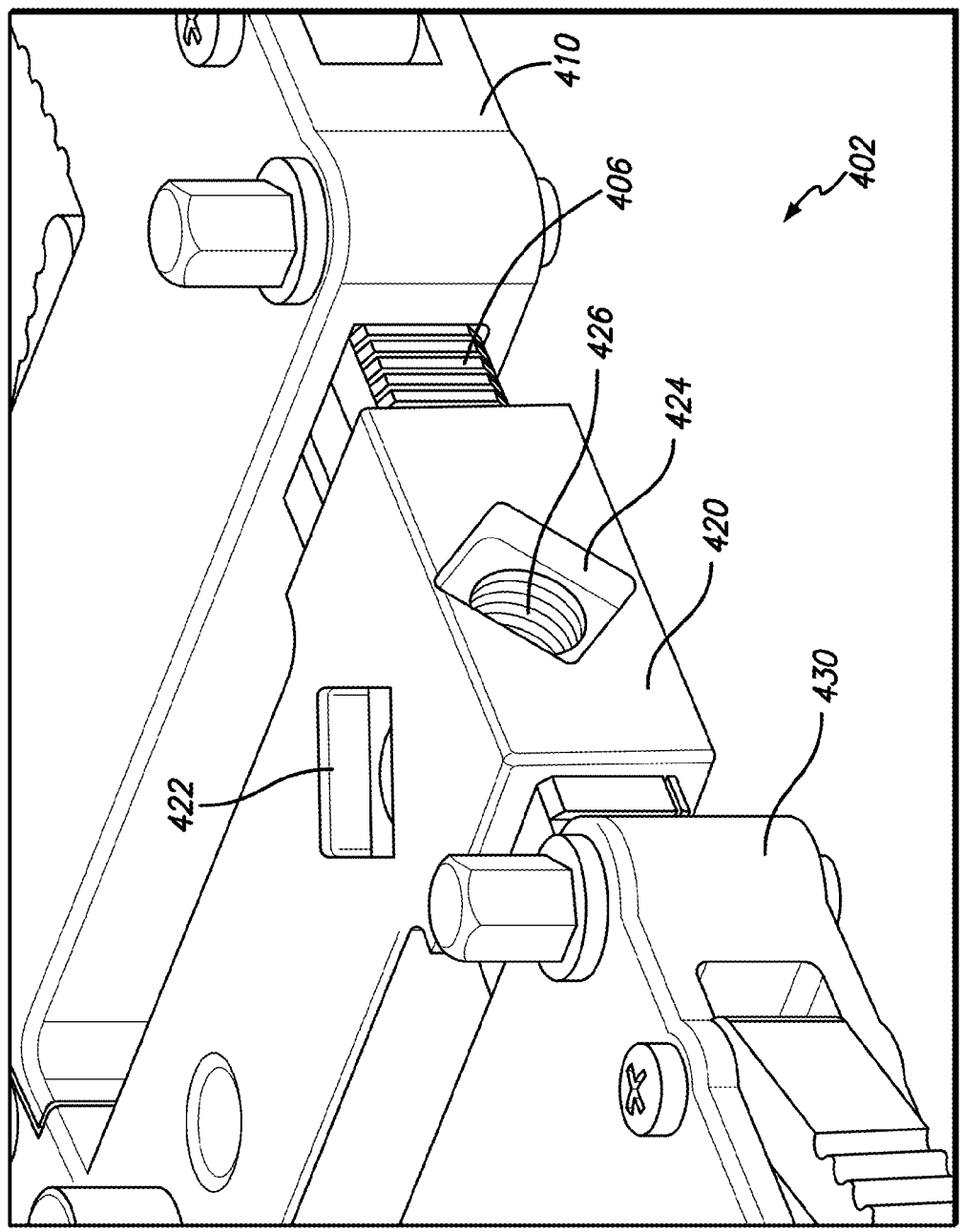
FIG. 12 is a top and posterior perspective view of a portion of the retractor frame of FIG. 7.
Figures 16, 17:
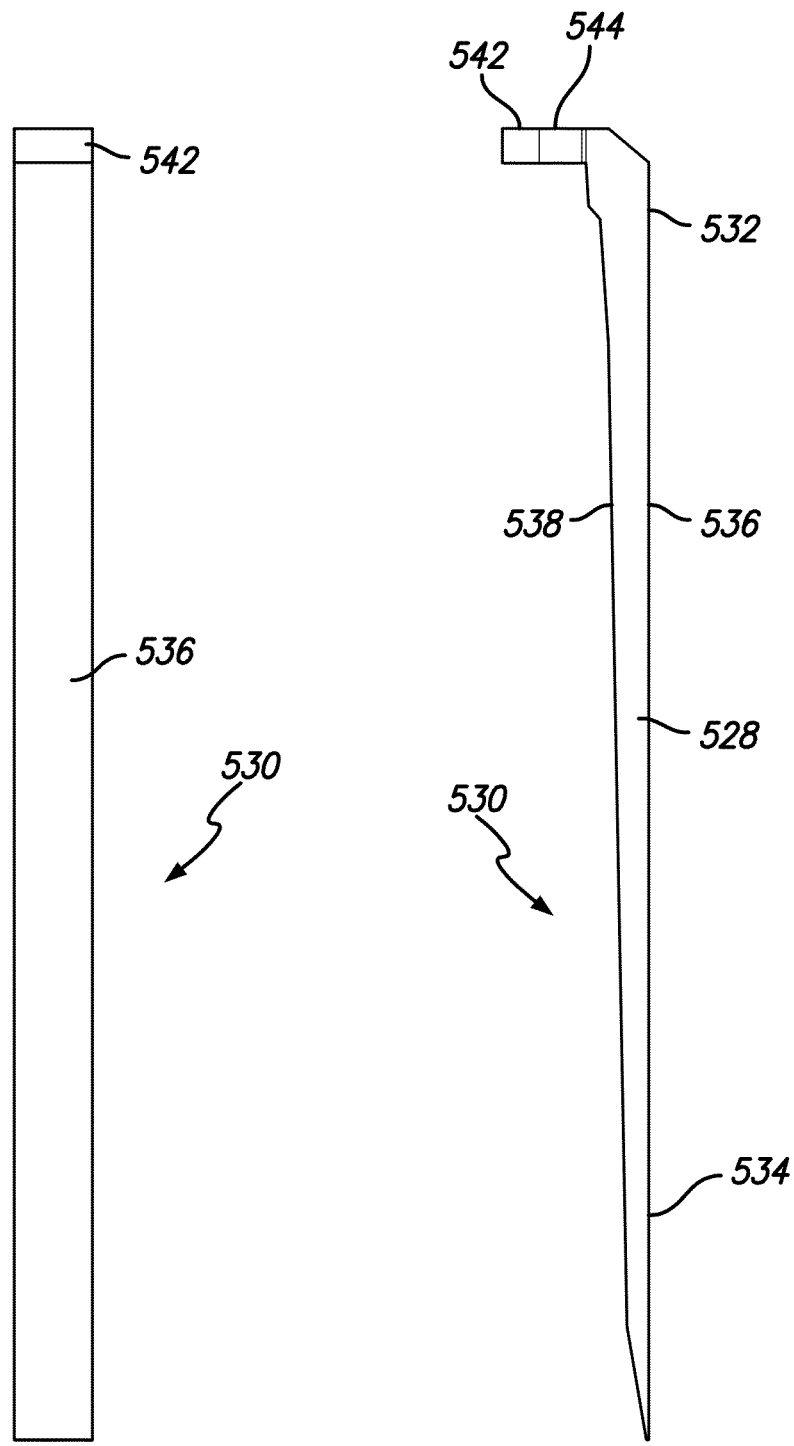
FIG. 16 is a back posterior plan view of the center blade of FIG. 13 without the threaded blade attachment screw.
FIG. 17 is a side plan view of the center blade of FIG. 13 without the threaded blade attachment screw.
Figure 21:
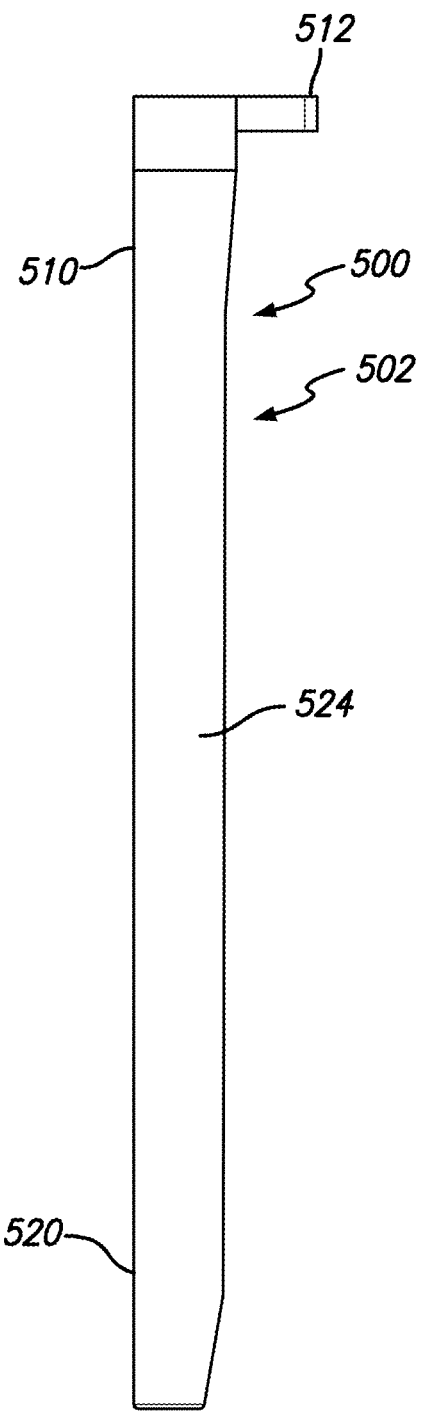
FIG. 21 is a rear plan view of the primary blade of FIG. 18 without the threaded blade attachment screw.
Figure 22:
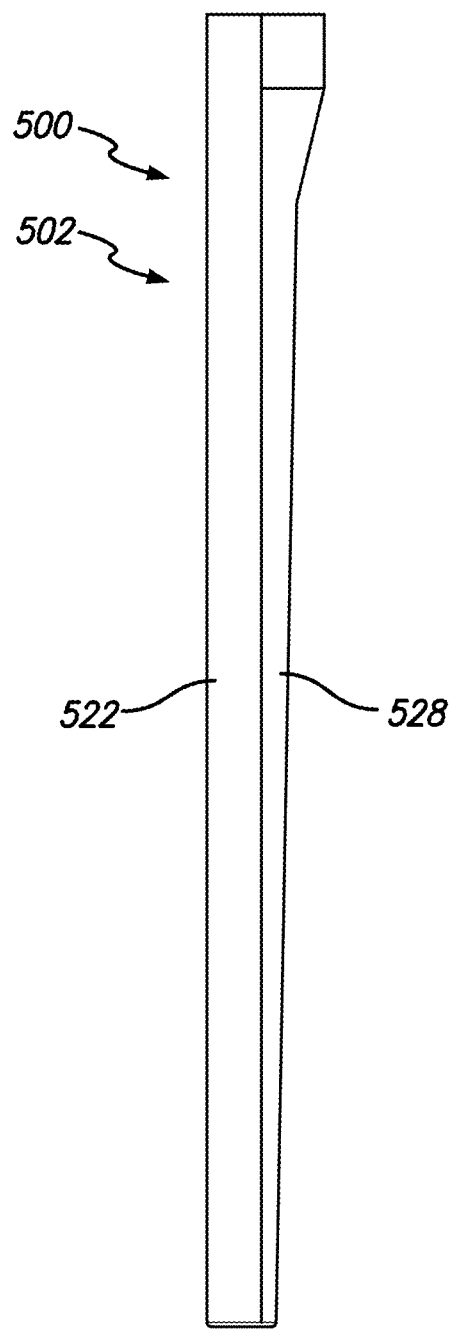
FIG. 22 is a side plan view of the primary blade of FIG. 18 without the threaded blade attachment screw.
Figure 26:
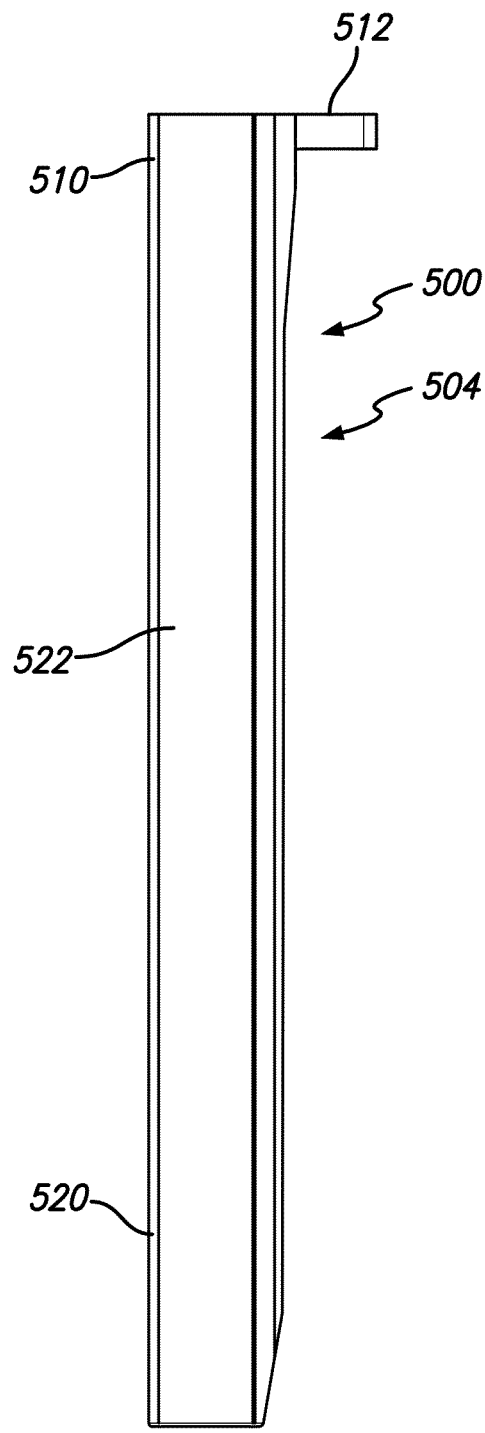
FIG. 26 is a rear plan view of the primary blade of FIG. 23 without the threaded blade attachment screw.
Figure 27:
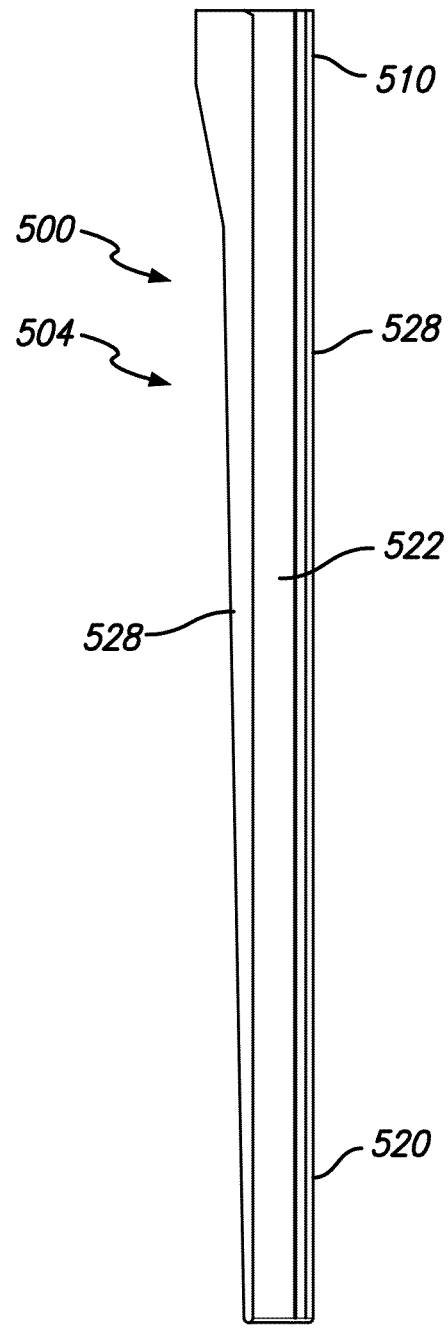
FIG. 27 is a side plan view of the primary blade of FIG. 23 without the threaded blade attachment screw.

Referring briefly now also to FIGS. 11 and 12, in yet an additional embodiment, a table attachment arm 700 is included in the retractor system 400. The table attachment arm has a distal end 702 that may include a generally square or diamond shaped base 704 that is configured to mate with at least one table mounting recess 424 in the center arm 420 (FIG. 12). In at least one embodiment, a square shape of the table attachment arm base 704 and table mounting recess 424 allows connection of the table attachment arm 700 relative to the retractor frame 402 in one of four orientations. The distal end 702 of the table attachment arm 700 may further include a threaded portion 706 configured to rotate relative to the base 704. The threaded portion 706 of the table attachment arm 700 is configured to threadingly engage the threaded opening in at least one table mounting recess 422, 424. In still a further embodiment, the table attachment arm 700 may include a body 710 having a longitudinal portion 712 and a transverse portion 714. The table attachment arm base 704 and table mounting recess 424 may have mating shapes other than squares or diamonds that permit greater or lesser variations in orientation of the table attachment arm transverse portion 714 to the retractor frame 402. The threaded portion 706 of the table attachment arm 700 is disposed on the distal end 702 of the longitudinal portion 712. A rotational knob 718 may be disposed on a proximal end 716 of the table attachment arm 700 longitudinal portion 712. The rotational knob 718 is connected with the threaded portion 706 by an axle (not shown) within a lumen of longitudinal portion 712 of table attachment arm 700. The threaded portion 706 is configured to rotate relative to table attachment arm base 704. Rotation of the knob 718 by a surgeon rotates the threaded portion 706 relative to the arm base 704. In at least one embodiment, rotation of threaded portion 706 by knob 718 may be used to detachably connect table attachment arm 700 to retractor frame 402 mounting recess 424. Alternatively, other configurations known in the art for mounting a retractor system to an operating table and/or patient may by provided.

Referring now to FIGS. 13-46, the retractor system may further include a plurality of blades. In one embodiment, retractor blades may include center posterior blades 530, 560, primary blades 500, 501, 502, 503, 504, and/or auxiliary blades 600, 610, 620, 650.

Referring more specifically to FIGS. 13-17, one embodiment of a posterior center blade 530 has a proximal end 532 and a distal end 534. The center blade 530 includes an inner face 536 configured to face towards an inside of surgical passageway and an outer face 538 configured to face away from the inside of surgical passageway. In at least one embodiment the posterior center blade has a generally flat inner face 536. In at least another embodiment the posterior center blade has a generally flat outer face 538. However, other shapes of inner face or outer face, for example concave or convex faces may be used in alternative embodiments not shown. In one embodiment, center blade 530 may be tapered and/or beveled along at least a portion of its length and/or at the distal end 534. The proximal end of the center blade 530 includes an attachment portion 542 configured to mate with a center blade receiving recess 471 in center arm 420 of retractor frame 402. The attachment portion 542 may include a hole 544 (FIG. 14) configured for passage of attachment screw 550 threaded end 552 while prohibiting passage of attachment screw grip end 554 (FIG. 13). The attachment screw 550 may be used to releasably secure at least one embodiment of the center blade 530 to the receiving recess 471 in center arm 420 by passing threaded end 552 through hole 544 in blade, threadingly connecting threaded end 552 to threaded hole 472 in center arm recess 471, and tightening attachment screw 550 using grip end 554. In one embodiment the hole 544 is unthreaded. In another embodiment the hole 544 is threaded.

Referring briefly now to FIGS. 39-42, still another embodiment of a center blade 560 has a proximal end 562 and a distal end 564. The center blade may include a generally flat inner face 566 and a generally flat outer face 568. Posterior center blade 560 may include an attachment portion 570 having a hole 574. The hole 574 in the attachment portion 570 permits passage of the threaded end 552 of the attachment screw 550 while prohibiting passage of attachment screw grip end 554. The attachment screw 550 may be used to releasably secure at least one embodiment of the center blade 560 to the receiving recess 471 in the center arm 420 by passing the threaded end 552 through the hole 574 in the center blade 560, threadingly connecting attachment screw threaded end 552 to threaded hole 472 in center arm recess 471, and tightening attachment screw 550 using grip end 554. In one embodiment the hole 574 is unthreaded. In another embodiment the hole 574 is threaded.

Referring now to FIGS. 18-28, 49, and 50 in still another embodiment, the retractor system 400 includes a plurality of primary blades 500. In at least one embodiment the primary blades are configured to attach to at least one of the left arm 410, the right arm 430, the left supplemental arm 412, and the right supplemental arm 432. In one embodiment the primary blades 500 may include symmetrical primary blades 501, 502 and/or asymmetrical primary blades 503, 504. Referring specifically to FIGS. 18-22 and 28, the symmetrical primary blades 501, 502 have a configuration including a symmetrical generally "quarter round" shaped concave inner face 522. Referring specifically to FIGS. 23-28, the asymmetrical primary blades 503, 504 have a configuration that includes a quarter round portion and additionally a flat portion. In one embodiment the asymmetrical primary blades inner face 522 may be described as being asymmetrical and somewhat "J" shaped. The attachment members of asymmetrical primary blades 503, 504 are also more elongated on their anterior side compared to a length of the posterior side of the attachment members of the symmetrical primary blades 501, 502. Right sided symmetrical primary blade 501 is a minor image of left sided symmetrical primary blade 502. Right sided asymmetrical primary blade 503 is a mirror image of left sided asymmetrical primary blade 504.

Figure 28:
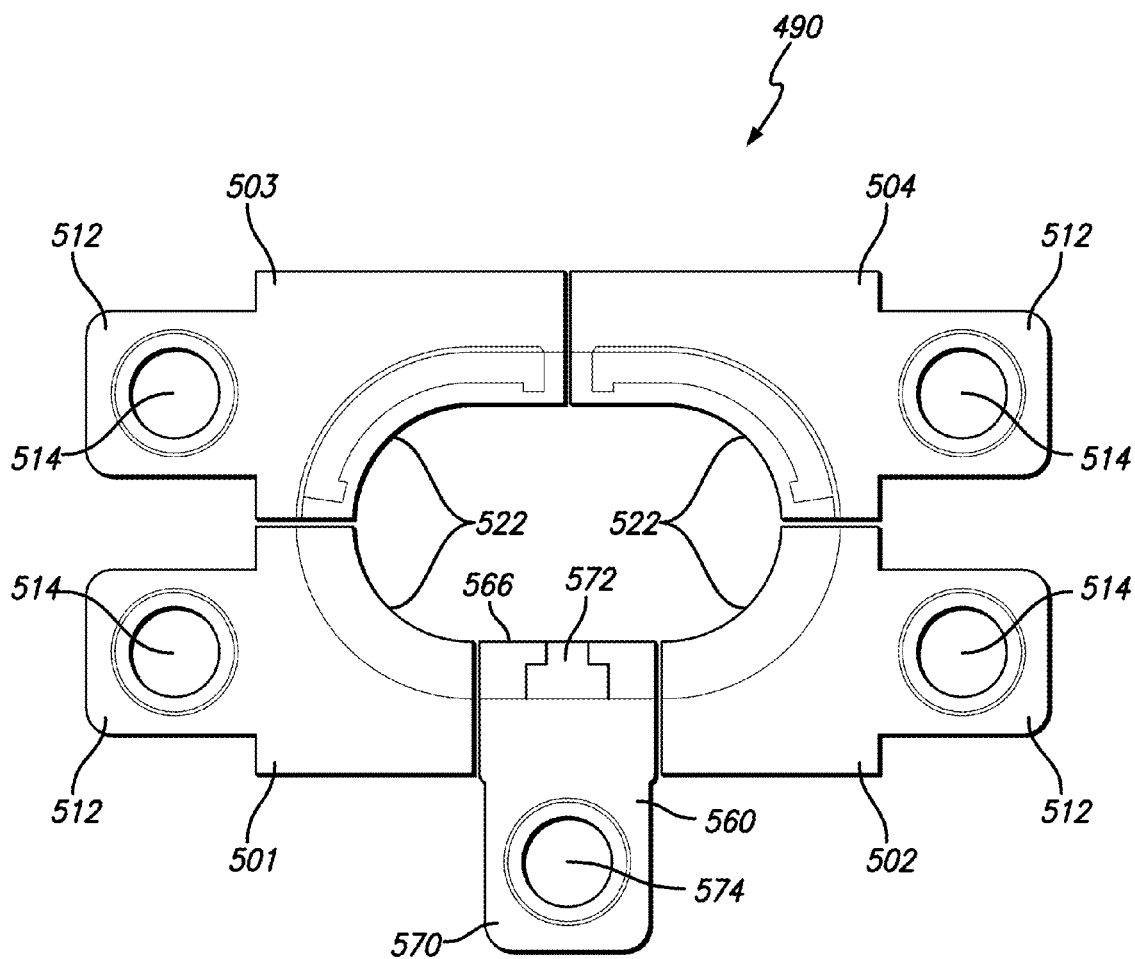
FIG. 28 is a top plan view of embodiments of primary blades and a center blade in an approximated closed position.

Referring still to FIG. 28 and also to FIG. 49, in at least one embodiment, two asymmetrical primary blades 503, 504, two symmetrical primary blades 501, 502 and one center blade 530, 560 are attached to the retractor frame 402 to provide an oval and/or oblong shaped operating corridor when the retractor frame 402 is in a closed position 490. In this oblong operating corridor configuration the two asymmetrical primary blades 503, 504 are positioned anterior. The two symmetrical primary blades 501, 502 are positioned posteriorly with one posterior central blade 530, 560 positioned therebetween. In at least one embodiment, symmetrical primary blade 501 is configured to detachably connect with retractor right arm 430, symmetrical primary blade 502 is configured to detachably connect with the retractor left arm 410, asymmetrical primary blade 503 is configured to detachably connect with retractor right supplemental arm 432, and asymmetrical primary blade 504 is configured to detachably connect with retractor left supplemental arm 412. The anterior length of the attachment members 512 on asymmetrical primary blades 503, 504 are elongated compared to the posterior length of the attachment members 512 on the symmetrical primary blades 501, 502. With the retractor frame 402 in a closed position, the posterior positioned symmetrical primary blades 501, 502 are configured to accommodate therebetween the width of one of the posterior central blade 530, 560. The configurations of the posterior positioned symmetrical primary blades 501, 502 and the anteriorly positioned asymmetrical primary blades 503, 504 provides for the side edges 528 of the five blades 501, 502, 503, 504, 560 to abut to form a closed oblong operative corridor when the retractor frame 402 is in the closed position 490.

Furthermore, the retractor system may be used without a center posterior blade. In still another embodiment (not shown), an asymmetrical primary blade 503, 504 having a partially concave generally "J" shaped inner face 522 may be attached to each of the four blade receiving recesses 470 without attaching a posterior central blade 530, 560 thereby forming yet another configuration of an oblong operative corridor when the frame 402 is in a closed position 490.

In still another embodiment of the present invention, an outermost dilator may include a circular cross-sectional shaped exterior wall. In yet another embodiment, the primary retractor blades 501, 502 may be configured with concave inner faces that form a circular central corridor when the retractor system is in a closed configuration without the center posterior blade 530, 560 attached to the center arm 420 of the retractor frame 402. A symmetrical primary blade 501, 502 having a quarter round inner face 522 may be attached to each of the four blade receiving recesses 470 without attaching a posterior central blade 530, 560 thereby forming a circular operative corridor when the frame 402 is in a closed position. The circular central corridor is formed when the edges 528 of the four symmetrical primary blades 501, 502 each having a quarter round inner face 522 abut with edges 528 of at two adjacent symmetrical quarter round primary blades 501, 502. The circular central corridor formed in the closed configuration 490 of the retractor system 400 may be slidingly advanced over a proximal end of the outermost dilator's circular shaped exterior wall and then slidingly advanced distally over the outermost circular dilator.

Figure 52:
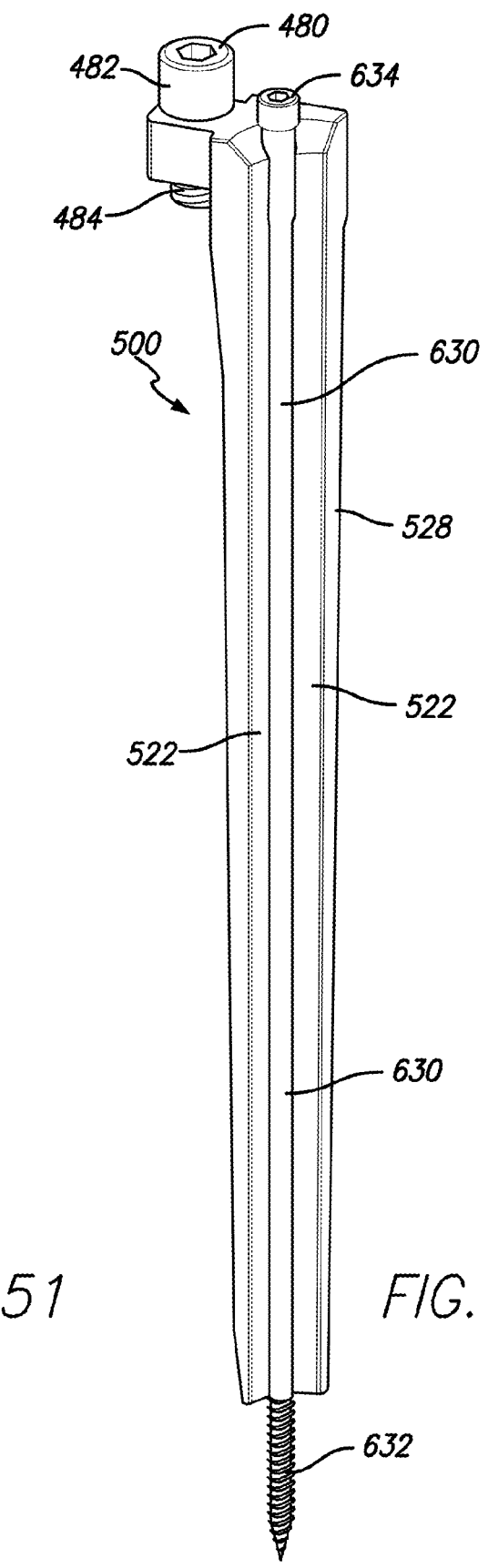
FIG. 52 is an inner perspective view of the primary blade of FIG. 51, further including an anchor pin in the anchor pin channel.

Referring again now to FIGS. 18-28, the primary blades 500 have a proximal portion 510 and a distal portion 520. In at least one embodiment primary blades 500 may include an inner face 522 that is at least partially concave. In still another embodiment primary blades 500 may include an outer face 524 that is at least partially convex. In yet an additional embodiment primary blades may include a tapered portion 526 along the length or at the distal portion 520. The proximal portion 510 includes attachment member 512 configured to mate with a blade receiving recess 470. Attachment member may include hole 514 to allow threaded end 484 of blade attachment screw 480 to pass therethrough while prohibiting passage of grip end 482 (FIG. 52). The hole 514 may be threaded or unthreaded. Grip end 482 may include a knurled surface. In at least one embodiment a primary blade 500 may be detachably connected with the retractor frame 402 by mating an attachment member 512 with a blade receiving recess 470, and securing the attachment member 512 to the frame 402 by tightening the blade attachment screw 480 threaded end 484 into threaded hole 472 in one of the retractor arms 410, 430, 412, 432.

Referring briefly now to FIGS. 51, 52, 65, and 66, in yet another embodiment, a primary blade 500 may include a channel 523 configured to receive and hold an elongated anchor pin 630. The anchor pin may include a proximal grip end 634 and a distal threaded end 632. The distal threaded end 632 is configured to be threadingly advanced into bone, for example a vertebral body, to provide supplemental stabilization to the primary blade 500. In another example, two anchor pins may be used in two primary blades 500. An anchor pin may be attached to each of an anatomically inferior vertebral body and an anatomically superior vertebral body, wherein the vertebral bodies may be distracted by the retractor movement. The distraction of the vertebral bodies may thereby improve ease of intervertebral body cage implantation and nerve root decompression. In one embodiment, the proximal grip end 634 of the anchor pin 630 may be turned by hand. In yet another embodiment, the proximal grip end 634 of the anchor pin may be turned by a tool (not shown). In yet another embodiment, the anchor pin 630 may securely mate within the blade channel 523, wherein the anchor pin may be turned and longitudinally moved within the channel 523 while restricting transverse dislodgement of the anchor pin 630 from the channel 523. In still a further embodiment, the anchor pin 630 may be configured to be transversely moved or snapped into or out of the channel 523 by the user, in addition to being configured for rotation and longitudinally movement of the anchor pin 630 within the channel 523.

Figures 29, 30, 31:
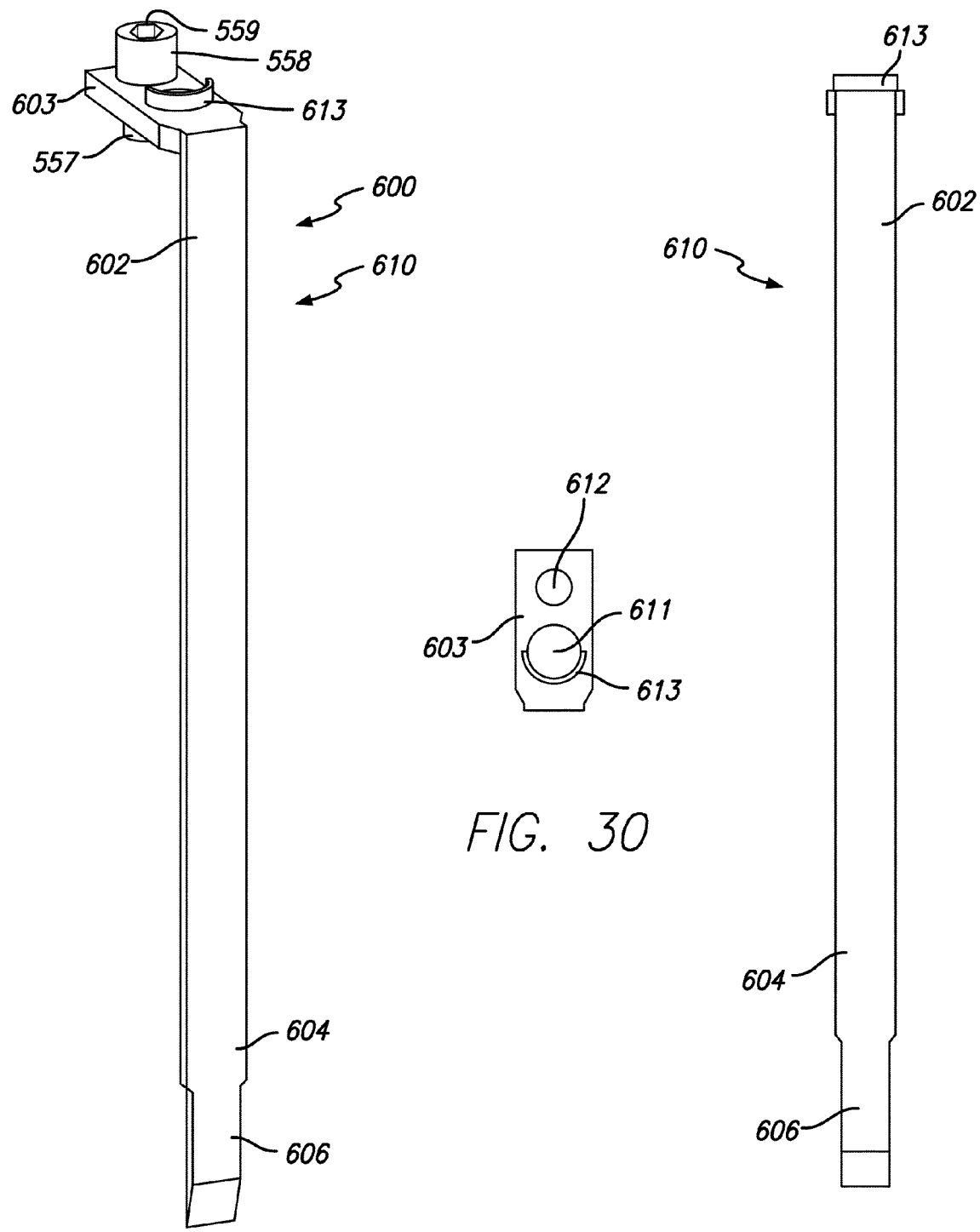
FIG. 29 is a perspective view of an embodiment of an auxiliary blade of an embodiment of the retractor system of the present invention including a threaded blade attachment screw.
FIG. 30 is a top plan view of the auxiliary blade of FIG. 29 without the threaded blade attachment screw.
FIG. 31 is a frontal plan view of the auxiliary blade of FIG. 29 without the threaded blade attachment screw.
Figures 32, 33:
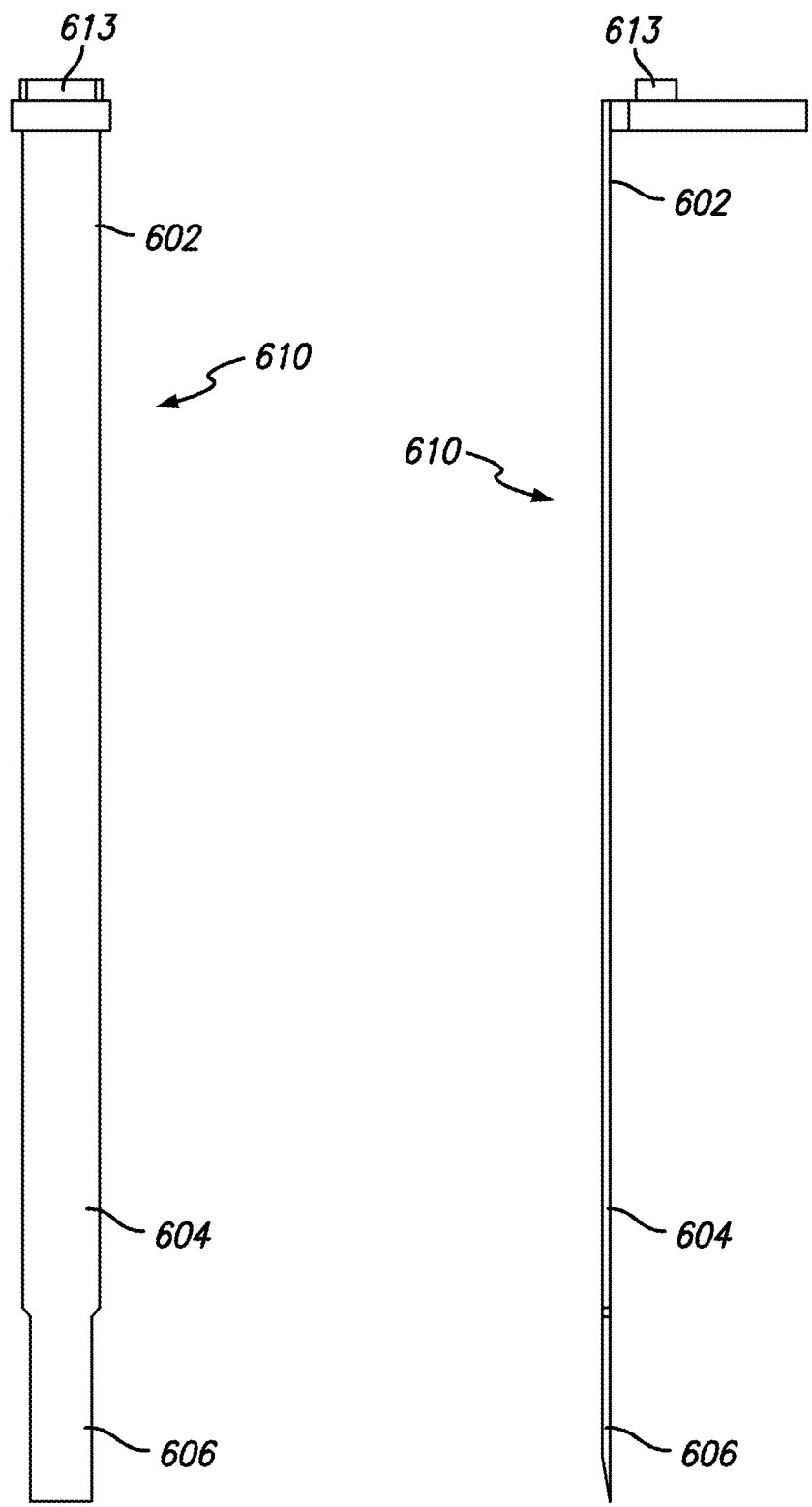
FIG. 32 is a rear plan view of the auxiliary blade of FIG. 29 without the threaded blade attachment screw.
FIG. 33 is a side plan view of the auxiliary blade of FIG. 29 without the threaded blade attachment screw.
Figure 37:
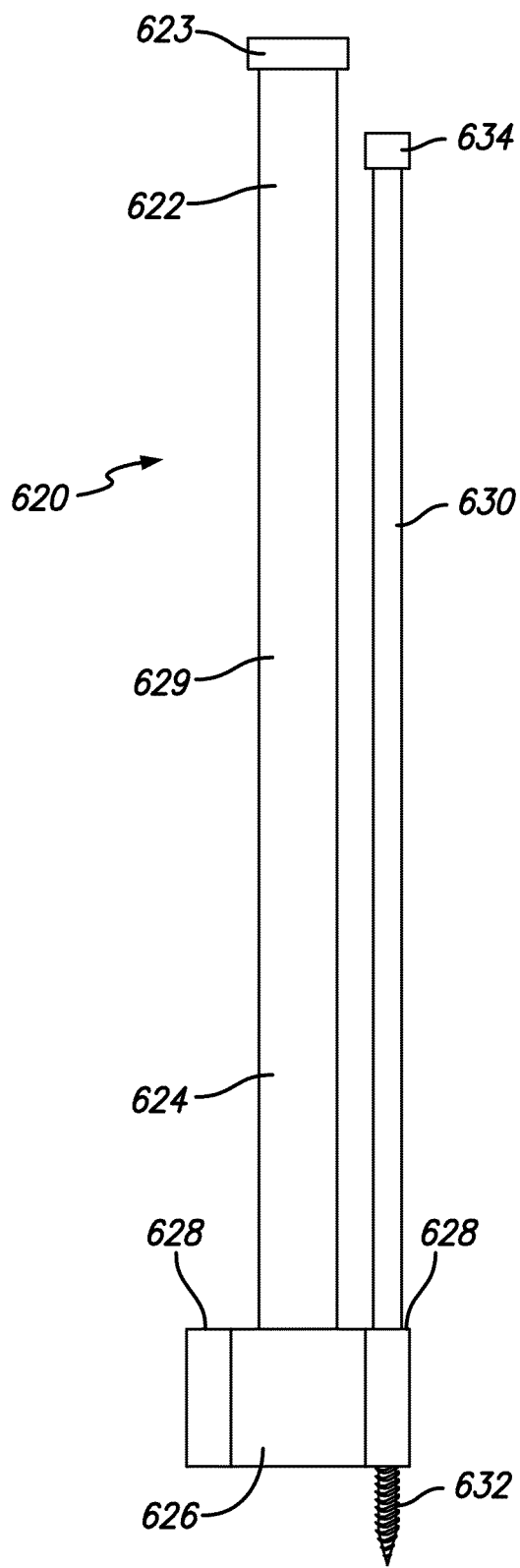
FIG. 37 is a rear plan view of the auxiliary blade of FIG. 34 without the threaded blade attachment screw.
Figure 38:
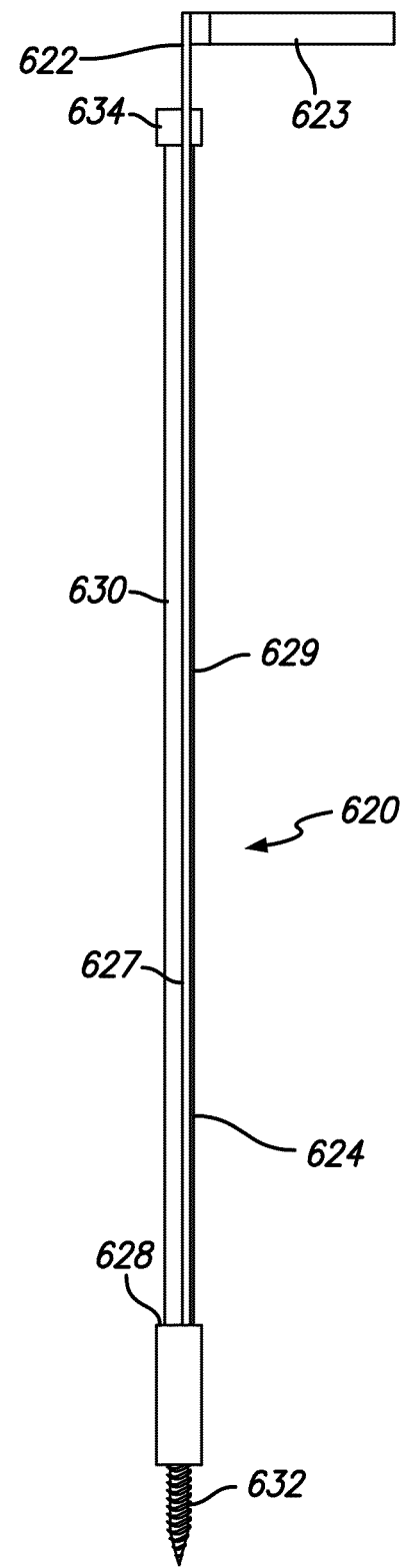
FIG. 38 is a side plan view of the auxiliary blade of FIG. 34 without the threaded blade attachment screw.
Figure 39:
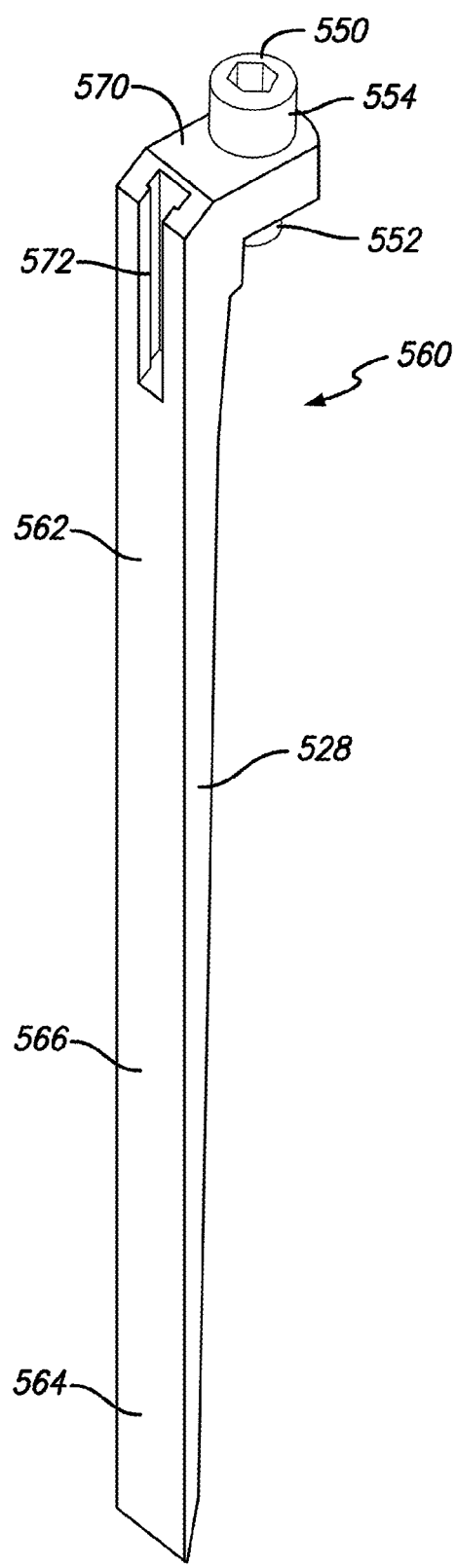
FIG. 39 is a front perspective view of another embodiment of a center blade including a threaded blade attachment screw of one embodiment of a retractor system of the present invention.
Figure 40:
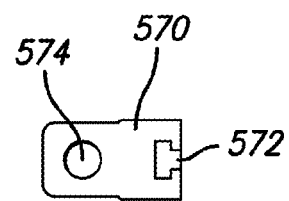
FIG. 40 is a top plan view of the center blade of FIG. 39 without the threaded blade attachment screw.
Figure 41:
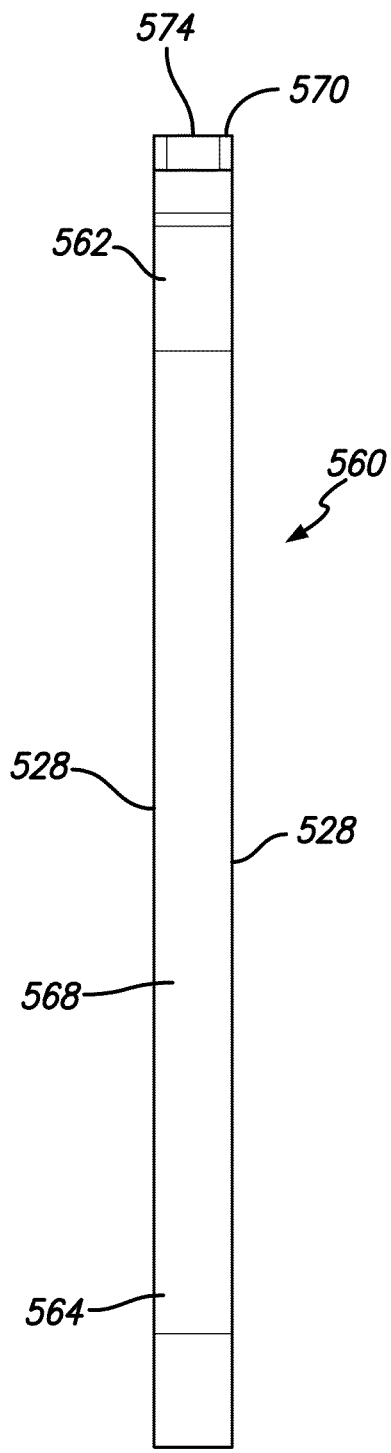
FIG. 41 is a back posterior plan view of the center blade of FIG. 39 without the threaded blade attachment screw.
Figure 42:
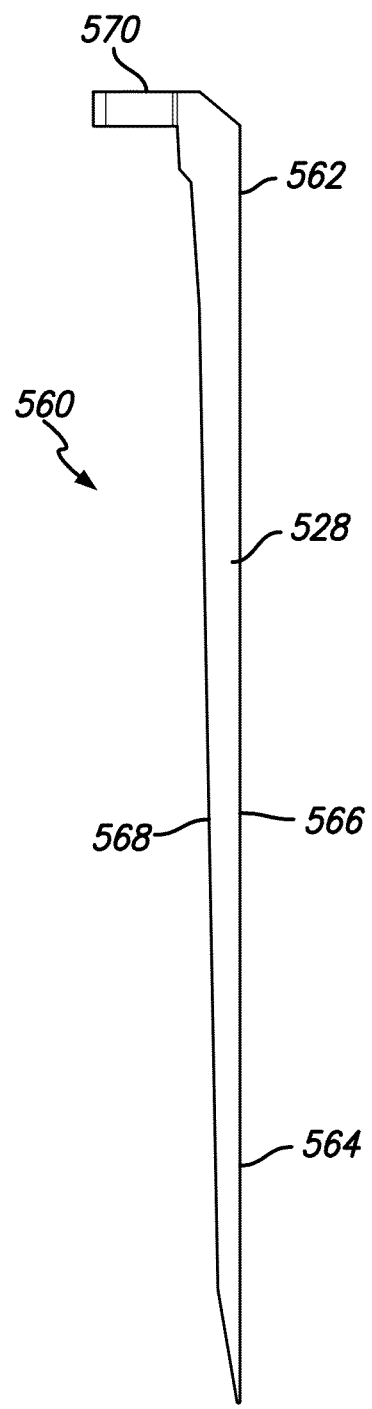
FIG. 42 is a side plan view of the center blade of FIG. 39 without the threaded blade attachment screw.
Figure 43:
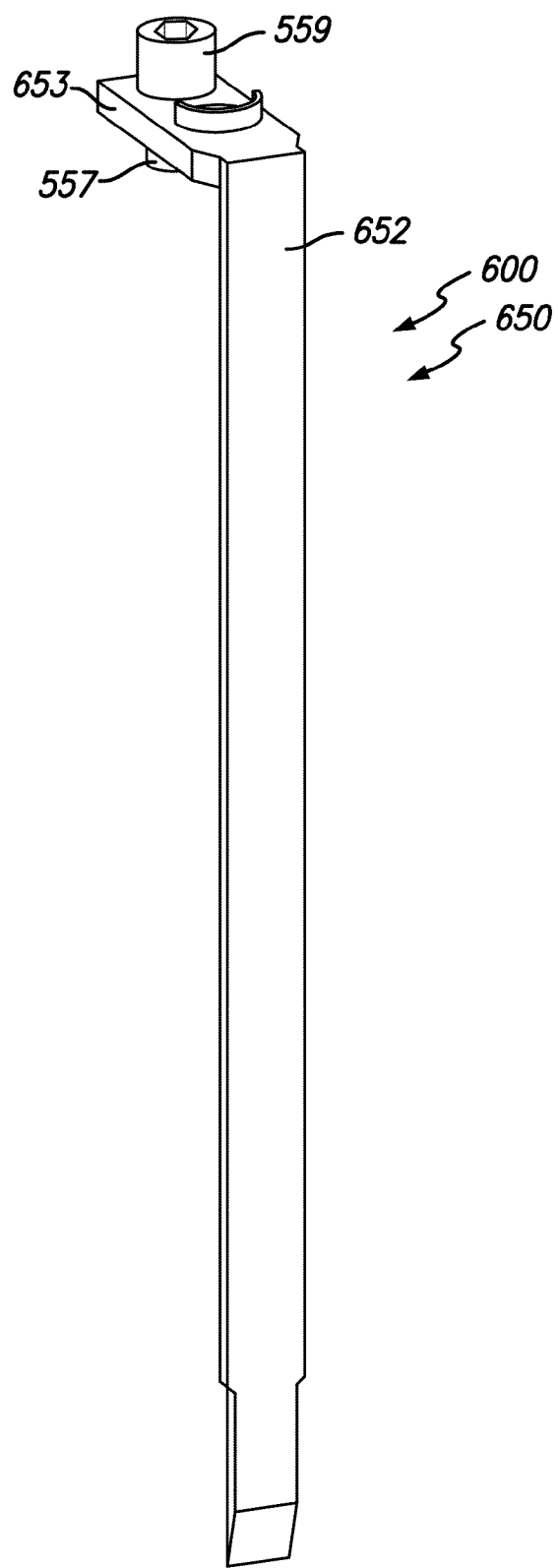
FIG. 43 is a perspective view of yet another embodiment of an auxiliary blade of an embodiment of the retractor system of the present invention including a threaded blade attachment screw.
Figure 44:
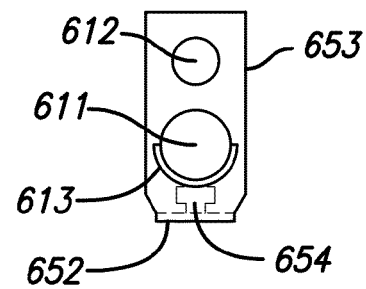
FIG. 44 is a top plan view of the auxiliary blade of FIG. 43 without the threaded blade attachment screw.
Figure 45:
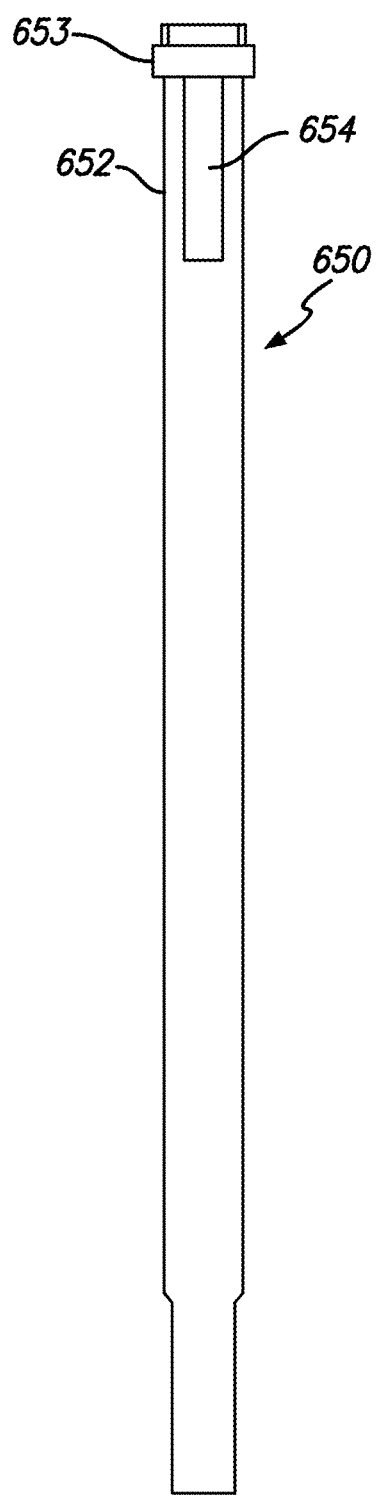
FIG. 45 is a rear plan view of the auxiliary blade of FIG. 43 without the threaded blade attachment screw.
Figure 46:
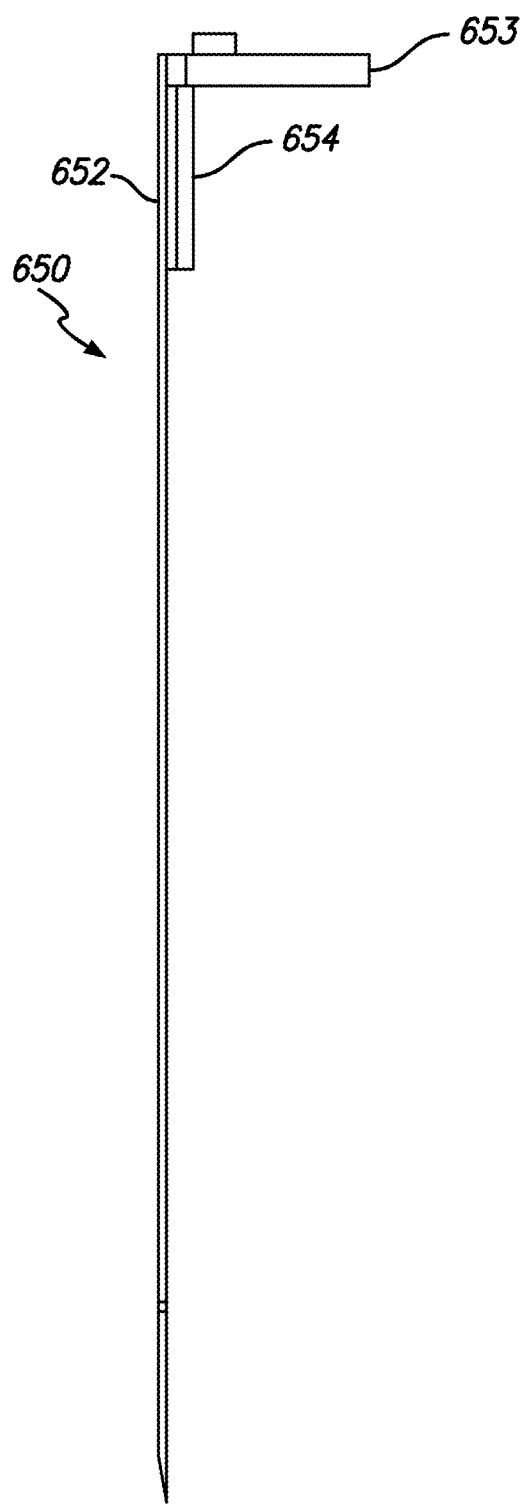
FIG. 46 is a side plan view of the auxiliary blade of FIG. 43 without the threaded blade attachment screw.

Referring now to FIGS. 29-38, in yet another embodiment an auxiliary blade 610, 620 may be provided. The auxiliary blades include an inner face 627 and an outer face 629. The auxiliary blades 610, 620 include proximal ends 602, 622 that include perpendicularly extending attachment members 603, 623 configured to connect with the frame body 402 and/or a center blade. In at least one embodiment, attachment members 603, 623 may include a first hole 611 that is larger than a second hole 612 (FIG. 30). In one embodiment, the first hole 611 includes a raised rim 613. The first hole 611 is sized to pass the grip end 554 of center blade attachment screw 550 therethrough. The second hole is sized to pass the threaded end 557 of auxiliary blade attachment screw 558 therethrough without permitting the passage of grip end 559 of auxiliary blade attachment screw 558. In one embodiment the hole 612 is unthreaded. In another embodiment the hole 612 is threaded. In one embodiment, following placement of a center blade attachment screw 550, an auxiliary blade 610, 620 may be detachably connected with the frame body by passing first hole 611 of proximal end 602, 622 attachment members 603, 623 over the grip end 554 of center blade attachment screw 550, passing threaded end 557 of auxiliary blade attachment screw 558 through second hole 612 in auxiliary blade and into threaded hole 428 in center arm 420, and tightening auxiliary blade attachment screw 558 using grip end 559 to secure auxiliary blade 610, 620 to center arm 420 of retractor frame 402.

Referring briefly now to FIGS. 39-42 and 43-48, in at least one further embodiment, a center blade 560 inner face additionally includes a T-shaped slot 572 for slidingly mating with a complementary shaped T-shaped longitudinal tail 654 disposed on outer face of proximal end 652 of auxiliary blade 650. Mating of a shaped slot 572 with a complementary shaped tail 654 functions similar to a dove tail joint and may provide additional stability to auxiliary blade 650, and further guides the auxiliary blade into position relative to the center blade. It is to be understood that complementary shapes other than T-shapes may be used for such matings. In at least one embodiment, auxiliary blade 650 proximal end 652 may include the complementary shaped tail 654, the first hole 611 in proximal end, and the second hole 612 in proximal end of an auxiliary blade, wherein the auxiliary blade 650 may be secured to both the posterior center blade 560 and to the frame body 402 as described above. The T-shaped mating may be provided on other embodiments of the center blades and the auxiliary blades. In one embodiment attachment screws 480, 550, 558 are all identical. In another embodiment, the primary blade attachment screws 480, center blade attachment screws 550, and auxiliary blade attachment screws 558 may differ in size, shape, grip, length, thread configurations, or other attributes.

Figure 47:
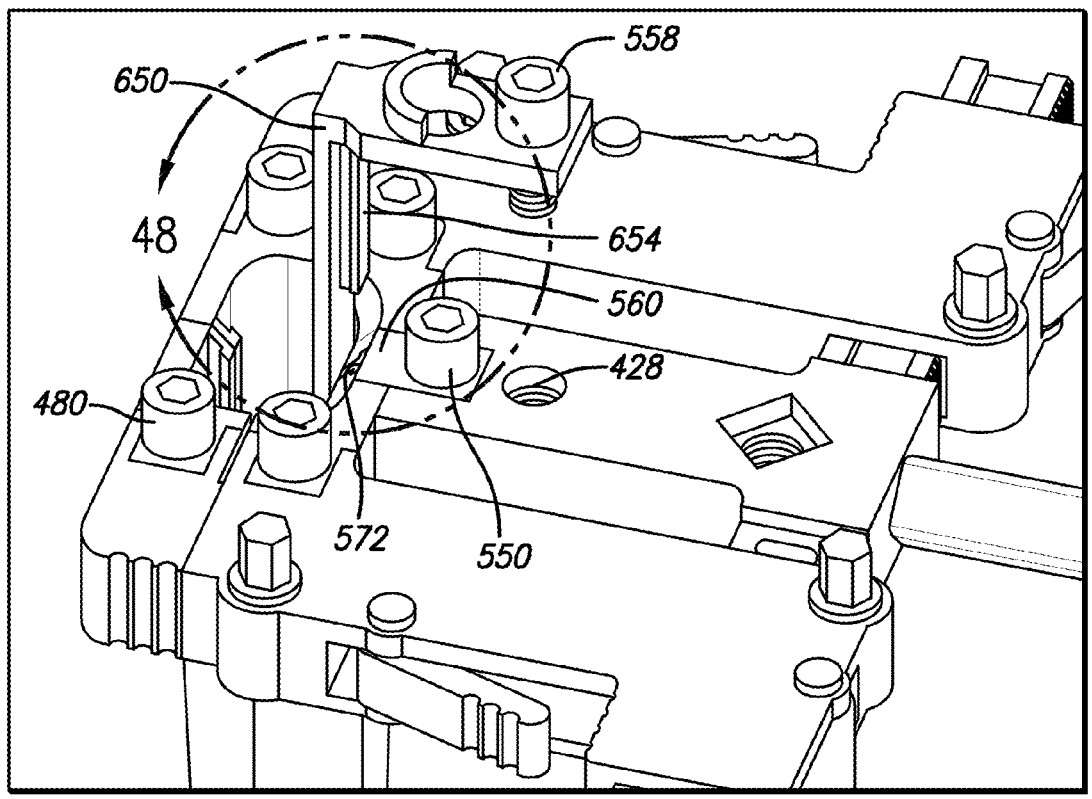
FIG. 47 is a perspective view illustrating the mating configuration of one embodiment of an auxiliary blade with one embodiment of a posterior center blade and one embodiment of a retractor frame.
Figure 48:
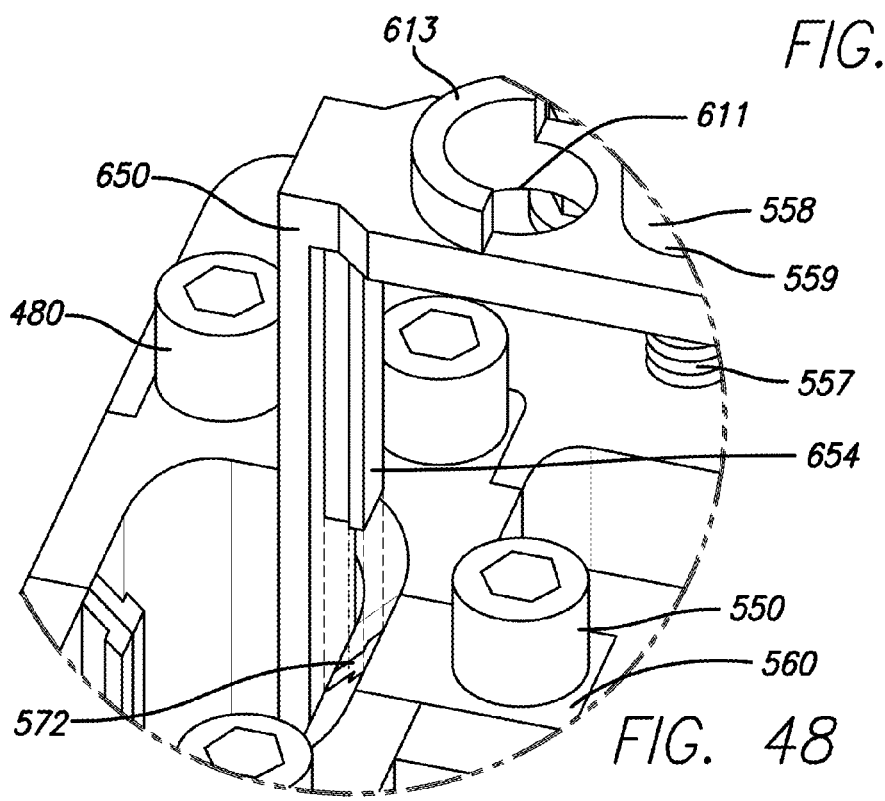
FIG. 48 is a magnified perspective view of FIG. 47 illustrating the mating configuration of one embodiment of an auxiliary blade with one embodiment of a posterior center blade and one embodiment of a retractor frame.

Referring more specifically now to FIGS. 29-33, one embodiment of an auxiliary blade 610 has a proximal end 602 and a distal end 604. The proximal end may include perpendicularly extending attachment member 603 as described above. The distal end 604 includes a narrowed portion 606. The distal end 604 of narrowed portion 606 may have a chisel shaped tip or a blunted tip. The portions of the auxiliary blade that are closer to the proximal end 604 are wider than the distal end narrowed portion 606. The narrowed portion may be inserted into a disc space 20 between two vertebral bodies 10. The narrowed portion 606 of the auxiliary blade 610 may act as a shim to distract open the disc space and may also function to stabilize the auxiliary blade 610. At least one embodiment of the auxiliary blade 610 also may be provided with a shaped longitudinal tail 654 disposed on proximal end 602 of auxiliary blade 610 for mating with a complementary shaped slot 572 on posterior center blade 560 (FIGS. 47 and 48). At least another embodiment of the auxiliary blade 610 may be provided without the shaped longitudinal tail 654.

Referring more specifically now to FIGS. 34-38, in yet another embodiment of an auxiliary blade 620, a distal end 624 includes a wider portion 626 compared to a more proximal narrow portion 633 of the auxiliary blade 620. A proximal end 622 may include perpendicularly extending attachment member 623 as described above. In one embodiment, proximal end 622 and/or narrow portion 633 of auxiliary blade 620 may be curved, for example generally concave along an inner face 627. In another embodiment, proximal end 622 and/or narrow portion 633 of auxiliary blade 620 may be curved, for example generally convex along an inner face 627. In one embodiment, proximal end 622 and/or narrow portion 633 of auxiliary blade 620 may be curved, for example generally convex along an outer face 629. In yet another embodiment, proximal end 622 and/or narrow end 633 of auxiliary blade 620 may be generally flat along the inner face 627. In yet another embodiment, proximal end 622 and/or narrow end 633 of auxiliary blade 620 may be generally flat along the outer face 629. In at least one further embodiment, widened distal portion 626 of auxiliary blade 620 may be generally concave along the inner face. In another embodiment, widened distal portion 626 of auxiliary blade 620 may be generally convex along the inner face. In still another embodiment, widened distal portion 626 of auxiliary blade 620 may be generally flat. A widened distal portion of an auxiliary blade may be advantageous in protecting the spinal canal during surgery. In one embodiment the auxiliary blade 620 may include at least one longitudinal channel 628 configured to receive an elongated anchor pin 630 therethrough. Anchor pin may include a distal threaded end 632 and a proximal grip end 634. The anchor pin may be rotated at the grip end to threadingly anchor the distal threaded end into bone, for example, into one or more vertebral bodies 10. The proximal end 634 of the anchor pin 630 may be rotated by hand or by use of a tool (not shown). In an embodiment of an auxiliary blade having two longitudinal channels 628, one or two anchor pins 630 may be utilized. The wide ended auxiliary blade 620 with longitudinal channels 628 may also be used without an anchor pin 630. At least one embodiment of the auxiliary blade 620 may be provided with a shaped longitudinal tail 654 disposed on proximal end 622 of auxiliary blade 620 for mating with a complementary shaped slot 572 on posterior center blade 560 (FIGS. 47 and 48). At least another embodiment of the auxiliary blade 620 may be provided without the shaped longitudinal tail 654.

Referring to FIGS. 1, 49, 50, 54, and 55, the invention further includes a method of using the dilator system 40 and/or retractor system 400 for minimally traumatic dilation and/or retractor of soft tissues. In one embodiment, the dilator system 40 and/or retractor system 400 may be used for access to a vertebral body 10 and/or disc space 20. For example, the dilator system 40 and/or retractor system 400 may be used to dilate and/or retract soft tissues during spinal arthrodesis or spinal arthroplasty surgery. However, the steps provided herein may be applicable to other procedures requiring dilation of biological tissues and/or retraction of biological tissues.

In one embodiment, the invention includes a method of providing less dilation in a first direction, which is transverse to the longitudinal axis of the first dilator 100, than the dilation provided in a second direction, which is also transverse to the longitudinal axis of the first dilator 100. The method may include providing greater dilation is towards an anterior frontal aspect of at least one dilator than towards a posterior rear aspect of the at least one dilator. The method may include providing relatively greater anatomically anterior dilation than anatomically posterior dilation relative to a guidewire, K-wire, and/or a first dilator 100. The method includes providing a first dilator 100 having a generally circular shaped exterior wall 132. In other embodiments, the method may include providing a first dilator that is multisided. In yet another embodiment a first dilator having various other symmetrical or asymmetrical shapes may be provided. The first dilator may advance through soft tissue, with or without rotation about the dilator's longitudinal axis, with minimal trauma to the tissue. In at least one embodiment the first dilator has a lumen 140. A guidewire 50 may be passed through the lumen and into an intervertebral disc space. The guidewire may be helpful in preventing movements of the first dilator during additional steps of the method. In yet another embodiment, a guidewire may be passed into the patient and the lumen of the first dilator subsequently advanced over the guidewire. The guidewire may be placed on the intervertebral body disc space and the first dilator advanced over the guidewire to the vertebral bodies. The method may further include providing a second dilator 200 having a generally circular shaped channel 240 that may be positioned offset from a central longitudinal axis of the second dilator. The channel may include an opening in the wall 230 of the second dilator that is formed by a longitudinal gap 250 in the wall. The method includes slidingly engaging the channel 240 of the second dilator 200 over a proximal end 110 of the first dilator 100 and advancing the second dilator distally. The channel of the second dilator, which may be disposed more proximate to the posterior rear aspect of the second dilator, provides minimized dilation in a first direction towards the posterior rear aspect of the second dilator. The method may provide minimized posterior dilation towards the gap 250 in a posterior wall 243 of the second dilator. The method may further include providing greater dilation in a direction towards the anterior frontal aspect of the second dilator. In a further embodiment, the method includes providing a third dilator 300 having a channel 340 generally matching the shape of an exterior wall 232 of the second dilator 200. The channel in the third dilator 300 may be positioned offset from a central longitudinal axis of the third dilator. The method may include providing a third dilator having a channel that is disposed more proximate to the posterior rear aspect of the third dilator than to the anterior frontal aspect of the third dilator. The channel 340 may include an opening in the wall of the third dilator that is formed by a longitudinal gap 350 in the wall of the third dilator. The method may include slidingly engaging the channel of the third dilator over and/or about proximal ends 110, 210 of the first dilator 100 and second dilator 200 and advancing the third dilator distally. The method may include aligning the gap 350 in the wall of the third dilator with the gap 250 in the wall in the second dilator, wherein the off center channels of the second dilator and the third dilator, wherein the channels are disposed more proximate the posterior rear aspects of the dilators than the anterior frontal aspects of the dilators, provide minimized dilation in a first direction towards the gaps 250, 350 and towards the posterior rear aspect of the second dilator, and/or towards the posterior rear aspect of the third dilator. In at least one embodiment, the method includes minimizing dilation of soft tissues that are anatomically posterior to the most anatomically posterior position of the exterior wall 132 of the first dilator 100. In yet another embodiment the method includes minimizing dilation of tissue towards posterior walls of the second dilator and third dilator. The method may include providing greater dilation of tissues towards the anterior frontal aspect of the second dilator and/or the third dilator.

In yet another embodiment, the invention includes a method of providing less dilation in a first direction, which may be transverse to the longitudinal axis of the first dilator 100, than the dilation provided in a different second direction, which may be transverse to the longitudinal axis of the first dilator 100, that may be less than the dilation provided in yet a different third direction, which may also be transverse to the longitudinal axis of the first dilator. In yet another embodiment the method includes advancing a second dilator and a third dilator over a stationary positioned first dilator, wherein greater dilation is provided in an anatomic rostral or caudal direction, than an anatomic anterior direction, and still further minimizing or avoiding dilation in an anatomic posterior direction. The method may include providing a second dilator 200 having a generally oblong exteriorly shaped wall 232. The second dilator may include a circular channel 240 that is positioned off center in the second dilator 200 towards a posterior wall 243 longitudinal gap 250. The channel 240 may include an opening in the wall 230 of the second dilator that is formed by the posterior wall longitudinal gap 250. The method may include slidingly engaging the channel 240 of the second dilator 200 over a proximal end 110 of the first dilator 100 and advancing the second dilator distally, wherein the first dilator exterior wall 132 at least partially fills the second dilator 200 longitudinal gap 250. The off-center channel of the second dilator thereby minimizes dilation is a first posterior direction where the gap is positioned, and provides greater dilation is an anterior second direction. Furthermore, the oblong exterior wall shape of the dilator provides greater dilation in a left-right third direction, for example, an anatomic rostral-caudal direction, than the dilation provided in either the first posterior direction or the second anterior direction. In at least on embodiment the method includes advancing the generally oblong shaped second dilator 200 over a generally circular shaped first dilator 100 with the posterior longitudinal gap 250 in an anatomically posterior position, wherein the most dilatation is achieved in an anatomical rostral-caudal direction and the least dilatation is provided in an anatomical posterior direction. The amount of anatomically anterior dilatation provided by at least one embodiment may be between the amount of anatomically posterior dilatation and the amount of anatomically rostral-caudal dilatation. In yet another embodiment the method includes advancing the generally oblong shaped second dilator 200 over a generally circular shaped first dilator 100 with the posterior longitudinal gap 250 in an anatomically posterior position, no dilation is provided in an anatomical posterior direction.

In yet a further embodiment, the method includes providing at least one additional oblong dilator having a channel 340 disposed more proximate to a posterior rear aspect of the dilator than the anterior frontal aspect of the dilator. The channel may communicate with an opening formed by a posterior longitudinally extending gap 350 in the at least one additional oblong dilator wall. In at least one embodiment, the at least one additional oblong dilator may have an oblong channel 340 having a central longitudinal axis that may be offset from the central longitudinal axis of the exterior wall of the at least one additional oblong dilator.

The method includes slidingly engaging the channel 340 of the at least one additional oblong dilator over a proximal end of the first dilator 100 and/or the second dilator 200, and advancing the at least one additional oblong dilator distally over the first dilator and/or second dilator, wherein the first dilator 100 and/or second dilator 200 exterior wall at least partially fills the at least one additional oblong dilator longitudinal gap 350. The off-center channel 340 of the at least one additional oblong dilator 300 thereby minimizes dilation is a first posterior direction where the gap is positioned, and provides greater dilation in an anterior second direction. Furthermore, the oblong exterior wall shape of the at least one additional oblong dilator provides greater dilation in a left-right third direction than the dilation provided in either the first posterior direction or the second anterior direction. In at least on embodiment the method includes advancing the oblong at least one additional dilator over the second dilator 200 with the posterior longitudinal gaps 250, 350 in an anatomically posterior position, wherein the most dilatation is achieved in an anatomical rostral-caudal direction and the least dilatation is provided in an anatomical posterior direction. In one embodiment, the at least one additional dilator 300 is advanced over the second dilator 200 without any dilation of tissues posterior to the exterior wall 132 of the first dilator 100. In one further embodiment, the at least one additional dilator 300 is advanced over the second dilator 200 without any dilation of tissues posterior to the exterior wall 232 of the second dilator 200. The amount of anatomically anterior dilatation provided by the at least one additional oblong dilator may be between the amount of anatomically posterior dilatation and the amount of anatomically rostral-caudal dilatation. In one embodiment, the at least one additional oblong dilator may be slidingly advanced over the second oblong dilator 200 while the second dilator is positioned over the first generally circular dilator 100. The method may provide dilatation in a first direction, which is less than the dilatation in a second direction, which may be less than dilation in a third and/or fourth direction, all directions being generally perpendicular to a central longitudinal axis of at least one of the dilators 100, 200, 300. In at least one embodiment, the methods herein are useful in obtaining lateral access to the vertebral bodies and/or disc spaces of the spine, for example, for discectomy, arthrodesis, arthroplasty, or biopsy.

In yet another embodiment, a method of monitoring proximity of nerves to the dilators is provided. The method includes stimulating at least one electrode extending longitudinally through the wall of at least one dilator. The method may include interpretation of a muscle response from muscle innervated from nerves traversing near the wound being dilated. The method may include using the dilators of the present invention to evoke a triggered EMG response and a physician interpreting the triggered EMG response, wherein proximity of at least one of the dilators to nerves in the tissue may be determined or estimated.

In still another embodiment a method of safely reaching the spine in the direct lateral transpsoas approach by monitoring proximity of nerves to dilators is provided. The method includes stimulating at least one electrode of the first dilator 100 while docking the first dilator tip to the target disc space 20 while in the transpsoas approach. The surgeon may then assess the proximity of the dilator to the nerves by performing triggered EMG. The proximity of the dilator to the Lumbar Plexus, which is normally located towards an anatomically posterior position relative to the vertebral body 10 is especially important in the transpsoas approach. Once the posterior most position of the first dilator is established as being positioned at a safe distance from the Lumbar Plexus, the guidewire 50 may be passed through the lumen and into an intervertebral disc space 20 to lock the first dilator position. A subsequent oblong dilator 200 is then slidingly advanced over the first dilator 100 without any dilation of tissues posterior to the exterior wall 132 of the first dilator 100, thereby minimizing the probability of the Lumbar Plexus injury. In one embodiment, the at least one additional oblong dilator may be slidingly advanced over the second oblong dilator 200 while the second dilator is positioned over the first generally circular dilator 100 without any dilation of tissues anatomically posterior to the first dilator's exterior wall 132.

In still another embodiment a method of providing retraction of soft tissues is provided. The method may include slidingly engaging at least one embodiment of the retractor system 400 disclosed herein over at least one embodiment of the dilator system 40 disclosed herein. In one embodiment, the method includes slidingly positioning the retractor system over the dilator system with the retractor in the closed position 490. The method may further include transitioning the retractor system from the closed position towards at least one or more open position 492. The retractor system may be transitioned to at least one open position while minimizing/eliminating retraction in one direction. In at least one embodiment, the method includes slidingly engaging a retractor system having an oblong working channel in a closed position over at least one dilator having an oblong exterior wall. The method further includes enlarging the oblong working channel in at least one direction by linearly translational movement at least one retractor blade. In at least one embodiment the linearly translational movement of at least one retractor blade is produced by a user operating a rack and pinion mechanism of the retractor frame. The method may include anchoring the retractor system to the operating table. The method may include anchoring at least one retractor blade to bone using an anchor pin.

In at least one embodiment, the method includes slidingly engaging a retractor system having an oblong working channel in a closed position over at least one dilator having an oblong exterior wall while in the transpsoas approach to the spine. The method further includes enlarging the oblong working channel in at least one anatomical direction that may be caudal, cephalad, and/or anterior by linearly translational movement of at least one retractor blade while minimizing/eliminating tissue retraction in the anatomical posterior direction to spare the Lumbar Plexus from compression or stretch injury.

Referring briefly now to FIGS. 56-59, in one further embodiment the second dilator 200 may include lateral walls 244 that are thinner than the anterior wall 242, wherein transverse tissue dilation in an anatomically rostral and/or anatomically caudal direction may be minimized while maximizing anatomically anterior dilation of tissues and eliminating or minimizing anatomically posterior dilation of tissues. Furthermore, the third dilator 300 may include lateral walls 344 that are thinner than anterior wall 342, wherein transverse tissue dilation in an anatomically rostral and/or anatomically caudal direction may be minimized while maximizing anatomically anterior dilation of tissues and eliminating or minimizing anatomically posterior dilation of tissues.

Referring again now to FIGS. 5, 61 and 62, one embodiment of invention is a method of rotating the second dilator 200 one hundred and eighty degrees and/or the third dilator one hundred and eighty degrees to provide different amounts of anterior or posterior dilation of soft tissues. In at least one embodiment, FIG. 5, the method of use of the dilator system includes positioning the gap in the second dilator and the gap in the third dilator on the same side relative to the first dilator. In another embodiment, FIGS. 61 and 62, the method of use of the dilator system includes positioning the gap in the second dilator and the gap in the third dilator on the opposite sides relative to the first dilator. Referring to FIG. 61, one method includes positioning the gap in the second dilator anatomically posteriorly and the gap in the third dilator anatomically anteriorly. Referring to FIG. 62, one method includes positioning the gap in the third dilator anatomically posteriorly and the gap in the second dilator anatomically anteriorly.

In at least one embodiment the method of obtaining lateral access includes removing the generally oblong shaped second and/or third dilator 200, 300 if final dilator assembly 40 is found to be placed too anatomically anterior and advancing the generally oblong shaped second and/or third dilator 200, 300 turned 180 degrees along its longitudinal axis, where the gaps 250 and/or 350 face the anterior direction. This method is useful since it does not require the guidewire and/or the first dilator to be replaced in order to achieve a more posterior final position.

Figure 67:
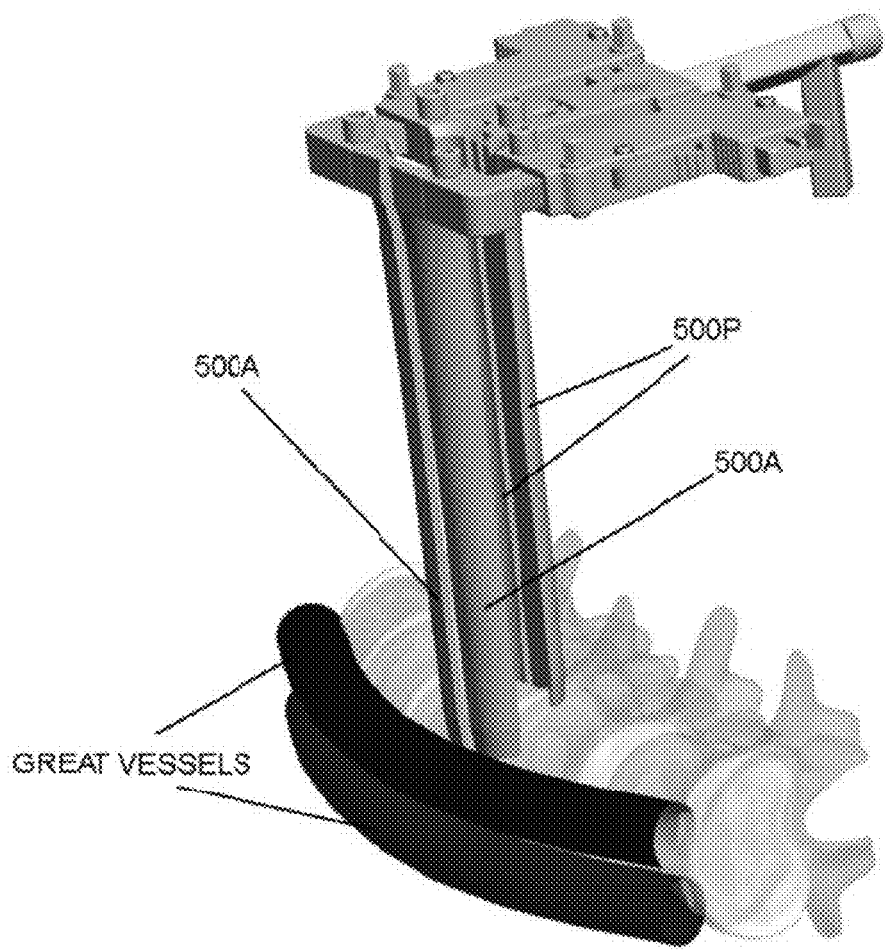
FIG. 67 is a perspective view of one embodiment of an assembly of a retractor system of the present invention positioned over a human spine and great vessels.

Referring also now to FIG. 67, in at least one additional embodiment, the method includes slidingly engaging a retractor system having anterior primary blades 500A longer than posterior primary blades 500P. The method further includes retracting tissue in the anatomical anterior direction until the anterior primary blades can slide down towards the anatomical midline at the anatomically anterior portion of the vertebral bodies, wherein the anterior primary blades may be positioned behind the great vessels. This is useful when great vessel protection is needed during removal of anatomically anterior portions of the intervertebral disc and/or removal of the anterior longitudinal ligament.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

I claim:

1. A dilator system comprising:
   a first dilator including a wall having an exterior first cross-sectional shape, and the first dilator having a first longitudinal axis extending from a proximal end of the first dilator to a distal end of the first dilator and centrally disposed relative to the exterior first cross-sectional shape;
   a second dilator including a wall having an interior second cross-sectional shape and an exterior third cross-sectional shape, wherein the interior second cross-sectional shape is configured to mate with the exterior first cross-sectional shape, the periphery of the interior second cross-sectional shape and the exterior third cross-sectional shape being at least partially interrupted by a longitudinal gap extending at least a portion of the length of the second dilator, wherein the second dilator further includes a channel having a longitudinal opening formed by the longitudinal gap, the channel being configured to slidingly receive the first dilator therethrough;

wherein the interior second cross-sectional shape of the second dilator wall comprises an interior straight-line segment and the exterior third cross-sectional shape of the second dilator wall comprises an exterior straight-line segment, and the interior straight-line segment and the exterior straight-line segment are parallel to each other; and wherein the exterior straight-line segment is longer than the interior straight-line segment.

2. The dilator system of claim 1, wherein the second dilator has a second longitudinal axis extending from a proximal end of the second dilator to a distal end of the second dilator and centrally disposed relative to the interior second cross-sectional shape, and wherein the second dilator has a third longitudinal axis extending from the proximal end of the second dilator to the distal end of the second dilator and centrally disposed relative to the exterior third cross-sectional shape, wherein the second longitudinal axis is generally parallel to and offset from the third longitudinal axis.

3. The dilator system of claim 1, wherein the exterior first cross-sectional shape is generally circular.

4. The dilator system of claim 1, wherein the exterior third cross-sectional shape is generally oblong.

5. The dilator system of claim 1, wherein at least one of the dilators includes longitudinally extending electrical conducting members.

6. The dilator system of claim 1, wherein at least one of the dilators includes a grip surface on the proximal end.

7. The dilator system of claim 1, wherein at least one of the dilators includes radiopaque markers.

8. The dilator system of claim 1, wherein when the channel of the second dilator slidingly receives the first dilator therethrough, the exterior wall of the first dilator substantially fills the longitudinal gap in the second dilator.

9. The dilator system of claim 1, wherein the first dilator includes a central lumen axially aligned with the first longitudinal axis and configured to receive a guidewire therethrough.

10. A dilator system comprising:
a first dilator including a wall having an exterior first cross-sectional shape, and a first longitudinal axis centrally disposed relative to the exterior first cross-sectional shape and extending from a proximal end of the first dilator to a distal end of the first dilator;
a second dilator including a wall having an interior second cross-sectional shape such that the exterior first cross-sectional shape of the first dilator can fit therein, and an exterior third cross-sectional shape substantially different from the exterior first cross-sectional shape of the first dilator, the periphery of the second cross-sectional shape and the third cross-sectional shape being at least partially interrupted by a first longitudinal gap extending a majority of the longitudinal length of the second dilator, wherein the second dilator wall includes an exterior straight-line segment on the exterior third cross-sectional shape opposite the first longitudinal gap, a second longitudinal axis centrally disposed relative to the interior second cross-sectional shape and extending generally perpendicularly to the second cross-sectional shape from a proximal end of the second dilator to a distal end of the second dilator, a third longitudinal axis centrally disposed relative to the exterior third cross-sectional shape and extending generally perpendicularly to the third cross-sectional shape from the proximal end of the second dilator to the distal end of the second dilator, wherein the second longitudinal axis is generally parallel to and offset from the third longitudinal axis, and a first channel in the second dilator having a longitudinal opening formed by the first longitudinal gap, the first channel configured to slidingly receive a first dilator exterior wall therethrough;
a third dilator including a wall having an interior fourth cross-sectional shape such that the exterior third cross-sectional shape of the second dilator can fit therein, and an exterior fifth cross-sectional shape, the periphery of the interior fourth cross-sectional shape and the exterior fifth cross-sectional shape being at least partially interrupted by a second longitudinal gap extending a majority of the longitudinal length of the third dilator, wherein the third dilator wall includes an exterior straight-line segment on the exterior fifth cross-sectional shape opposite the second longitudinal gap and an interior straight-line segment on the interior fourth cross-sectional shape opposite the second longitudinal gap, and the interior straight-line segment and the exterior straight-line segment are parallel to each other, and wherein the exterior straight-line segment is longer than the interior straight-line segment, a fourth longitudinal axis centrally disposed relative to the interior fourth cross-sectional shape of the third dilator and extending generally perpendicular to the fourth cross-sectional shape from a proximal end of the third dilator to a distal end of the third dilator, a fifth longitudinal axis centrally disposed relative to the exterior fifth cross-sectional shape of the third dilator and extending generally perpendicular to the fifth cross-sectional shape of the third dilator from the proximal end of the third dilator to the distal end of the third dilator, wherein the fourth longitudinal axis is generally parallel to and offset from the fifth longitudinal axis, and a second channel in the third dilator having a longitudinal opening formed by the second longitudinal gap, the second channel configured to mate with and slidingly receive a the second dilator exterior wall therethrough;
wherein the first, second and third dilators can be assembled in a cumulative configuration in which the second dilator can be assembled around the first dilator and the third dilator can be assembled around the second dilator such that an off-centeredness of the second dilator and an off-centeredness of the third dilator cumulatively add to each other in a defined direction relative to the first dilator;
wherein the first, second and third dilators can be assembled in a non-cumulative configuration in which the second dilator can be assembled around the first dilator and the third dilator can be assembled around the second dilator such that the off-centeredness of the second dilator and the off-centeredness of said third dilator do not cumulatively add to each other in a defined direction relative to the first dilator; and
wherein when the first, second and third dilators are assembled in the non-cumulative configuration and an envelope of the third dilator is defined by extending a straight line across the gap of the third dilator such that the straight line is tangent to the external surface of the third dilator at each side of the gap, the second dilator is contained entirely within the envelope of the third dilator.

11. The dilator system of claim 10, wherein an exterior wall of the first dilator at least partially fills the first longitudinal gap in the second dilator when the second dilator is slidingly positioned over the first dilator.

12. The dilator system of claim 10, wherein the exterior wall of the second dilator at least partially fills the second longitudinal gap in the third dilator when the third dilator is slidingly positioned over the second dilator.

13. The dilator system of claim 10, wherein an exterior wall of the first dilator and the exterior wall of the second dilator substantially fills the second longitudinal gap in the third dilator when the third dilator is slidingly positioned over the first dilator and the second dilator.

14. The dilator system of claim 10 wherein the exterior first cross-sectional shape is round, the exterior third cross-sectional shape is oblong, and the exterior fifth cross-sectional shape is oblong.

15. The dilator system of claim 10 wherein at least one of the dilators includes longitudinally extending electrical conducting members.

16. A dilator system comprising: a first dilator having an exterior periphery defined by an exterior wall; a second troughlike dilator having a longitudinal direction, including an open proximal end, an open distal end, and a channel configured to slidingly mate the first dilator therein, the channel having a longitudinally extending gap disposed between a left side portion and a right side portion of a wall of the second dilator and configured to prevent dislodgment of the first dilator through the gap; wherein in a cross-section taken perpendicular to the longitudinal direction, the second dilator comprises an external straight-line segment on the exterior periphery opposite the gap and an internal straight-line segment on the interior periphery opposite the gap, wherein the external straight-line segment is longer than the internal straight-line segment, and wherein the second dilator has a gap width being a dimension of a largest object that can pass from an exterior region of the second dilator to an interior region of the second dilator; and wherein the length of the external straight-line segment is longer than the gap width.

17. The dilator system of claim 16, wherein an exterior periphery about the second dilator is defined in part by an exterior wall of the second dilator and in part by an imaginary tangent line extending across the gap and tangent at each end to the contour of the exterior wall near the gap, and wherein the external straight-line length is longer than the length of the tangent line.

\* \* \* \* \*